United States Patent [19]

Daniels

[11] 4,000,262
[45] Dec. 28, 1976

[54] 5-EPI-AMINO AND 5-EPI-AZIDO-4,6-DI-O-(AMINO-GLYCOSYL)-2,5-DIDEOXYSTREPTAMINES 1-N-ALKYL-5-EPI-AMINO AND 1-N-ALKYL-5-EPI-AZIDO-4,6-DI-O-(AMINO-GLYCOSYL)-2,5-DIDEOXYSTREPTAMINES

[75] Inventor: Peter J. L. Daniels, Cedar Grove, N.J.

[73] Assignee: Schering Corporation, Kenilworth, N.J.

[22] Filed: Sept. 8, 1975

[21] Appl. No.: 611,290

Related U.S. Application Data

[63] Continuation-in-part of Ser. No. 528,592, Nov. 29, 1974, abandoned.

[52] U.S. Cl. .................. 424/180; 536/17; 536/10
[51] Int. Cl.² ................ A61K 31/71; C07H 15/22
[58] Field of Search .... 260/210 R, 210 AB, 210 K; 424/180

[56] References Cited

UNITED STATES PATENTS

| | | | |
|---|---|---|---|
| 3,828,021 | 8/1974 | Beattie et al. | 260/210 AB |
| 3,920,628 | 11/1975 | Daniels | 260/210 AB |

*Primary Examiner*—Johnnie R. Brown
*Attorney, Agent, or Firm*—Mary S. King

[57] ABSTRACT

5-Epi-azido- and 5-epi-amino-4,6-di-O-(aminoglycosyl)-2,5-dideoxystreptamines and 1-N-alkyl derivatives thereof, valuable as antibacterial agents, are prepared from the corresponding 5-O-hydrocarbonsulfonyl (or substituted hydrocarbonsulfonyl)-4,6-di-O-(aminoglycosyl)-2-deoxystreptamine wherein all other hydroxyl functions and all amino functions are protected, by the reaction thereof with an alkali metal azide in an organic solvent followed by the reaction of the resulting 5-epi-azido-4,6-di-O-(aminoglycosyl)-2,5-dideoxystreptamine with base to remove the protecting groups, or with hydrogen in the presence of a catalyst or with an alkali metal in liquid ammonia, and thence cleavage of any remaining hydroxyl and amino protecting groups in the thereby formed 5-epi-amino-4,6-di-O-(aminoglycosyl)-2,5-dideoxystreptamine or 1-N-alkyl derivative thereof.

In addition to the foregoing, methods are described whereby the 1-N-alkyl-5-epi-azido and 1-N-alkyl-5-epi-amino-4,6-di-O-(aminoglycosyl)-2,5-dideoxystreptamines are prepared from the corresponding 1-N-unsubstituted-5-epi-azido and 1-N-unsubstituted-5-epi-amino-4,6-di-O-(aminoglycosyl)-2,5-dideoxystreptamines.

Pharmaceutical compositions comprising 5-epi-amino-4,6-di-O-(aminoglycosyl)-2,5-dideoxystreptamines, 1-N-alkyl-5-epi-amino-4,6-di-O-(aminoglycosyl)-2,5-dideoxystreptamines, 5-epi-azido-4,6-di-O-(aminoglycosyl)-2,5-dideoxystreptamines and 1-N-alkyl-5-epi-azido-4,6-di-O-(aminoglycosyl)-2,5-dideoxystreptamines elicit an antibacterial response in a warm blooded animal having a susceptible bacterial infection.

44 Claims, No Drawings

5-EPI-AMINO AND 5-EPI-AZIDO-4,6-DI-O-(AMINOGLYCOSYL)-2,5-DIDEOXYSTREPTAMINES 1-N-ALKYL-5-EPI-AMINO AND 1-N-ALKYL-5-EPI-AZIDO-4,6-DI-O-(AMINOGLYCOSYL)-2,5-DIDEOXYSTREPTAMINES

CROSS REFERENCE TO RELATED APPLICATIONS

This application is a continuation-in-part of copending application Ser. No. 528,592, filed Nov. 29, 1974 the subject matter of which is incorporated herein by reference, now abandoned.

FIELD OF INVENTION

This invention relates to novel compositions-of-matter, to methods for their manufacture and intermediates useful therein, to pharmaceutical formulations and to methods for their use as antibacterial agents.

More specifically, this invention relates to novel 5-epi-amino and 5-epi-azido-4,6-di-O-(aminoglycosyl)-2,5-dideoxystreptamines and the 1-N-alkyl derivatives thereof having antibacterial activity, to methods for their manufacture, to pharmaceutical compositions thereof and to methods for their use in treating bacterial infections.

In particular, this invention relates to 5-epi-amino-5-deoxy and to 5-epi-azido-5-deoxy derivatives of 4,6-di-O-(aminoglycosyl)-2-deoxystreptamine antibacterial agents including the gentamicins, sisomicin, verdamicin, tobramycin, the kanamycins, Antibiotics G-418, 66-40B, 66-40D, JI-20A, JI-20B, G-52 and the 1-N-alkyl derivatives thereof.

This invention also relates to intermediates useful in the manufacture of the 5-epi-amino and 5-epi-azido antibacterial agents of the invention; in particular to the 5-epi-azido-4,6-di-O-(aminoglycosyl)-2,5-dideoxystreptamines and the 1-N-alkyl derivatives thereof having all hydroxyl functions and all amino functions protected by groups susceptible to reductive cleavage or to basic or mild acid hydrolysis.

This invention also relates to the processes for preparing the foregoing 5-epi-amino and 5-epi-azido-4,6-di-O-(aminoglycosyl)-2,5-dideoxystreptamines and their 1-N-alkyl derivatives, to pharmaceutical compositions comprising said 5-epi-amino or 5-epi-azido-4,6-di-O-(aminoglycosyl)-2,5-dideoxystreptamines and their 1-N-alkyl derivatives and to the method of using said pharmaceutical compositions to elicit an antibacterial response in a warm blooded animal having a susceptible bacterial infection.

PRIOR ART

Known in the art are broad spectrum antibacterial agents which may be classified chemically as 4,6-di-O-(aminoglycosyl)-1,3-diaminocyclitols. Valuable antibacterial agents of this group are those wherein the aminocyclitol is 2-deoxystrepamine. Particularly valuable antibacterials of the 4,6-di-O-(aminoglycosyl)-2-deoxystreptamines are those wherein the aminoglycosyl group at the 6-position is a garosaminyl radical. Within the class of 4-O-aminoglycosyl-6-O-garosaminyl-2-deoxystreptamines are antibiotics such as gentamicins B, $B_1$, $C_1$, $C_{1a}$, $C_2$, $C_{2a}$, $C_{2b}$ and $X_2$; sisomicin, verdamicin, Antibiotic G-418, Antibiotic G-52, Antibiotic JI-20A and Antibiotic JI-20B.

Also known in the art are 1-N-alkyl derivatives of the aforementioned 4,6-di-O-(aminoglycosyl)-1,3-diaminocyclitols which, in general, exhibit broad spectrum antibacterial activity and possess enhanced activity against bacteria resistant to the 1-N-unsubstituted antibacterial agent.

By my invention I have discovered methods whereby the hydroxyl function at the 5-position of the 2-deoxystreptamine or derivative thereof in a 4,6-di-O-(aminoglycosyl)-2-deoxystreptamine is replaced by a 5-epi-azido- or a 5-epi-amino function. I have discovered also that the 5-epi-amino- and 5-epi-azido-4,6-di-O-(aminoglycosyl)-2,5-dideoxystreptamines, their 1-N-alkyl derivatives and acid addition salts thereof thereby produced are valuable broad spectrum antibacterial agents possessing improved antibacterial activities compared to the parent antibiotics. Preferred compounds of my invention include 5-epi-amino- and 5-epi-azido-4,6-di-O-(aminoglycosyl)-2,5-dideoxystreptamines and 1-N-alkyl derivatives thereof, particularly those wherein the 6-O-aminoglycosyl group is 6-O-garosaminyl, which derivatives exhibit an improved antibacterial spectrum over that of the parent compound.

GENERAL DESCRIPTION OF THE INVENTION

COMPOSITION-OF-MATTER ASPECT

Included among the antibacterially active compositions-of-matter of this invention are 5-epi-X-4,6-di-O-(aminoglycosyl)-2,5-dideoxystreptamines selected from the group consisting of 5-epi-X-5-deoxygentamicin A,
5-epi-X-5-epi-X-deoxygentamicin B,
5-epi-X-5-deoxygentamicin $B_1$, 5-epi-X-5-deoxygentamicin $C_1$,
5-epi-X-5-deoxygentamicin $C_{1a}$, 5-epi-X-5-deoxygentamicin $C_2$,
5-epi-X-5-deoxygentamicin $C_{2a}$, 5-epi-X-5-deoxygentamicin $C_{2b}$,
5-epi-X-5-deoxygentamicin $X_2$, 5-epi-X-5-deoxysisomicin,
5-epi-X-5-deoxyverdamicin, 5-epi-X-5-deoxytobramycin, 5-epi-X-5-deoxy-Antibiotic G-418, 5-epi-X-5-deoxy-Antibiotic 66-40B,
5-epi-X-5-deoxy-Antibiotic 66-40D, 5-epi-X-5-deoxy-Antibiotic JI-20A,
5-epi-X-5-deoxy-Antibiotic JI-20B, 5-epi-X-5-deoxy-Antibiotic G-52,
5-epi-X-5,3',4'-trideoxykanamycin B, 5-epi-X-5-deoxykanamycin A
and 5-epi-X-5-deoxykanamycin B;
the 1-N-K derivatives of the foregoing,
wherein X is a member selected from the group consisting of amino and azido; K is an alkyl substituent selected from the group consisting of alkyl, alkylcycloalkyl, alkenyl, aralkyl, hydroxyalkyl, aminoalkyl, alkylaminoalkyl, aminohydroxyalkyl and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;

and the pharmaceutically acceptable acid addition salts thereof.

Particularly useful antibacterial agents of my invention include 5-epi-X-4,6-di-O-(aminoglycosyl)-2,5- dideoxystreptamines wherein the aminoglycoside radical at the 6-position is garosaminyl. Typical 5-epi-X-4-O-aminoglycosyl-6-O-garosaminyl-2,5-dideoxystreptamines of this invention are 5-epi-X-5-deoxygentamicin B, 5-epi-X-5-deoxygentamicin B$_1$, 5-epi-X-deoxygentamicin C$_1$, 5-epi-X-5-deoxygentamicin C$_{1a}$, 5-epi-X-5-deoxygentamicin C$_2$, 5-epi-X-5-deoxygentamicin C$_{2a}$, 5-epi-X-5-deoxygentamicin C$_{2b}$, 5-epi-X-5-deoxygentamicin X$_2$, 5-epi-X-5-deoxysisomicin, 5-epi-X-5-deoxyverdamicin, 5-epi-X-5-deoxy-Antibiotic G-418, 5-epi-X-5-deoxy-Antibiotic JI-20A, 5-epi-X-5-deoxy-Antibiotic JI-20B, 5-epi-X-5-deoxy-Antibiotic G-52 and the 1-N-alkyl derivatives thereof, which compounds are defined by the following structural formula I:

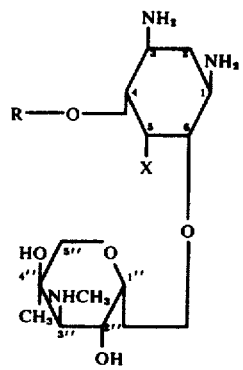

I and the 1-N-K-derivatives thereof, K being as hereinabove defined;

wherein X is as defined hereinabove, and wherein R is an aminoglycosyl function selected from the group consisting of:

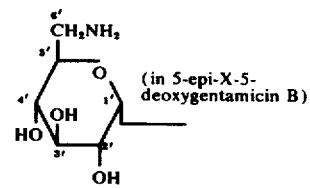
(in 5-epi-X-5-deoxygentamicin B)

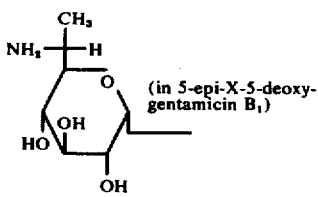
(in 5-epi-X-5-deoxygentamicin B$_1$)

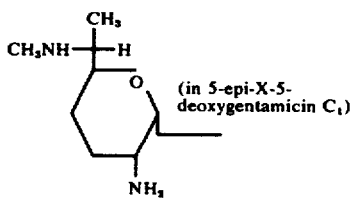
(in 5-epi-X-5-deoxygentamicin C$_1$)

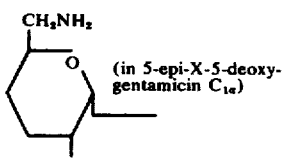
(in 5-epi-X-5-deoxygentamicin C$_{1a}$)

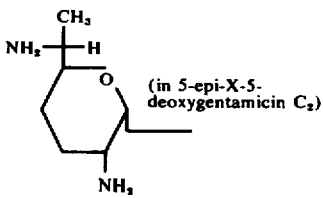
(in 5-epi-X-5-deoxygentamicin C$_2$)

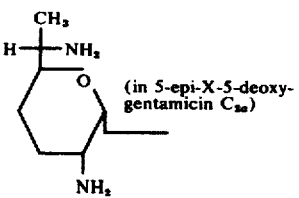
(in 5-epi-X-5-deoxygentamicin C$_{2a}$)

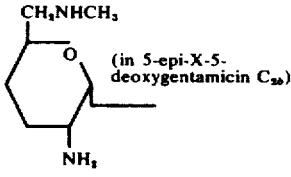
(in 5-epi-X-5-deoxygentamicin C$_{2b}$)

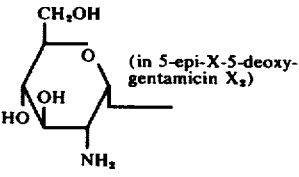
(in 5-epi-X-5-deoxygentamicin X$_2$)

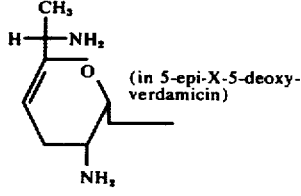
(in 5-epi-X-5-deoxyverdamicin)

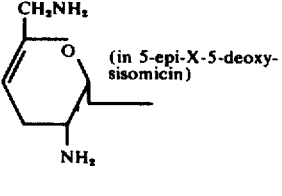
(in 5-epi-X-5-deoxysisomicin)

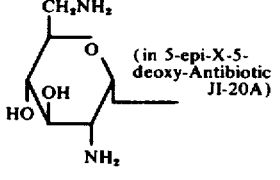
(in 5-epi-X-5-deoxy-Antibiotic JI-20A)

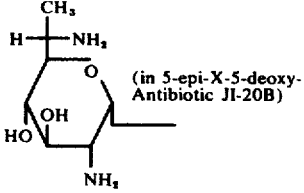
(in 5-epi-X-5-deoxy-Antibiotic JI-20B)

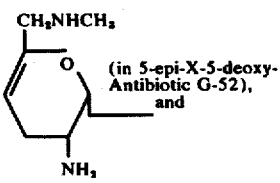 (in 5-epi-X-5-deoxy-Antibiotic G-52), and

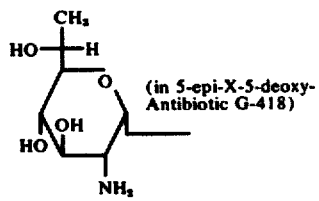 (in 5-epi-X-5-deoxy-Antibiotic G-418)

Other useful 5-epi-X-4,6-di-O-(aminoglycosyl)-2,5-dideoxystreptamines of this invention include 5-epi-X-5-deoxytobramycin, 5-epi-X-5-deoxykanamycin A, 5-epi-X-5-deoxykanamycin B, and 5-epi-X-5,3',4'-trideoxykanamycin B of following formula II:

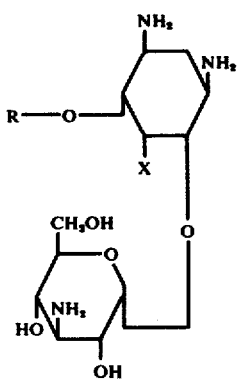

II and the 1-N-K derivatives thereof, K being as hereinabove defined;

wherein X is as hereinabove defined and R is an aminoglycosyl function selected from the group consisting of

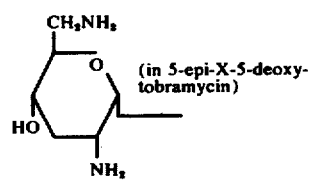 (in 5-epi-X-5-deoxytobramycin)

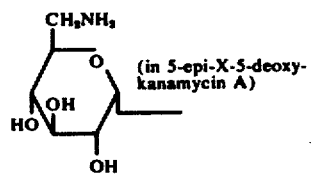 (in 5-epi-X-5-deoxykanamycin A)

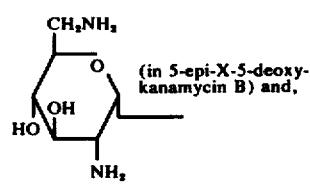 (in 5-epi-X-5-deoxykanamycin B) and,

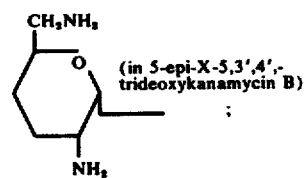 (in 5-epi-X-5,3',4'-trideoxykanamycin B);

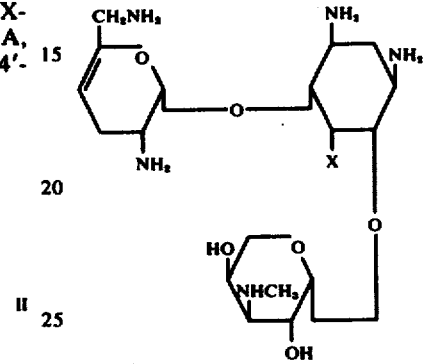

III and the 1-N-K derivatives thereof, K being as hereinabove defined; and wherein X is as above defined;

and 5-epi-X-5-deoxygentamicin A and 5-epi-X-5-deoxy-Antibiotic 66-40B of the following formula IV:

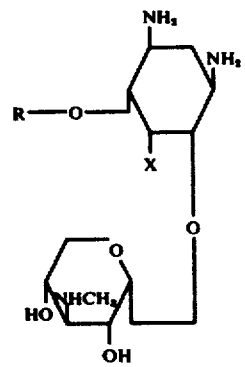

IV

5-Epi-X-5-deoxy-Antibiotic 66-40D of following formula III:

and the 1-N-K derivatives thereof, K being as hereinabove defined; and wherein X is as hereinabove defined and R is an aminoglycosyl function selected from the group consisting of

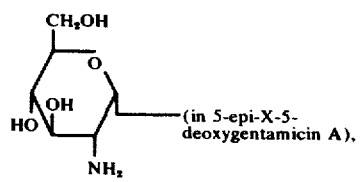

and

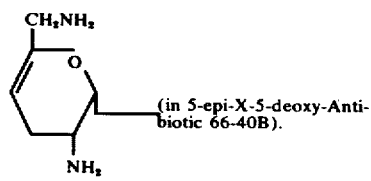

The 5-epi-X-4,6-di-O-(aminoglycosyl)-2,5-dideoxystreptamines of this invention as defined by formulae I, II, III, IV and their 1-N-alkyl derivatives are characterized by being white amorphous powders.

Also included within the composition-of-matter aspect of this invention are pharmaceutically acceptable acid addition salts of the 5-epi-X-4,6-di-O-(aminoglycosyl)-2,5-dideoxystreptamins such as defined by formulae I, II, III, IV and their 1-N-alkyl derivatives, which salts are made according to known procedures such as by neutralizing the free base with the appropriate acid, usually to about pH 5. Suitable acids for this purpose include acids such as hydrochloric, sulfuric, phosphoric, hydrobromic and the like. The physical embodiments of the acid addition salts of the 5-epi-X-4,6-di-O-(aminoglycosyl)-2,5-dideoxystreptamines and their 1-N-alkyl derivatives are characterized by being white solids which are soluble in water and insoluble in most polar and non-polar organic solvents.

The 5-epi-X-4,6-di-O-(aminoglycosyl)-2,5-dideoxystreptamines, such as defined by formulae I, II, III, IV and their 1-N-alkyl derivatives, particularly those wherein the 6-O-aminoglycosyl is 6-O-garosaminyl, and their non-toxic, pharmaceutically acceptable, acid addition salts, in general, exhibit broad spectrum antibacterial activity and possess an improved antibacterial spectrum compared to that of the parent antibiotics. In addition to this improved spectrum, the 5-epi-amino-5-deoxy derivatives advantageously also exhibit enhanced potency against organisms sensitive to the parent compound. Thus, for example, compounds of this invention, e.g. 5-epi-amino-4-O-aminoglycosyl-6-O-garosaminyl-2,5-dideoxystreptamines, are more active against organisms which inactivate the parent antibiotics by acetylation of the 3-amino group and/or by adenylylation of the 2''-hydroxyl group. Of these, some also exhibit anti-protozoal, anti-amoebic and anthelmintic properties. The 1-N-alkyl derivatives of this invention, particularly the 1-N-ethyl-5-epi-amino-4-O-aminoglycosyl-6-O-garosaminyl-2,5-dideoxystreptamines also exhibit improved antibacterial spectra as compared to their 1-N-unsubstituted percursors having the normal configuration at C-5.

Particularly valuable compounds of this invention are 5-epi-X-4-O-aminoglycosyl-6-O-garosaminyl-2,5-dideoxystreptamines of formula I and the 1-N-ethyl derivatives thereof, particularly the 5-epi-X-5-deoxy derivatives of gentamicin $C_1$, gentamicin $C_{1a}$, gentamicin $C_2$, gentamicin $C_{2a}$, gentamicin $C_{2b}$, sisomicin, verdamicin, Antibiotic G-52, as well as 5-epi-X-5-deoxy-Antibiotic 66-40D of formula III and the 1-N-ethyl derivatives thereof, which derivatives are broad spectrum antibacterial agents, being active against gram positive bacteria (e.g. *Staphylococcus aureus*) and gram negative bacteria (e.g. *Escherichia coli* and *Pseudomonas aeruginosa*) as determined by standard dilution tests, including bacteria resistant to the parent compounds.

Other composition-of-matter aspects of this invention include O and N-protected derivatives of the 5-epi-azido-4,6-di-O-(aminoglycosyl)-2,5-dideoxystreptamines of formulae I, II, III and IV wherein X is azido and wherein all hydroxyl functions and amino functions are protected by groups susceptible to reductive cleavage (such as by treatment with hydrogen in the presence of a catalyst or by treatment with an alkali metal in liquid ammonia) or to basic or mild acid hydrolysis (such as with aqueous sodium hydroxide or aqueous acetic acid), which compounds are useful as intermediates in preparing the antibacterially active 5-epi-amino-5-deoxy- and 5-epi-azido-5-deoxy-aminoglycosides of formulae I, II, III, IV and the 1-N-alkyl derivatives thereof.

Useful amino protecting groups (designated by "Y" in Formulae V to XII shown hereinbelow) for the intermediates of this invention include lower alkoxycarbonyls (preferably having up to 8 carbon atoms, e.g. methoxycarbonyl, ethoxycarbonyl, n-propyloxycarbonyl, iso-propyloxycarbonyl, n-butyloxycarbonyl, tert-butoxycarbonyl, octyloxycarbonyl and the like), substituted benzyloxycarbonyl (including o, m and p-methoxybenzyloxycarbonyl, and the like) and, preferably, benzyloxycarbonyl. Lower alkanoyls preferably having up to 8 carbon atoms (e.g. acetyl, propionyl, valeryl, caprylyl) are also useful amino protecting groups (Y), particularly for intermediates derived from antibacterials which cannot form a 3'',4''-N,O-carbonyl derivative (e.g. intermediates not having a 6O-garosaminyl substituent such as gentamicin A, and the kanamycins).

The foregoing amino protecting groups are removable by treatment with base (e.g. with sodium hydroxide) or, in the case of benzyloxycarbonyl, by reductive cleavage methods known in the art. Benzyloxycarbonyl is a preferred amino protecting group because it is removed under the reducing conditions of the process of this invention whereby a 5-epi-azido-5-deoxy-per-N-protected-per-O-protected intermediate is treated with hydrogen in the presence of a catalyst (preferably palladium) or with an alkali metal (e.g. sodium or potassium) in liquid ammonia to produce a 5-epi-amino-5-deoxyaminoglycoside of this invention. In addition to the foregoing, benzyloxycarbonyl is a preferred amino protecting group for the intermediates of this invention since, in aminoglycosides having a hydroxyl function adjacent an amino function, such as at positions 3'' and 4'' in the 6-O-garosaminyl radical of the aminoglycosides of formula I, the N-benzyloxycarbonyl derivative (e.g. the 3''-N-benzyloxycarbonyl derivatives of compounds of formula I) when subjected to basic conditions (such as with sodium hydride in dimethylformamide) forms an oxazolidinone with the adjacent hydroxyl function (e.g. a 3'',4''-N,O-carbonyl derivative of compounds of formula I) with concomitant elimination of benzyl alcohol. similarly, N-alkoxy carbonyl derivatives will form oxazolidinones with an adjacent hydroxyl function. Additionally, when a starting compound has a 1-N-alkyl (i.e. a 1-N-K) substituent which as a hydroxyl group alpha or beta to an amino protecting group, Y, which is a banzyloxycarbonyl or alkoxycarbonyl, the hydroxyl group together with said protecting group Y will form an oxazolidinone or a tetrahydro-1,3-oxazin-2-one, respectively.

Hydroxyl functions in the intermediates of this invention are conveniently protected by O-acyl radicals of hydrocarboncarboxylic acids preferably having up to 8 carbon atoms (said radicals being designated as "Z" in Formulae V to XII hereinbelow) or by O-hydrocarbonylidene radicals of ketones and aldehydes preferably having up to 8 carbon atoms to form ketals and acetals, respectively, including cyclic ketals and acetals (said hydrocarbonylidene radicals being designated as "W" in formulae V to XII hereinbelow).

In general, neighboring hydroxyl groups in the aminoglycoside precursors of the intermediates of this invention are conveniently protected by cyclic ketals or acetals. By "neighboring hydroxyl groups" are contemplated vicinal and non-vicinal hydroxyl groups which are situated so that together they form a cyclic ketal or cyclic acetal function with ketones and aldehydes or their derivatives, respectively. Exemplary of such neighboring hydroxyl groups are the 2',3'-hydroxyl groups in gentamicins B and $B_1$ and in kanamycin A (which form 2',3'-O-hydrocarbonylidene derivatives), the 4',6'-hydroxyl groups in gentamicins A and $X_2$ and in Antibiotic G-418 (which form 4',6'-O-hydrocarbonylidene derivatives, the 3',4'-hydroxyl groups in Antibiotics JI-20A and JI-20B and in kanamycin B (which form 3',4'-O-hydrocarbonylidene derivatives) and the 4'',6''hydroxyl groups in tobramycin, kanamycins A and B, and 3',4'-dideoxykanamycin B (which form 4'',6''-O-hydrocarbonylidene derivatives).

The cyclic ketal and acetal derivatives of said neighboring hydroxyl groups of this invention include O-alkylidene (e.g. O-iso-propylidene), O-cycloalkylidene (e.g. O-cyclohexylidene), and O-arylakylidene (e.g. O-benzylidene) derivatives, all of which are removable upon treatment with dilute aqueous mild acid (e.g. by 50 to 80% acetic acid). The nature of the hydrocarbon or substituted hydrocarbon "ylidene" radicals of the cyclic ketals and acetals is immaterial since they act only as "blocking groups", do not enter into the process of the invention, and are subsequently removed so that the free hydroxyls are regenerated in their original form.

In the 5-epi-azido-5-deoxy-per-N-protected-per-O-protected intermediates of this invention, isolated hydroxyl groups other than the 5-hydroxyl group such as the 2''-hydroxy present in all the aminoglycoside precursors of this invention, the 4'-hydroxy in tobramycin, and the 4''-hydroxy in Antibiotic 66-40B and in gentamicin A as well as other hydroxyl groups which are not protected by cyclic ketal or acetal functions (e.g. the 3'-hydroxy in gentamicin A and the 2' and 4'-hydroxyl in kanamycin A) are conveniently protected by hydrocarboncarbonyl radicals (designated as "Z" in formulae V to XII hereinbelow), said hydrocarbon preferably having up to 8 carbon atoms. Useful hydrocarbon-carbonyl radicals are acyl radicals derived from lower alkanoic acids having up to 8 carbon atoms including acetyl, propionyl, n-butyryl, valeryl, and caprylyl, as well as acyl radicals derived from aralkanoic acids such as phenylacetyl and from arylcarboxylic acids such as o, m and p-toluoyl, mesitoyl, and preferably benzoyl.

Included among the 5-epi-azido-5-deoxy-per-N-protected-per-O-protected intermediates of this invention are 1,3,2',6''-tetra-N-Y-5-epi-azido-5-deoxy-2''-O-Z-3'',4''-N,O-carbonyl-Antibiotic 66-40D of the following formula V:

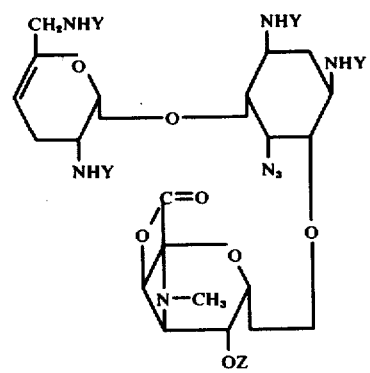

and the 1-N-K''derivatives thereof wherein K'' is as defined hereinabove for K but wherein any amino function is substituted by groups Y, and any hydroxy function is converted to an ester OZ, or, when said hydroxyl group is alpha or beta to an amino protecting group Y which is benzyloxycarbonyl or alkoxycarbonyl, the hydroxyl group together with said protecting group y is converted to an oxazolidinone or a tetrahydro-1,3-oxazin -2-one, respectively, Y and Z being as defined hereinbelow: and 1,3,2',6'-tetra-N-Y-5-epi-azido-2''-O-Z-3'',4''-N,O-carbonyl-4,6-di-O-(aminoglycosyl)-2,5-dideoxystreptamines of following formula VI:

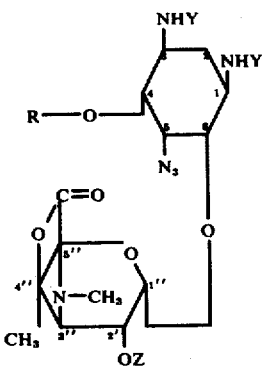

and the 1-N-K'' derivatives thereof wherein K'' is as hereinabove defined; and wherein Y is a member selected from the group consisting of benzyloxycarbonyl, substituted benzyloxycarbonyl, and alkoxycarbonyl, and Z is a hydrocarboncarbonyl, said hydrocarbon having up to 8 carbon atoms; and R is an aminoglycosyl function selected from the group consisting of:

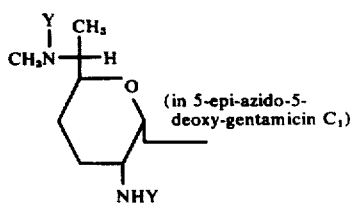 (in 5-epi-azido-5-deoxy-gentamicin C₁)

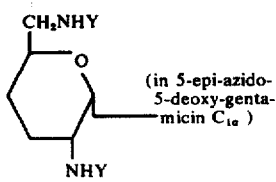 (in 5-epi-azido-5-deoxy-gentamicin C₁ₐ)

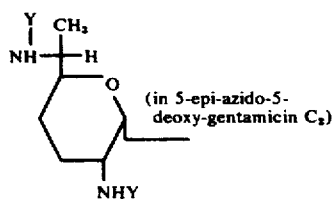 (in 5-epi-azido-5-deoxy-gentamicin C₂)

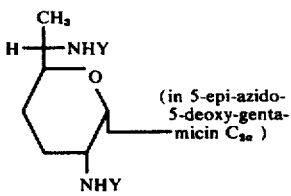 (in 5-epi-azido-5-deoxy-gentamicin C₂ₐ)

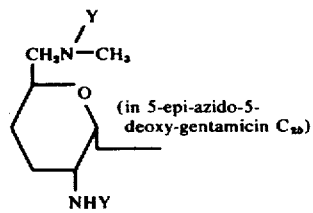 (in 5-epi-azido-5-deoxy-gentamicin C₂ᵦ)

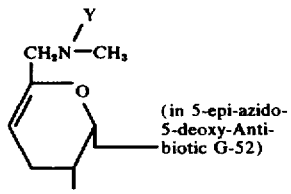 (in 5-epi-azido-5-deoxy-Antibiotic G-52)

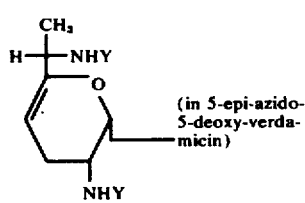 (in 5-epi-azido-5-deoxy-verdamicin)

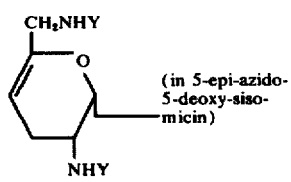 (in 5-epi-azido-5-deoxy-sisomicin)

wherein Y is as hereinabove defined.

Other 5-epi-azido-5-deoxy-per-N-protected-per-O-protected intermediates of this invention include 1,3,2′,6′,3″-penta-N-Y′-5-epi-azido-5-deoxy-4′,2″-di-O-Z-4″,6″-O-W-tobramycin, 1,3,6′,3″-tetra-N-Y′-5-epi-azido-5-deoxy-2′,2″-O-Z-3′,4′,4″,6″-di-O-W-kanamycin A, 1,3,6′,3″-tetra-N-Y′-5-epi-azido-5-deoxy-4′,2″-di-O-Z-2′,3′;4″,6″-di-O-W-kanamycin A, 1,3,2′,6′,3″-penta-N-Y′-5-epi-azido-5-deoxy-3′,4′;-4″,6″-di-O-Z-kanamycin B and 1,3,2′,6′,3″-penta-N-Y′-5-epi-azido-5-deoxy-2″-O-Z-4″,6″-O-W-3′,4′-dideoxykanamycin B of formula VII:

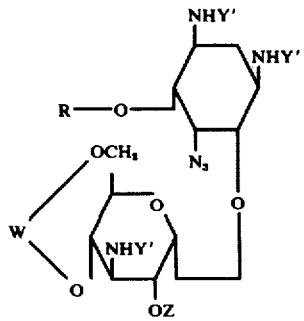 VII and the 1-N-K″ derivatives thereof, K″ being as hereinabove defined; and wherein W is a hydrocarbonylidene having up to 8 carbon atoms selected from the group consisting of alkylidene, cycloalkylidene and arylalkylidene;

Y′ is lower alkanoyl, benzyloxycarbonyl, substituted benzyloxycarbonyl or alkoxycarbonyl;

Z is as defined for formulae V and VI, and R is a member selected from the group consisting of:

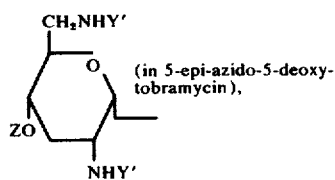 (in 5-epi-azido-5-deoxy-tobramycin),

-continued

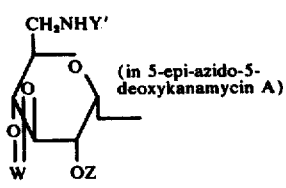 (in 5-epi-azido-5-deoxykanamycin A)

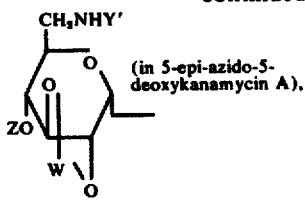 (in 5-epi-azido-5-deoxykanamycin A),

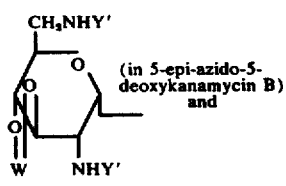 (in 5-epi-azido-5-deoxykanamycin B) and

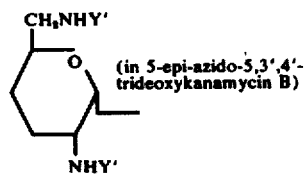 (in 5-epi-azido-5,3',4'-trideoxykanamycin B)

wherein W, Y' and Z are as hereinabove defined;
1,3-di-N-Y-5-epi-azido-5-deoxy-2',3'-O-W-6',4';3'λ',4''-di-N,O-carbonyl-2''-O-Z-derivatives of gentamicins B and B₁ of following formula VIII:

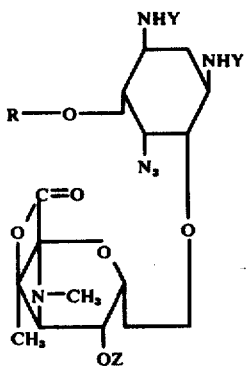

VIII and the 1-N-K'' derivatives thereof, K'' being as hereinabove defined; and
wherein Y and Z are as hereinabove defined, and R is an aminoglycosyl function selected from the group consisting of:

1,3,2'-tri-N-Y-5-epi-azido-5-deoxy-3',2''-di-O-Z-4',6'-O-W-3'',4''-N,O-carbonyl derivatives of gentamicin X₂ and Antibiotic G-418 of following formula IX:

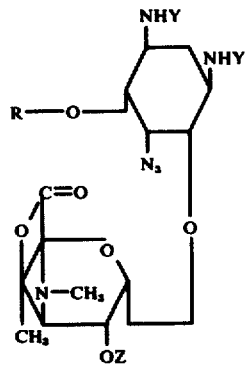

IX and the 1-N-K'' derivatives thereof, K'' being as hereinabove defined; and
wherein Y and Z are as hereinabove defined and R is an aminoglycosyl function selected from the group consisting of:

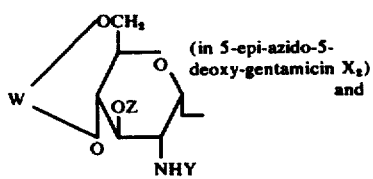 (in 5-epi-azido-5-deoxy-gentamicin X₂) and

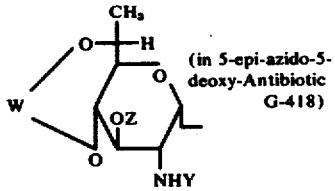 (in 5-epi-azido-5-deoxy-Antibiotic G-418)

consisting of:

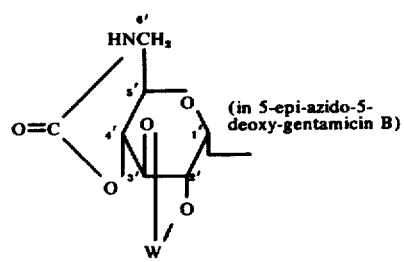 (in 5-epi-azido-5-deoxy-gentamicin B)

W being as hereinabove defined;

W, Y and Z being as hereinabove defined; 1,3,2',6',-

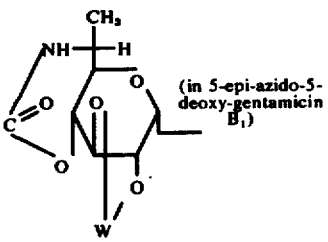 (in 5-epi-azido-5-deoxy-gentamicin B₁)

3''-penta-N-Y'-5-epi-azido-5-deoxy-2'',4''-di-O-Z-Antibiotic 66-40B of following formula X:

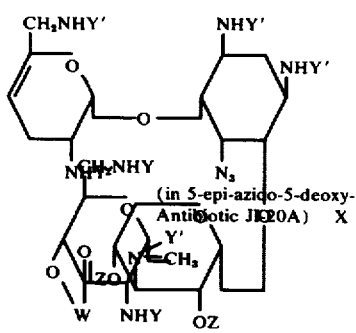

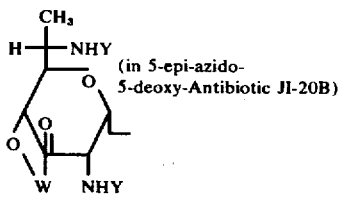

and the 1-N-K" derivatives thereof, K" being as hereinabove defined; and wherein Y' and Z are as hereinabove defined; 1,3,2',3"-tetra-N-Y'-5-epi-azido-5-deoxy-3',2",4"'-tri-O-Z-4',6'-O-W-gentamicin A of following formula XI:

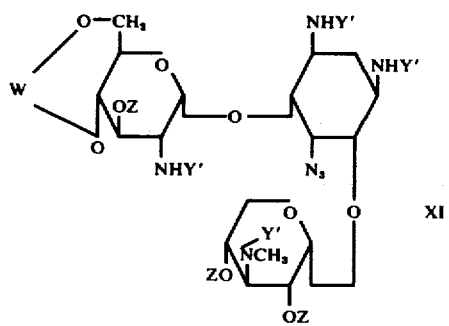

and the 1-N-K" derivatives thereof, K" being as hereinabove defined; and wherein W, Y' and Z are as hereinabove defined; and 1,3,2',6'-tetra-N-Y-5-epi-azido-5-deoxy-3',4'-O-W-2"-O-Z-3",4"'-N,O-carbonyl derivatives of Antibiotics JI-20A and JI-20B of following formula XII:

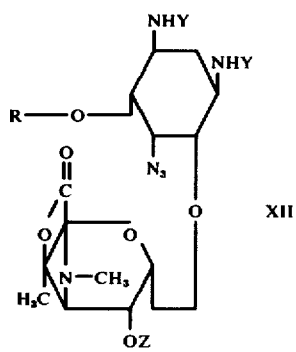

and the 1-N-K" derivatives thereof, wherein K" is as hereinabove defined; and wherein Y and Z are as hereinabove defined and R is an aminoglycosyl function selected from the group consisting of:

The 5-epi- azido-per-N-protected-O-protected-4,6-di-O-aminoglycosyl)-2,5-dideoxystreptamine intermediates of this invention as defined by formula V - XII and their 1-N-alkyl derivatives are characterized by being white solids. Their preparation is described in the general description of the process aspect of this invention set forth hereinbelow.

GENERAL DESCRIPTION OF THE PROCESS ASPECTS OF THE INVENTION

In one process of this invention, the antibacterially active 5-epi-amino- 4,6-di-O-(aminoglycosyl)-2,5-dideoxystreptamines of this invention, e.g. as defined by formulae I, II, III, IV and the 1-N-alkyl derivatives thereof, are prepared by the reaction of the corresponding 5-epi-azido-per-N-protected-per-O-protected-4,6-di-O-(aminoglycosyl)-2,5-dideoxystreptamine, e.g. as defined by formulae V - XII and their 1-N-alkyl derivatives with a reducing agent selected from the group consisting of hydrogen in the presence of a catalyst or with an alkali metal in liquid ammonia, followed by the cleavage of any remaining amino or hydroxyl protecting groups in the thereby formed 5-epi-amino-4,6-di-O-(aminoglycosyl)-2,5-dideoxystreptamine derivative by the reaction thereof under basic, and, when acetals or ketals are present, also under mild acid hydrolytic conditions.

Reduction with hydrogen in the presence of a catalyst is preferred when reducing 5-epi-azido-4,6-di-O-(aminoglycosyl)-2,5-dideoxystreptamine-N-protected-O-protected intermediates devoid of unsaturation such as the 5-epi-azido-5-deoxy-O-and N-protected derivatives of gentamicins A, B, $B_1$, $C_1$, $C_{1a}$, $C_2$, $C_{2a}$, $C_{2b}$, and $X_2$, of tobramycin, kanamycins A and B, 3',4'-dideoxykanamycin B, and Antibiotics G-418, JI-20A, JI-20B and their 1-N-alkyl derivatives. On the other hand, when reducing 5-epi-azido-N-protected-O-protected-4,6-di-O-(aminoglycosyl)-2,5-dideoxystreptamine intermediates of this invention in which double bonds are present, such as in sisomicin, verdamicin, Antibiotic G-52, and in Antibiotics 66-40B, 66-40D and their 1-N-alkyl derivatives, reduction by means of an alkali metal in liquid ammonia is preferable in order to avoid reduction of the double bond.

When reducing a 5-epi-azido-5-deoxy-intermediate with hydrogen in the presence of a catalyst, the catalysts most frequently employed are platinum, palladium, and, preferably palladium on charcoal.

The hydrogenation is usually carried out at room temperatures in lower alkanoic acids, preferably acetic acid, although other solvents such as lower alkanol may be used. The hydrogenation is continued until there is no further discernible drop in hydrogen pressure and the 5-epi-amino-5-deoxy derivative thereby formed is usually isolated by removing the solvent such as by distillation, and thence treating the 5-epi-amino- 5-deoxy residue thereby formed with base and acid, if necessary, to remove any remaining N-protecting and O-protecting groups. Whey my procss is carried out with 5-epi-azido-5-deoxy intermediates having per-N-benzyloxycarbonyl amino protecting groups and 3'',-4''-N,O-carbonyl-protecting groups such as in the intermediates of formulae V and VI, the benzyloxycarbonyl protecting groups are advantageously removed during the hydrogenation procedure and the resulting 5-epi-amino-5-deoxy-2''-O-hydrocarboncarbonyl 3'',-4''-N,O-carbonyl derivative need only be treated with base (e.g. with 2 N sodium hydroxide) to remove the acyl radicals. The resulting antibacterially active 5-epi-amino- 5-deoxyaminoglycoside is then isolated and purified utilizing known techniques. Thus, in a typical mode of carrying out the hydrogenation of a 5-epi-azido-5-deoxy per-N-protected-per-O-protected intermediate of formulae V and VI, the 5-epi-azido-5-deoxy intermediate (e.g. 1,3,2',6'-tetra-N-benzyloxycarbonyl-5-epi-azido-5-deoxy- 2''-O-benzoyl-3'',4''-N,O-carbonylgentamicin $C_{1a}$), dissolved in acetic acid, is hydrogenated at room temperature at 60 pounds per square inch (psi) starting hydrogen pressure in the presence of 30% palladium on charcoal catalyst. When no further drop in hydrogen pressure is discernible, the catalyst is removed by filtration, and the solvent removed by distillation in vacuo to produce a residue comprising 5-epi-amino-5-deoxy-2''-O-benzoyl-3'',4''-N,O-carbonylgentamicin $C_{1a}$ which, upon treatment with 2 N sodium hydroxide at elevated temperatures (e.g. 100° C) followed by neutralization with acetic acid, removal of any insolubles by filtration, concentration of the reaction solution to a small volume and thence chromatography thereof on Amberlite IRC-50 resin ($H^+$ form), followed by elution with ammonium hydroxide, concentration and lyophilization of the eluate gives 5-epi-amino-5-deoxygentamicin $C_{1a}$, a novel antibacterial agent of this invention.

Any acetal or ketal protecting groups in the starting 5-epi-azido-5-deoxy-per-N-protected-per-O-protected aminoglycoside may be removed after hydrogenation and treatment of the product thereby formed with base, by treatment with mild aqueous acid, e.g. with dilute mineral acids, or with trifluoroacetic acid, or usually with dilute alkanoic acids such as acetic acid, to remove the ketal or actal protecting groups.

When reducing a 5-epi-azido-5-deoxy-per-N-protected-per-O-protected aminoglycoside having a double bond by reaction thereof with an alkali metal (e.g. potassium, lithium and, preferably, sodium) in liquid ammonia, the 5-epi-azido-5-deoxy-intermediate (e.g. 1,3,2'6'-terta-N-benzyloxycarbonyl-5-epi-azido-5-deoxy-2''-O-benzoyl-3'',4''-N,O-carbonylsisomicin) is usually dissolved in a mixture of a cosolvent such as tetrahydrofuran and liquid ammonia to which the alkali metal (e.g. sodium) is added slowly and the reaction mixture stirred for a few hours. Th ammonia is allowed to evaporate and any remaining O and N-protecting groups are removed by addition of water to the reaction mixture affording sodium hydroxide and heating at elevated temperatures (e.g. 100° C). Purification of the resulting product is usually carried out via chromatographic techniques to obtain an antibacterially active 5-epi-amino-5-deoxy-aminoglycoside of this invention, e.g. 5-epi-amino-5-deoxysisomicin.

In another process aspect of this invention, the antibacterially active 5-azido-4,6-di-O-(aminoglycosyl)-2,5-dideoxystreptamines of formulae I, II, III and IV (wherein X is azido) and the 1-N-alkyl derivatives thereof, are prepared from the corresponding 5-epi-azido-5-deoxy-per-N-protected-per-O-protected intermediates wherein said N- and O-protecting groups are susceptible to cleavage by basic or mild acid hydrolysis, such as the 5-eip-azido-5-deoxy derivatives of formulae V – XII and their 1-N-alkyl derivatives, by treatment thereof at elevated temperatures with aqueous base and, when acetals or ketals are present, by treatment also with aqueous mild acid.

Thus, in a 5-epi-azido-5-deoxy intermediate wherein all the O- and N-protecting groups are susceptible to cleavage by base (e.g. as in 1,3,2',6'-tetra-N-benzyloxycarbonyl-5-epi-azido-5-deoxy-2''-O-benzoyl-3'',4''-N,O-carbonylsisomicin) treatment thereof at 100° C with aqueous sodium hydroxide will produce an antibacterially active 5-epi-azido-5-deoxyaminoglycoside of this invention (e.g. 5-epi-azido-5-deoxysisomicin). When the 5-epi-azido-5-deoxy-per-N-and O-protected intermediates also contain acetal and ketal functions which are cleaved by acid (e.g. as in 1,3,2',6'-tetra-N-benzyloxycarbonyl-5-epi-azido-5-deoxy-3',4'-O-benzylidene-2''-O-benzoyl-3'',4''-N,O-carbonyl-Antibiotic JI-20A), after treatment with base as described hereinabove, the resultant product is treated with mild aqueous acid followed by neutralization of said aqueous acid mixture with mild base (e.g. aqueous ammonium hydroxide). Purification of the resulting product by known techniques, usually by chromatography, yields an antibacterially active 5-epi-azido-5-deoxy aminoglycoside antibacterial agent of this invention, e.g. 5-epi-azido-5-deoxy-Antibiotic JI-20A).

The requisite, novel intermediates for the foregoing process aspects of my invention, i.e. the 5-epi-azido-4,6-di-O-(aminoglycosyl)-2,5-dideoxystreptamines having hydroxyl and amino protecting groups susceptible to reductive cleavage or to basic or mild acid hydrolysis, such as defined by above formulae V – XII and the 1-N-alkyl derivatives thereof, are prepared by another process aspect of this invention whereby the corresponding 5-O-hydrocarbonsulfonyl (or substituted hydrocarbonsulfonyl)-4,6-di-O-(aminoglycosyl)-2-deoxystreptamine (i.e. compounds of formulae V – XII and their 1-N-alkyl derivatives devoid of the 5-epi-azido moiety and having a 5-O-hydrocarbonsulfonyl group) is treated with an alkali metal azide in an organic solvent.

Organic solvents suitable for my process are organic solvents in which the 5-O-hydrocarbonsulfonyl (or substituted hydrocarbonsulfonyl)-per-N-protected-per-O-protected 4,6-di-O-(aminoglycosyl)-2-deoxystreptamine and the alkali metal azide reagent are soluble and are solvents which will not react with the reagent so that the possibility of competing side reactions are minimized. Suitable organic solvents most useful in this process are solvents such as dimethylformamide, dimethylacetamide and hexamethylphosphorictriamide. Dimethylformamide is frequently conveniently used.

Sodium azide is usually employed when converting a 5-O-hydrocarbonsulfonyl intermediate of this invention to the corresponding 5-epi-azido-5-deoxy intermediate of formulae V – XII and their 1-N-alkyl derivatives; however, other alkali metal azides may be used, such as potassium azide and lithium azide.

The 5-O-hydrocarbonsulfonyl and 5-O-substituted hydrocarbonsulfonyl ester intermediates useful in this process are those derived from hydrocarbonsulfonic acids having up to 8 carbon atoms including ethanesulfonic acid, benzenesulfonic acid, p-toluenesulfonic acid, and preferably, methanesulfonic acid; also those derived from nitrobenzene sulfonic acids (e.g. o, m, and p-nitrobenzene sulfonic acids) and those derived from halogenohydrocarbonsulfonic acids (e.g. trifluoromethanesulfonic acid, p-chlorobenzenesulfonic acid, o or p-bromobenzenesulfonic acids and the like). Th 5-O-hydrocarbonsulfonyl and 5-O-substituted hydrocarbonsulfonyl intermediates are prepared from the corresponding per-N-protected-per-O-protected-5-hydroxyaminoglycosides (i.e. compounds of formulae V – XII and their 1-N-alkyl derivatives devoid of the 5-epi-X-moiety and having a 5-hydroxyl function) by treatment thereof with a hydrocarbonsulfonyl halide (preferably methanesulfonylchloride in a tertiary amine (usually triethylamine)).

When converting a 5-O-hydrocarbonsulfonyl (or 5-O-substituted hydrocarbonsulfonyl)-4,6-di-O-(aminoglycosyl)-2-deoxystreptamine (having amino functions and all other hydroxyl functions protected by groups susceptible to reductive cleavage and/or to basic or mild acid hydrolysis) to the corresponding 5-epi-azido-5-deoxy intermediate (such as defined by formulae V – XII and the 1-N-alkyl derivatives thereof) by my process, the starting 5-O-hydrocarbonsulfonyl derivative (e.g. 1,3,2',6'-tetra-N-benzyloxycarbonyl-5-Q-methanesulfonyl-2''-O-benzoyl-3'',4''-N,O-carbonylsisomicin and 1,3,2',6'-tetra-N-benzyloxycarbonyl-5-O-methanesulfonyl-2''-O-benzoyl-3'',4''-N,O-carbonylgentamicin $C_1$) is usually dissolved in dimethylformamide to which at least an equivalent and usually an excessive molar quantity (with reference to the molar quantity of aminoglycoside) of sodium azide is added under an atmosphere of argon. The reaction mixture is heated (usually over 100° C) until the 5-O-methanesulfonyl intermediate is no longer present as evidenced by thin layer chromatographic analysis. The resulting product is isolated usually by concentrating the reaction mixture, dissolving the residue in an acid-free organic solvent, washing the organic solution with water, thence evaporating the washed organic solution to a residue comprising a 5-epi-azido-5-deoxy intermediate of formulae V – XII or a 1-N-alkyl derivative thereof (e.g. 1,3,2',6'-tetra-N-benzyloxycarbonyl-5-epi-azido-5-deoxy-2''-O-benzoyl-3'',4''-N,O-carbonylsisomicin and 1,3,2',6'-tetra-N-benzyloxycarbonyl-5-epi-azido-5-deoxy-2''-O-benzoyl-3'',4''-N,O-carbonylgentamicin $C_1$).

The per-N-protected-per-O-protected-5-O-hydrocarbon-sulfonyl-4,6-di-O-(aminoglycosyl)-2-deoxystreptamine precursors for the corresponding 5-epi-azido-5-deoxy intermediates, are derived from known, unprotected-4,6-di-O-(aminoglycosyl)-2-deoxystreptamines including 4-O-aminoglycosyl-6-O-garosaminyl-2-deoxystreptamine antibiotics such as gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, Antibiotic G-418, Antibiotic JI-20A, Antibiotic JI-20B, and Antibiotic G-52; and 4,6-di-O-(aminoglycosyl)-2-deoxystreptamines such as gentamicin A, tobramycin, Antibiotic 66-40B and Antibiotic 66-40D. Of the foregoing, preferred starting antibiotic precursors are gentamicins $C_1$, $C_{1a}$, $C_2$, $C_{2a}$, $C_{2b}$, antibiotic 66-40D, verdamicin, Antibiotic G-52, and sisomicin, all of which are most easily converted to preferred compounds of this invention, i.e. to the corresponding 5-epi-azido-5-deoxy and the 5-epi-amino-5-deoxy-derivatives.

The aforementioned 4,6-di-O-(aminoglycosyl)-2-deoxystreptamine antibiotics are known. Of the gentamicins, the starting compound referred to herein as gentamicin $X_2$ is also known in the art as gentamicin X. The starting compound referred to herein as gentamicin $C_{2a}$ is isolated and characterized as set forth herein in Preparation 1.

The starting compound referred to herein as gentamicin $C_{2b}$, isolated and characterized as set forth in Preparation 2, and having the structural formula shown herein, is named in some prior art as gentamicin $C_{2a}$.

When preparing the 1-N-K-5-epi-X-4,6-di-O-(aminoglycosyl)-2,5-dideoxystreptamines of this invention, the 1-N-K-per-N-protected-per-O-protected-5-O-hydrocarbonsulfonyl-4,6-di-O-(aminoglycosyl)-2-deoxystreptamine precursors are also derived from the 1-N-alkyl (i.e. the 1-N-K) derivatives of the aforedescribed 1-N-unsubstituted-4,6-di-O-(aminoglycosyl)-2-deoxystreptamines. The 1-N-K-aminoglycosides are known compounds being described in Belgian Pat. No. 818,431 and in co-pending application U.S. Ser. No. 492,998 filed July 30, 1974 of John J. Wright et al of common assignee as the instant application.

Included among the alkyl substituents contemplated for the moiety K in the starting compounds and in the novel 1-N-K-5-epi-X-4,6-di-O-(aminoglycosyl)-2,5-dideoxystreptamines of this invention are straight and branched chain alkyl groups such as ethyl, n-propyl, n-butyl, β-methylpropyl, n-pentyl, β-methylbutyl, γ-methylbutyl and β,β-dimethylpropyl: n-hexyl, δ-methylpentyl, β-ethylbutyl, γ-ethylbutyl, n-heptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; alkylcycloalkyl groups such as cyclopropylmethyl, cyclopentylmethyl, cyclohexylmethyl and cyclopentylethyl; alkenyl groups such as β-propenyl, β-methylpropenyl, β-butenyl, β-methyl-β-butenyl, β-ethyl-β-hexenyl: aralkyl groups such as benzyl, o-tolyl, m-tolyl, p-tolyl and phenylethyl; hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, ω-hydroxyoctyl: amino substituted straight and branched chain alkyl groups such as ε-aminopentyl, β-aminopropyl, γ-aminopropyl, δ-aminobutyl, β-amino-γ-methylbutyl and ω-aminoocyl and mono-N-alkylated derivatives thereof such as the N-methyl, N-ethyl, and N-propyl derivatives, e.g. ε-methylaminopentyl, β-methylaminopropyl, β-ethylaminopropyl, δ-methylaminobutyl, β-methylamino-γmethylbutyl, and ω-methylaminobutyl: amino and hydroxy disubstituted straight and branched chain alkyl groups such as β-hydroxy-ε-aminopentyl, γ-hydroxy-γ-methyl-δ-aminobutyl, β-hydroxy-δ-aminobutyl, β-hydroxy-γ-aminopropyl, and β-hydroxy-β-methyl-γ-aminopropyl: and mono-N-alkylated derivatives thereof such as β-hydroxy-ε-methylaminopentyl, γ-hydroxy-γ-methyl-δ-methylaminobutyl, β-hydroxy-δ-methylaminobutyl, β-hydroxy-γ-ethylaminopropyl, and β-hydroxy-β-methyl-γ-methyl aminopropyl.

Of the foregoing alkyl substituents contemplated for the moiety K, preferred are lower alkyl substituents having up to 4 carbon atoms especially those having 2 to 4 carbon atoms, particularly valuable derivatives being 1-N-ethyl- and 1-N-propyl-5-epi-4,6-di-O-(aminoglycosyl)-1,3-diaminocyclitols of this invention.

When preparing the per-N-protected-per-O-protected-5-O-hydrocarbonsulfonyl-4,6-di-O-(aminoglycosyl)-2-deoxystreptamine starting compounds for my process, the amino groups are protected first by formation of amides susceptible to reductive cleavage or basic hydrolysis. For the processes of this invention, I prefer to protect the amino groups by forming N-benzyloxycarbonyl derivatives thereof (e.g. 1,3,2',6',3"-penta-N-benzyloxycarbonyl-gentamicin $C_{1a}$ and 1,3,6',3"-tetra-N-benzyloxycarbonylgentamicin B).

The per-N-protected aminoglycosides thereby formed which have a garosaminyloxy radical at C-6 are treated with an alkali metal hydride, usually sodium hydride in dimethylformamide, whereby the 3"-N-hydrocarbonyloxycarbonyl protecting group is cyclized with the 4"-hydroxy-function to form an oxazolidinone derivative, i.e. a 3",4"-N,O-carbonyl derivative. In aminoglycosides wherein other amino groups are adjacent to a hydroxyl group (such as the 6'-amino and 4'-hydroxyl in gentamicin B), other N,O-carbonyl derivatives will be formed. Thus, upon reaction of each of 1,3,2',6',3"-penta-N-benzyloxycarbonylgentamicin $C_1$ and of 1,3,6',3"-tetra-N-benzyloxycarbonylgentamicin B with sodium hydride in dimethylformamide, there are formed oxazolidinone derivaties, i.e. 1,3,2',6'-tetra-N-benzyloxycarbonyl-3",4"-N,O-carbonylgentamicin $C_1$ and 1,3-di-N-benzyloxycarbonyl-6',4';3",4"-di-N,O-carbonylgentamicin B.

I usually next protect adjacent hydroxyl groups which will form a ketal or acetal group upon treatment with a ketone or aldehyde or derivative thereof in dimethylformamide in the presence of catalytic amounts of a strong acid such as p-toluenesulfonic acid utilizing known techniques. Thus, the aforenamed intermediate of gentamicin B, upon treatment with 1,1-dimethoxycyclohexane in dimethylformamide in the presence of p-toluenesulfonic acid, yields a ketal at the 2' and 3'-hydroxyls, i.e. 1,3-di-N-benzyloxycarbonyl-2',3'-O-cyclohexylidene-6',4';3",4"-di-N,O-carbonylgentamicin B. Finally, any isolated hydroxyl functions (except the 5-hydroxyl group) remaining in the partially protected aminoglycoside derivatives are converted to the corresponding hydrocarboncarbonyl derivatives by treatment thereof with an acid chloride of the hydrocarboncarboxylic acid in a tertiary amine (preferably pyridine), the molar quantity of acid halide reagent being based upon the number of hydroxyl groups to be esterified. If only one hydroxyl group other than the 5-hydroxy remains in the molecule (e.g. the 2"-hydroxy) an equivalent quantity of acid halide to the molar quantity of aminoglycoside is used; if two hydroxyl groups remain to be protected, two molar equivalents of acid halide are used per mole of aminoglycoside. Acyl halides of hydrocarboncarboxylic acids having up to 8 carbon atoms are preferentially used, including acid chlorides of lower alkanoic acids such as acetic, propionic, valeric and caprylic acids; of aralkanoic acids such as phenylacetic acid and arylcarboxylic aids such as toluic and, preferably benzoic acids. Thus, each of the aforenamed intermediates of gentamicins $C_1$ and B upon treatment with equimolar quantities of benzoylchloride in pyridine, yields the corresponding 2"-O-benzoyl derivative, i.e. 1,3,2',6'-tetra-N-benzyloxycarbonyl-2"-O-benzoyl-3",4"-N,O-carbonylgentamicin $C_1$ and 1,3-di-N-benzyloxycarbonyl-2',3'-O-cyclohexylidene-6',4';3",4"-di-N,O-carbonyl-2"-O-benzoylgentamicin B, both of which upon treatment with methanesulfonyl chloride in triethylamine yields the corresponding 5-O-methanesulfonyl derivatives, requisite starting compounds for the process of this invention.

Alternatively, after protecting the amino groups by means of N-benzyloxycarbonyl derivatives and hydroxyl groups adjacent to said protected amino groups via N,O-carbonyl derivatives, all other hydroxyl groups except the 5-hydroxyl group may be protected by conversion thereof to a hydrocarboncarbonyl group without first protecting neighboring hydroxyl groups by acetal or ketal groups. Thus, 1,3-di-N-benzyloxycarbonyl-6',4';3",4"-di-N,O-carbonylgentamicin B upon reaction with three molar equivalents of benzoyl chloride in pyridine, yields the corresponding 2',3',2"-tri-O-benzoate derivative which upon reaction with methanesulfonyl chloride in pyridine is converted to a starting compound of this invention, i.e. 1,3-di-N-benzyloxycarbonyl-5-O-methanesulfonyl-2',3',2"-tri-O-benzoyl-6',4';3",4"-di-N,O-carbonylgentamicin B.

It is apparent from the foregoing that, by my invention, known 4,6-di-O-(aminoglycosyl)-2-deoxystreptamine antibacterial agents and their 1-N-alkyl derivatives are converted to the corresponding N-protected-O-protected-4,6-di-O-(aminoglycosyl)-2-deoxystreptamine having a free 5-hydroxyl group which, in turn, is converted to the corresponding 5-O-hydrocarbonsulfonyl derivative. Treatment of the 5-O-hydrocarbonsulfonyl derivative with an alkali metal azide in a suitable organic solvent yields a novel 5-epi-azido-N-protected-per-O-protected-4,6-di-O-(aminoglycosyl)-2,5-dideoxystreptamine of formulae V – XII and the 1-N-K" derivative thereof. Treatment of the foregoing at elevated temperatures with aqueous base and, when acetals or ketals are present, also with aqueous mild acid, yields the antibacterially active 5-epi-azido-4,6-di-O-(aminoglycosyl)-2,5-dideoxystreptamines of formulae I – IV or a 1-N-alkyl derivative thereof. Alternatively, treatment of the 5-epi-azido-5-deoxy derivatives of formulae V – XII or a 1-N-K" derivative thereof with a reducing agent selected from the group consisting of hydrogen in the presence of a catalyst and an alkali metal in liquid ammonia folloed by treatment of the product thereby formed with aqueous base at elevated temperatures, and optionally, with aqueous acid yields the antibacterially active 5-epi-amino-4,6-di-O-(aminoglycosyl)-2,5-dideoxystreptamines of formulae I – IV and their 1-N-alkyl derivatives.

OTHER METHODS OF PREPARING 1-N-ALKYL-5-EPI-X-4,6-DI-O-(AMINOGLYCOSYL)-2,5-DIDEOXYSTREPTAMINES

In addition to the foregoing processes of this invention, the 1-N-K-5-epi-X-4,6-di-O-(aminoglycosyl)-2,5-dideoxystreptamines of this invention may be prepared from the corresponding 1-N-unsubstituted-5-epi-X-4,6-di-O-(aminoglycosyl)-2,5-dideoxystreptamine via methods similar to those described in Belgian Pat. No. 818,431 and in co-pending application U.S. Ser. No. 492,988 filed July 30, 1974 of John J. Wright et al of common assignee as the instant application.

In one of these processes, the 1-N-K derivatives of the 5-epi-X-4,6-di-O-(aminoglycosyl)-2,5-dideoxystreptamines of formulae I, II, III and IV are prepared by treating an acid addition salt of the corresponding 1-N-unsubstituted-5-epi-X-4,6-di-O-(aminoglycosyl)-2,5-dideoxystreptamine antibacterial agent with about one molar equivalent of a hydride-donor reducing agent in an inert solvent (preferably a protic solvent in the presence of water) and in the presence of at least one molar equivalent of an aldehyde having the formula K'CHO wherein K' is a member selected from the group consisting of hydrogen and an alkyl substituent selected from the group consisting of alkyl, alkenyl, cycloalkyl, aralkyl, hydroxyalkyl, aminoalkyl, alkylaminoalkyl, aminohydroxyalkyl, and alkylainohydroxyalkyl, said alkyl substituent having up to 7 carbon atoms, and, when said alkyl substituent is substituted by both hydroxyl and amino functions, only one of sid functions can be attached to any one carbon atom, and wherein any amino function in said alkyl substituent is preferably protected with an acyl group.

This process, whereby the 1-amino function in an acid addition salt of a 1-N-unsubstituted -5-epi-X-4,6-di-O-(aminoglycosyl)-2,5-dideoxystreptamine antibacterial agent is selectively condensed with an aldehyde and concomitantly reduced in situ to form a 1-N-alkyl-5-epi-X-4,6-di-O-(aminoglycosyl)-2,5-dideoxystreptamine antibacterial agent, is usually carried out at room temperature in the presence of air, although it may be advantageously carried out under an inert atmosphere (e.g. argon or nitrogen).

Hydride-donor reducing agents include dialkylaminoboranes (e.g. dimethylaminoborane, diethylaminoborane and preferably morpholinoborane), tetraalkylammonium cyanoborohydride (e.g. tetrabutylammonium cyanoborohydride), alkali metal borohydride (e.g. sodium borohydride) and preferably, alkali metal cyanoborohydride (e.g. lithium cyanoborohydride and sodium cyanoborohydride).

This process is conveniently carried out at ambient temperatures in an inert solvent. By "inert solvent" is meant ay organic or inorganic solvent in which the 5-epi-X-4,6-di-O-(aminoglycosyl)-2,5-dideoxystreptamine starting compounds and the reagents are soluble, and which will not interfere with the process under the reaction conditions thereof so there are produced a minimum of competing side reactions. Although anhydrous aprotic solvents may sometimes advantageously be employed in this process (such as tetrahydrofuran when utilizing morpholinoborane as hydride-donor reducing agent) this process is usually carried out in protic solvent, e.g. in a lower alkanol or, preferably, in water or in an aqueous lower alkanol (e.g. aqueous methanol, aqueous ethanol), although other water-miscible co-solvent systems may be employed such as aqueous dimethylformamide, aqueous hexamethylphosphoramide, aqueous tetrahydrofuran and aqueous ethylene glycol dimethyl ether.

The acid addition salts of the 1-N-unsubstituted-5-epi-X-4,6-di-O-(aminoglycosyl)-2,5-dideoxystreptamines, requisite starting compounds, may be derived from any organic acid such as acetic acid, trifluoroacetic acid, or p-toluenesulfonic acid or from any inorganic acid such as hydrochloric acid, sulfuric acid, phosphoric acid, or nitric acid. It is usually most convenient to use the addition salts derived from sulfuric acid. Optimum results are achieved when all amino groups present in the molecule are fully neutralized; however, this process may be carried out using 5-epi-X-4,6-di-O-(aminoglycosyl)-2,5-dideoxystreptamine acid addition salts which are not fully protonated, or, alternatively, on fully protonated compounds in the presence of excess acid. It is usually convenient to prepare the requisite acid addition salt starting compound in situ by adding the desired acid (e.g. sulfuric acid) to a solution or suspension of the 5-epi-X-4,6-di-O-(aminoglycosyl)2,5-dideoxystreptamine (e.g. 5-epi-amino-5-deoxysisomicin) in a protic solvent (e.g. water) until the pH of the solution is in the range of from about 2 to 5, preferably from about 2.5 to about pH 3.5. This proceeds best within this range, but may be carried out at pH values in the range of from about pH 1 to about pH 11.

The starting acid addition salts of this process can be derived from any 3-epi-X-4,6di-O-(aminoglycosyl)-2,5-dideoxystreptamine which has a free amino group at the 1-position and which exhibits antibacterial activity against gram positive and/or gram negative organisms as determined by conventional in vitro techniques such as broth dilution tests, agar dilution tests, disc diffusion tests, and the like. A 5-epi-X-4,6-di-O-(aminoglycosyl)-2,5-dideoxystreptamine which inhibits bacteria at concentrations equal to or less than about 50 to about 100 mcg./ml. is considered to be an antibacterial agent.

Typical aldehydes of the formula K'CHO wherein K' is as above defined which are useful in this process include straight and branched chain alkyl aldehydes such as formaldehyde, acetaldehyde, n-propanol, n-butanal, 2-methylpropanal, n-pentanal, 2-methylbutanal, 3-methylbutanal, 2,2-dimethylpropanal, n-hexenal, 2-ethylbutanal, n-heptanal, and n-octanal; cycloalkylaldehydes such as cyclopropanecarboxaldehyde, cyclopentanecarboxaldehyde, cyclopentaneacetaldehyde, and cyclohexanecarboxaldehyde; alkenyl aldehydes such as propenal, 2-methylpropenal, 2-butenal, 2-methyl-2-butenal, 2-ethyl-2-hexenal; aralkyl aldehydes such as benzaldehyde, o, m, and p-tolualdehydes and phenylacetaldehyde; hydroxy substituted straight and branched chain alkyl aldehydes such as 5-hydroxypentanal, 2-hydroxy-3-methylbutanal, 2-hydroxy-2-methylpropanal, 4-hydroxybutenal, 2-hydroxypropanal and 8-hydroxyoctanal; amino substituted straight and branched chain alkyl aldehydes such as 5-aminopentanal, 2-aminopropanal, 3-aminopropanal, 4-aminobutanal, 2-amino-3-methylbutanal, 8-aminooctanal and mono-N-alkyl derivatives thereof; and amino and hydroxy disubstituted straight and branched chain alkyl aldehydes such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal, 2-amino-3-hydroxyoctanal, and mono-N-alkyl derivatives thereof.

In this process, if the aldehyde possesses a chiral center, one can use each enantiomer separately or together as a racemate and there will be obtained the respective diastereoisomers or a mixture thereof, respectively.

The aldehyde reagents useful in this process are either known compounds or are easily prepared from known compounds utilizing procedures well known in the art. Thus, for example, alkylaldehydes substituted by both hydroxyl and amino functions (e.g. 2-hydroxy-5-aminopentanal) may be prepared from an aminoaldehyde acetal (e.g. 4-aminobutanal diethylacetal) by protecting the amino function therein as an acetamido or phthalimido group utilizing known procedures followed by removal of the acetal function by acid hydrolysis thereby obtaining an N-protected aminoaldehyde (e.g. by converting 4-aminobutanal diethylacetal to the corresponding N-phthalimido derivative which upon acid hydrolysis yields 4-phthalimidobutanal). Treatment of the N-protected aminoaldehyde with hydrocyanic acid yields the corresponding N-protected-aminoalkyl hydroxynitrile (e.g. 2-hydroxy-5-phthalimidovaleronitrile) which upon catalytic reduction (e.g. hydrogen in the presence of palladium) or by hydride reduction (e.g. with diisobutylaluminum hydride) yields an N-protected amino-hydroxy aldehyde (e.g. 2-hydroxy-5-phthalimido-pentanal) which is an aldehyde reagent used in this process.

When carrying out this process, in order to minimize competing side reactions when an aminoaldehyde is used as reagent, it is preferable to protect the amino function in the aldehyde, e.g. with an acyl blocking group such as acetamido, phthalimido, or the like, prior to carrying out this process, and thence removing the N-protecting group in the 5-epi-X-1-N-(protected aminoalkyl)-4,6-di-O-(aminoglycosyl)-2,5-dideoxystreptamine thereby produced. It may also be advantageous to protect the hydroxyl group in hydroxy-containing aldehydes when carrying out this process; however, it is not generally necessary.

A convenient method of carrying out this process comprises preparing a solution of a 1-N-unsubstituted-5-epi-X-4,6-di-O-(aminoglycosyl)-2,5-dideoxystreptamine antibacterial agent (e.g. 5-epiamino-5-deoxysisomicin) in a protic solvent, (preferably water), and adjusting the pH of the solution to from about pH 2 to about pH 5 with an acid (usually dilute sulfuric acid) thereby preparing the requisite acid addition salt of the starting compound. When the pH of the solution is at about pH 5, the acid addition salt thereby produced usually contains about one equivalent of acid for each amino function in the 5-epi-X-4,6-di-O-(aminoglycosyl)-2,5-dideoxystreptamine (e.g. per mole of 5-epiazido-5-deoxysisomicin there is present 2.5 moles of sulfuric acid; whereas, per mole of 5-epiamino-5-deoxysisomicin there is present 3.0 moles of sulfuric acid). After the acid addition salt solution is prepared, there is added at least a molar equivalent, and preferably a large molar excess of the desired aldehyde (e.g. acetaldehyde) followed within a short time (usually in about 5 minutes) by the addition of about a molar equivalent (based upon the starting 4,6-di-O-(aminoglycosyl)-2,5-dideoxystreptamine) of a hydride-donor reducing reagent, preferably an alkali metal cyanoborohydride, usually sodium cyanoborohydride. The reaction is frequently completed in less than 30 minutes as determined by thin layer chromatography and there is obtained the corresponding 5-epi-X-1-N-alkyl-4,6-di-O-(aminoglycosyl)-2,5-dideoxystreptamine (e.g. 1-N-ethyl-5-epiamino-5-deoxysisomicin) having enhanced antibacterial activity. Isolation and purification of the 1-N-alkyl derivative thereby produced is effected utilizing known techniques such as precipitation, extraction and, preferably, chromatographic techniques.

Alternatively, in the foregoing process, partially N-protected intermediates may be utilized. Thus, for example, one may utilize as starting compound a 1-N-unsubstituted-5-epi-X-4,6-di-O-(aminoglycosyl)-2,5-dideoxystreptamine wherein the amino function at the 6'-carbon is N-protected (e.g. the sulfuric acid addition salt of 6'-N-t-butoxycarbonyl-5-epi-azido-5-deoxysisomicin) or a 1-N-unsubstituted-5-epi-X-4,6-di-O-(aminoglycosyl)-2,5-dideoxystreptamine wherein the amino functions at C-2' and C-3 are N-protected (e.g. the sulfuric acid addition salt of 2',3-di-N-trifluoroacetyl-5-epi-azido-5-deoxygentamicin $C_1$) and there will be formed the corresponding partially N-protected-1-N-alkyl derivative (e.g. 1-N-ethyl-6'-N-t-butoxycarbonyl-5-epi-azido-5-deoxysisomicin and 1-N-ethyl-2',3-di-N-trifluoroacetyl-5-epi-azido-5-deoxygentamicin $C_1$, respectively) which upon removal of the N-protecting groups, according to known methods, yields 1-N-alkyl-5-epi-X- compounds of this invention, e.g. 1-N-ethyl-5-epiamino-5-deoxysisomicin and 1-N-ethyl-5-epiamino-5deoxygentamicin $C_1$, respectively.

In these processes, suitable as N-protecting groups are those groups known in the art to be easily removable after preparation of the 1-N-K-5-epi-X-4,6-di-O-(aminoglycosyl)-2,5-dideoxystreptamines of our invention without affecting the 1-N-alkyl substituent therein. Exemplary of such amino protecting groups are 2,4-dinitrophenyl; acyl groups such as acetyl, propionyl and benzoyl; alkoxycarbonyl groups such as methoxycarbonyl, ethoxycarbonyl, 2,2,2-trichloroethoxycarbonyl, t-butoxycarbonyl and 2-iodoethoxycarbonyl; and arylalkoxycarbonyl groups such as benzyloxycarbonyl and 4-methoxybenzyloxycarbonyl groups.

Another process for the preparation of 1-N-substituted derivatives of the 5-epi-X-4,6-di-O-(aminoglycosyl)-2,5-dideoxystreptamines listed above wherein the substituent is straight chain alkyl having up to 5 carbon atoms and of the pharmaceutically acceptable acid addition salts thereof comprises reacting one of the aforementioned 5-epi-X-4,6-di-O-(aminoglycosyl)-2,5-dideoxystreptamines, which possesses amino-protecting groups at all positions other than position 1, and wherein the 1-amino group may be activated, with an alkylating agent containing the straight chain alkyl group having up to 5 carbon atoms and a leaving group, removing the protecting groups and, if required, the activating group or groups present in the molecule, and isolating the derivative as such or as a pharmaceutically acceptable acid addition salt.

Examples of alkylating agents advantageously used in this process are alklyl iodide, alkyl bromide, dialkyl sulfate, alkyl fluorosulfonate and alklyl p-toluenesulfonate wherein the alkyl group is the required straight chain alkyl group having up to 5 carbon atoms. Other alkylating agents, wherein the alkyl group preferably has one or two carbon atoms, are trialkylanilinium hydroxide, trialkyloxonium fluoroborate, trialkylsulfonium fluoroborate, or trialkylsulfoxonium fluoroborate. All of these alkylating agents contain a good leaving group, such as $Br^-$, $I^-$, $OSO_2F^-$, dialkylaniline or dialkylether.

The amino group in position 1 of the 5-epi-X-4,6-di-O-(aminoglycosyl)-2,5-dideoxystreptamines can be free or activated. An example of an activating group is trifluoromethylsulfonyl. These activating groups may be introduced into the molecule by reacting 5-epi-X-4,6-di-O-(aminoglycosyl)-2,5-dideoxystreptamine which possess amino-protecting groups at all positions other than position 1, with a compound providing the activating group, such as trifluoromethylsulfonyl chloride.

The 1-amino group can also be alkylated by way of the corresponding di-(2-cyanoethyl)-derivative which is derived by treatment with acrylonitrile of the 4,6-di- O-(aminoglycosyl)-2,5-dideoxystreptamine which possesses amino protecting groups at all positions other than position 1. The 1-N-di-(2-cyanoethyl)-derivative thus prepared is then alkylated with one of the above listed alkylating agents followed by removal of the cyanoethyl groups.

The process of the invention is carried out under conditions similar to those employed in the well-known direct alkylation procedures of amines.

Yet other processes for the preparation of 1-N-substituted derivatives of the 5-epi-X-4,6-di-O-(aminoglycosyl)-2,5-dideoxystreptamines listed above, wherein the substituent is methyl, and of the pharmaceutically acceptable acid addition salts thereof, comprise reacting of 5-epi-X-4,6-di-O-(aminoglycosyl)-2,5-dideoxystreptamine which possesses amino-protecting groups at all positions other than position 1, either with formaldehyde and a cyclic imide, preferably succinimide, and treating the so-obtained compound with a hydride-donor reducing agent, preferably sodium borohydride.

A process for the preparation of a 1-N-substituted derivative of the 5-epi-X-4,6-di-O-(aminoglycosyl)-2,5-dideoxystreptamines listed above, wherein the substituent is 2-hydroxyethyl, and of the pharmaceutically acceptable acid addition salts thereof comprises reacting one of these 5-epi-X-4,6-di-O-(aminoglycosyl)-2,5-dideoxystreptamine which possesses amino-protecting groups at all positions other than position 1, with ethylene oxide, removing all protecting groups present in the molecule and isolating the derivatives as such or as a pharmaceutically acceptable acid addition salt.

Another method for preparing the 1-N-alkyl derivatives of the 5-epi-X-4,6-di-O-(aminoglycosyl)-2,5-dideoxystreptamines such as defined by formulae I, II, III and IV, comprises treating with an amide-reducing hydride reagent, in a non-reactive organic solvent, the corresponding 1-N-acyl-5-epi-X-4,6-di-O-(aminoglycosyl)-2,5-dideoxystreptamine, said acyl having the formula K'-CO-wherein K' is a member selected from the group consisting of hydrogen and an alkyl substituent selected from the group consisting of alkyl, cycloalkyl, alkenyl, aralkyl, hydroxyalkyl, aminoalkyl, alkylaminoalkyl, aminohydroxyalkyl, and alklylaminohydroxyalkyl, said alkyl substituent having up to 7 carbon atoms, and, when said alkyl substituent is substituted by both hydroxyl and amino functions, only one of said functions can be attached to any one carbon atom.

By non-reactive organic solvents are contemplated solvents in which the 1-N-acyl-5-epi-X-4,6-di-O-(aminoglycosyl)-2,5-dideoxystreptamine and the amide-reducing reagent are soluble and which will not react with the reagent so there is produced a minimum of competing side reactions. Non-reactive organic solvents which are most useful in our reduction process are ethers such as dioxane, tetrahydrofuran, DYGLYME (i.e. diethyleneglycol dimethyl ether) and the like.

Preferred amide-reducing hydride reagents are aluminum hydrides and borohydrides including lithium aluminum hydride, lithium trimethoxy aluminum hydride, aluminum hydride, diborane, di-isoamylborane, and 9-BBN (i.e. 9-borabicyclo[3.3.1]nonane).

In general, diborane is preferably used as the amide-reducing agent except when the starting compound possesses a double bond, e.g. as in 1-N-acyl-5-epi-X-5-deoxysisomicin, 1-N-acyl-5-epi-X-5-deoxyverdamicin, 1-N-acyl-5-epi-X-5-deoxy-Antibiotic 66-40B, 1-N-acyl-5-epi-X-5-deoxy-Antibiotic 66-40D, and 1-N-acyl-5-epi-X-5-deoxy-Antibiotic G-52, which compounds are conveniently reduced by means of lithium aluminum hydride.

In this process, whereby a 1-N-acyl-5-epi-X-4,6-di-O-(aminoglycosyl)-2,5-dideoxystreptamine is reduced to the corresponding 1-N-alkyl derivative of the invention, if the acyl side chain of the 1-N-acyl-5-epi- intermediate possesses a chiral center, one can use each stereoisomer separately or a mixture thereof, and there will be obtained the corresponding diastereoisomers of a mixture thereof, respectively.

The 1-N-acyl-5-epi-X-4,6-di-O-(aminoglycosyl)-2,5-dideoxystreptamine intermediates of this process, i.e. the 1-N-(COK')-5-epi-X-4,6-di-O-(aminoglycosyl)-2,5-dideoxystreptamines wherein K' is as hereinabove defined (e.g. 1-N-acetyl-5-epiamino-5-deoxysisomicin) are prepared by treating the corresponding 1-N-unsubstituted-5-epi-X-4,6-di-O-(aminoglycosyl)-2,5-dideoxystreptamine of formulae I, II, III and IV which may have amino-protecting groups at all positions other than at position 1, with an acid of the formula

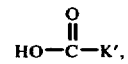

K' being hydrogen or an alkyl substituent as defined for K, and wherein any amino or hydroxy group present may be protected, in the presence of a carbodiimide such as dicyclohexylcarbodiimide, or with a reactive derivative of above said acid, and, if required, removing all protecting groups present in the molecule, the last process step being followed by isolating the derivative as such or as a pharmaceutically acceptable acid addition salt.

Amino-protecting groups useful in the above process must be removable under conditions which will not affect the 1-N-acyl group of the 1-N-acyl-5-epi-X-4,6-di-O-(aminoglycosyl)-2,5-dideoxystreptamine, preferred protecting groups being trifluoroacetyl, t-butoxycarbonyl, and benzyloxycarbonyl.

The 5-epi-X-4,6-di-O-(aminoglycosyl)-2,5-dideoxystreptamine starting compounds of this process may have free amino groups or protected amino groups. If amino groups are protected in the 5-epi-X-4,6-di-O-(aminoglycosyl)-2,5-dideoxystreptamines, 5-epi-X-5-deoxygentamicin B, 5-epi-X-5-deoxygentamicin, $C_{1a}$, 5-epi-X-5-deoxy-Antibiotic JI-20A, 5-epi-X-5-deoxy-Antibiotic 66-40B, 5-epi-X-5-deoxy-Antibiotic 66-40D, 5-epi-X-5-deoxysisomicin, it is usually the 6α-amino group being protected. 5-Epi-X-5-deoxygentamicin $C_1$ may be protected at positions 2' and 3. The 5-epi-X-5-deoxy-4,6-di-O-(aminoglycosyl)-2,5-dideoxystreptamine starting compounds may be used as a free nitrogen base (with or without N-protecting grops) or, as a compound wherein 1 to n amino groups of the 5-epi-X-5-deoxy-4,6-di-O-(aminoglycosyl)-2,5-dideoxystreptamine are neutralized by formation of an acid addition salt whereby n is the number of amino groups in the molecule. The acid addition salt may also contain N-protecting groups. In a preferred method of the acylating process, (n-1) amino groups are neutralized by formation of an acid addition salt. For example, one equivalent of 5-epi-azido-5-deoxygentamicin $C_1$ having 5 amino groups (n=5) requires 5 equivalents of acid to form the "per" acid addition salt, whereas 6 equivalents would be required with the corresponding 5-epiamino-5-deoxy analog. In the preferred method, an acid addition salt of 5-epi-amino-5-deoxygentamicin $C_1$ is used having (n−1), i.e. 5 amino groups which are protonated. The term "acid addition salt" embraces such salts as may be formed between the basic antibiotic and an acid without regard to whether the acid may be termed inorganic or organic. Exemplary of acids embraced by the term are sulfuric, hydrochloric, phosphoric, nitric, trifluoroacetic or the like.

If it is desired to use as a starting material an acid addition salt, wherein (n−1) amino groups are protonated, this compound is advantageously produced in situ thereby reacting a per acid addition salt with an equivalent of strong base, e.g. triethylamine.

In general, the use of reactive derivatives of the acid

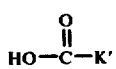

as acylating agents is preferred. Reactive derivatives of the acid comprise esters, azides, imidazole derivatives or anhydrides. In those instances wherein K' is unsubstituted, one of the preferred reactive derivatives is the anhydride of the requisite acid. In other instances it may be preferable to use the N-hydroxysuccinimidyl ester of the acid.

When carrying out the process whereby a reactive derivative of an acid containing an amino function is used, it is preferable to protect the amino function prior to carrying out the process and then removing the N-protecting group in the compound thereby formed. It may also be advantageous to protect a hydroxy group present in the acylating agent, however, it is not generally necessary.

1-N-Acyl-5-epi-X-4,6-di-O-(aminoglycosyl)-2,5-dideoxystreptamines (i.e. the 1-N-COK' derivatives of formulae I, II, III and IV, K' being as hereinabove defined) in addition to being intermediates in the preparation of 1-N-alkyl derivatives of formulae I to IV, are also valuable in that they exhibit broad spectrum antibacterial activity per se, the 1-N-acetyl derivatives being particularly useful compounds. Thus, the pharmaceutically acceptable acid addition salts of the 1-N-acylated compounds are also included within my invention.

The processes described hereinabove are illustrated in detail hereinbelow in the Preparations and Examples but should not be construed as limiting the scope of my invention, obvious equivalents of which will be apparent to those skilled in the art and are considered as within the scope of this invention.

PREPARATION 1

GENTAMICIN $C_{2a}$

A. Separation of Gentamicin $C_{2a}$ from Co-produced Antibiotics

Dissolve 96 gms. of gentamicin base (prepared from the sulfate salt obtained by the procedure of Example 4 of U.S. Pat. No. 3,091,572) in 400 ml. of the upper phase which results when methanol, chloroform and 17% ammonium hydroxide are mixed in the volume ratio of 1:2:1. Add one tenth of the solution to each of the first ten tubes in a 500 × 80 ml. tube counter current extractor. Fill all of the tubes including the first ten to capacity with the lower phase of the above-described solvent mixture. Set the solvent reservoir to deliver 40 ml. of upper phase to tube one (1) for each transfer. Set the apparatus for 500 transfers. When the transfers are complete, sample every eighth tube for chromatography (in duplicate) on Schleicher and Schuell Paper No. 589 using the lower phase of the above-described solvent mixture. Permit the chromatograms to develop for about 16 hours, then dry the papers. Place one paper on an agar plate seeded with *Staphylococcus aureus* (A.T.C.C. 6538P), spray the duplicate with the conventional ninhydrin solution and heat to develop. Incubate the agar plate at 37° C overnight and combine the solution from tubes containing the material that migrates like gentamicin $C_1$ (i.e. tubes 290–360).

Replace tubes 290–360 with fresh tubes containing 40 ml. of upper phase and 40 ml. of lower phase. Reset the apparatus for an additional 2800 transfers and repeat the chromatographic procedure performed above. Combine tubes 1–16 and concentrate in vacuo to obtain 1.3 gms. of gentamicin $C_{2a}$ having the following properties:

a. a molecular weight of 463 as determined by mass spectrometry which is consistent with an empirical formula of $C_{20}H_{41}N_5O_7$;

b. a proton magnetic resonance (pmr) spectrum as follows: pmr (ppm) ($D_2O$): $\delta 0.99$ (3H, d, J=6.5Hz, CH-C$\underline{H}_3$); 1.17 (3H, s, C-C$\underline{H}_3$); 2.47 (3H, s, N-C$\underline{H}_3$); 2.51 (1H, d, J=10.5Hz, H-3''); 3.75 (1H, q, J=10.5, 4Hz, H-2''); 4.00 (1H, d, J=12Hz, H-5'' eq); 5.04 (1H, d, J=4Hz, H-1''); 5.13 (1H, d, J=3.5Hz, H-1').

Irradiation of the secondary methyl group at $\delta 0.99$ ppm reveals H-6' as a doublet (J=6.5Hz) at $\delta 2.81$ ppm.

B. Biological Activity

Gentamicin $C_{2a}$ exhibits substantially the same antibacterial spectrum in vitro as do gentamicin $C_1$, $C_{1a}$ and $C_2$. It exhibits (as the free base) about 74% of the activity of the gentamicin "C" complex. Thus, the antibiotic is useful for substantially the same antibacterial indications and in the same manner as disclosed in U.S. Pat. No. 3,091,572. For example, it is useful in wash solutions, for sanitary purposes, as in the washing of hands and the cleaning of equipment in contaminated rooms.

In Table 1, set forth below is shown the in vitro minimal inhibitory concentration (MIC) of gentamicin $C_{2a}$ against representative gram-positive and gram-negative bacteria. The results are derived using the standard tube dilution method in Mueller-Hinton broth.

TABLE 1

| Organism | MIC (mcg/ml) |
|---|---|
| *Escherichia coli* ATCC 10536 | 0.3 |
| LA 290/R55 | 17.5* |
| JR66 | 7.5* |
| *Pseudomonas aeruginosa* 762 | 0.8 |
| 3223 | 0.3 |
| 20 | 3.0 |
| St 138 | >25* |
| Travers | >25* |
| *Klebsiella pneumoniae* 17 | 0.8 |
| 3694 | 17.5* |
| *Salmonella typhi.* B. | 0.3 |
| *Staphylococcus aureus* 6538P | 0.3 |
| Ziegler | 0.3 |
| 59N | 0.3 |
| *Streptococcus pyogenes* C | 7.5 |
| *Bacillus subtilis* 663 | 0.1 |

*Gentamicin resistant

The acute intravenous $LD_{50}$ of gentamicin $C_{2a}$ is 110 mg/kg when determined in male CF-1 (Carworth Farms) mice weighing 20 grams each.

PREPARATION 2

GENTAMICIN $C_{2b}$

A. Separation of Gentamicin $C_{2b}$ from Co-produced Antibiotics

Separate the major gentamicin C components ($C_1$, $C_2$ and $C_{1a}$) as described in U.S. Pat. No. 3,651,042, Example 2, and combine those fractions containing predominantly overlaps of gentamicins $C_1$ and $C_2$ free base (500 g. of gentamicin C mixture gives 53.4 g. of overlaps). Apply 1.5 g. of this gentamicin $C_1$ and $C_2$ mixture to a column containing 50 g. of silica gel made up in a solvent system comprising chloroform:methanol:15% ammonium hydroxide (1:2:1). Elute the column with the same solvent system and monitor the eluted fractions by thin layer chromatography on silica gel plates using the solvent system chloroform:methanol:22% ammonium hydroxide (1:2:1) as developer. Combine those fractions containing a mixture of gentamicins $C_1$ and $C_2$ together with gentamicin $C_{2b}^-$ (Fractions 39–57 (410 mg.)). Rechromatograph fractions 39–57 over silica gel using a chloroform:methanol:7% ammonium hydroxide (1:2:1) solvent system and combine those fractions (98–130) containing pure gentamicin $C_{2b}$ as determined by thin layer chromatography (yield 45 mg.) having the following constants $[\alpha]_D^{26} + 165°$ (C=0.3%, $H_2O$); Mass spectrum: m/e 463 (M + 1)$^+$, 446, 445, 433, 350, 332, 322, 304, 333, 305, 287, 191, 173, 163, 145, 160, 142, 118, 143; pmr (ppm) ($D_2O$): $\delta$1.25 (3H, s, C-C$\underline{H}_3$); 2.40 (3H, s, N-C$\underline{H}_3$); 2.55 (3H, s, N-C$\underline{H}_3$); 5.12 (1H, d, J=4Hz, H-1''); 5.22 (1H, d, J=3Hz, H-1').

Pure gentamicin $C_{2b}$ can be differentiated from gentamicin $C_1$ and $C_2$ by its mobility on thin layer chromatography using silica gel plates and a chloroform:methanol:22% ammonium hydroxide (1:2:1) solvent system as developer. The approximate Rf values in this system are as follows:

| | |
|---|---|
| Gentamicin $C_1$ | 0.47 |
| Gentamicin $C_2$ | 0.47 |
| Gentamicin $C_{2b}$ | 0.35 |

B. Biological Activity

Gentamicin $C_{2b}$ exhibits substantially the same antibacterial spectrum in vitro as do gentamicin $C_1$, $C_{1a}$ and $C_2$. Thus, the antibiotic is useful for substantially the same antibacterial indications and in the same manner as disclosed in U.S. Pat. No. 3,091,572.

In Table 2, set forth below is shown the in vitro minimal inhibitory concentration (MIC) of gentamicin $C_{2b}$ against representative gram-positive and gram-negative bacteria. The results are derived using the standard tube dilution method in Mueller-Hinton broth.

TABLE 2

| Organism | MIC (mcg/ml) |
|---|---|
| Escherichia coli ATCC 10536 | 0.075 |
| LA 290/R55 | >25.0* |
| JR66 | 7.5* |
| Pseudomonas aeruginosa 762 | 0.3 |
| 3223 | 0.075 |
| 20 | 0.3 |
| St 138 | 17.5* |
| Travers | >25* |
| Klebsiella pneumoniae 17 | 0.075 |
| 3694 | 17.5* |
| Salmonella typhi. B. | 0.3 |
| Staphylococcus aureus wood | 0.075 |
| Ziegler | 0.075 |
| 59N | 0.075 |
| Streptococcus pyogenes C | 3.0 |
| Bacillus subtilis 663 | <0.05 |

*Gentamicin resistant

EXAMPLE I

PER-N-BENZYLOXYCARBONYLAMINOGLYCOSIDES

A. 1,3,2',6',3''-Penta-N-benzyloxycarbonylgentamicin $C_{1a}$

Dissolve 40 gms. of gentamicin $C_{1a}$ in 200 ml. of methanol and 20 ml. of saturated sodium bicarbonate and cool the solution to 0° C. While stirring the solution, add dropwise over a period of 2 hours, 88 ml of carbobenzyloxy chloride keeping the reaction temperature between 0° C to 5° C. Stir the mixture overnight while allowing the reaction temperature to come to room temperature. Add 500 ml of chloroform to the reaction mixture which will then separate into 2 layers. Wash the organic phase with 4 × 100 ml of water and dry over 100 gms of sodium sulfate. Evaporate the organic phase under vacuum at a temperature of less than 40° C. Dissolve the resultant crude product in 100 ml chloroform and add dropwise to 250 ml of 75% hexane/ether. Filter the resultant precipitate and wash with 100 ml hexane and air dry to obtain 87 grms (87%) of 1,3,2',6',3''-Penta-N-benzyloxycarbonylgentamicin $C_{1a}$, melting point = 185°–190° C, $[\alpha]_D^{26} + 71.2$ ($CH_3OH$), Infrared (IR) (KCl): 3300, 3500 cm$^{-1}$, PMR ($CDCl_3$): $\delta$1.2 (C-Me), 3.0 (N-Me), 7.25 (aromatic H)

B. In a similar manner subject to the process described in Example IA equivalent quantities of the following antibiotics:
1. gentamicin $C_1$
2. gentamicin $C_2$
3. gentamicin $C_{2a}$
4. gentamicin $C_{2b}$
5. Antibiotic G-52
6. verdamicin
7. Antibiotic 66-40D Isolate the resultant products in the manner described in Example IA to obtain, respectively:
1. 1,3,2',6',3''-Penta-N-benzyloxycarbonylgentamicin $C_1$,
2. 1,3,2',6',3''-Penta-N-benzyloxycarbonylgentamicin $C_2$,
3. 1,3,2',6',3''-Penta-N-benzyloxycarbonylgentamicin $C_{2a}$,
4. 1,3,2',6',3''-Penta-N-benzyloxycarbonylgentamicin $C_{2b}$,
5. 1,3,2',6',3''-Penta-N-benzyloxycarbonyl-Antibiotic G-52,
6. 1,3,2',6',3''-Penta-N-benzyloxycarbonylverdamicin, and
7. 1,3,2',6',3''-Penta-N-benzyloxycarbonyl-Antibiotic 66-40D.

c. 1,3,2',6',3''-Penta-N-benzyloxycarbonylsisomicin

Dissolve 25 gms. of sisomicin and 13 gms. of sodium carbonate in 625 ml. of water. While stirring the solution add 100 ml. of carbobenzyloxy chloride at 25° C. Stir the mixture for 16 hours and then filter off the solid, washing thoroughly with water. Dry the solid in vacuo and then wash with hexane and air dry to obtain 62 gms. of 1,3,2',6',3''-penta-N-benzyloxycarbonylsisomicin. Melting point = 165°–173° C; $[\alpha]_D^{26} + 96.2$ (CH$_3$OH), Infrared (IR) = $\nu$max (CHCl$_3$), 3600, 1720, 1515, 1215, 1050, 695 cm$^{-1}$; PMR $\delta$(CDCl$_3$) 1.03 (3H, broad singlet, 4''-C-CH$_3$), 3.02 (3H, broad singlet, 3''-N CH$_3$), 5.02 (1OH, broad singlet-CH$_2$C$_6$H$_5$), 3.28, 3.30 ppm. (25 H, broad singlets, -CH$_2$C$_6$H$_5$).

D. In a manner similar to that described in Example 1A, treat each of the following aminoglycosides with carbobenzyloxy chloride in methanol: tobramycin, 3'4'-dideoxykanamycin B, gentamicin B, gentamicin B$_1$, gentamicin X$_2$, Antibiotic G-418, gentamicin A, Antibiotic 66-40B, Antibiotic JI-20A, Antibiotic JI-20B, kanamycin A and kanamycin B. Isolate and purify each of the resultant products in a manner similar to that described in Example 1A to obtain, respectively, 1. 1,3,2',6',3''-penta-N-benzyloxycarbonyltobramycin,
2. 1,3,2',6',3''-penta-N-benzyloxycarbonyl-3',4'-dideoxykanamycin B,
3. 1,3,6',3''-tetra-N-benzyloxycarbonylgentamicin B,
4. 1,3,6',3''-tetra-N-benzyloxycarbonylgentamicin B$_1$,
5. 1,3,2',3''-tetra-N-benzyloxycarbonylgentamicin X$_2$,
6. 1,3,2',3''-tetra-N-benzyloxycarbonyl-Antibiotic G-418,
7. 1,3,2',3''-tetra-N-benzyloxycarbonylgentamicin A,
8. 1,3,2',6',3''-penta-N-benzyloxycarbonyl-Antibiotic 66-40B,
9. 1,3,2',6',3''-penta-N-benzyloxycarbonyl-Antibiotic JI-20A,
10. 1,3,2',6',3''-penta-N-benzyloxycarbonyl-Antibiotic JI-20B,
11. 1,3,6',3''-tetra-N-benzyloxycarbonylkanamycin A, and
12. 1,3,2',6',3''-penta-N-benzyloxycarbonylkanamycin B.

EXAMPLE II

PER-N-BENZYLOXYCARBONYL-3'',4''-N,O,-CARBONYLAMINOGLYCOSIDES

A. 1,3,2',6'-tetra-N-benzyloxycarbonyl-3'',4''-N,O-carbonylgentamicin C$_{1a}$

To a stirred mixture of 60 mg sodium hydride in 5 ml of dry dimethylformamide add a solution of 2 gms of the product of Example IA in 50 ml of dry dimethylformamide over one-half hour at room temperature under nitrogen. Stir the reaction mixture for 2 hours and then filter off insolubles. To the filtrate add 100 ml of chloroform and wash the organic phase with 3 × 50 ml of water. Dry the organic phase over 25 gm sodium sulfate and then evaporate under reduced pressure. Dissolve the resultant residue in 15 ml of chloroform and add dropwise to 75% hexane:ether (15 ml). Filter the precipitate and wash with 25 ml hexane to obtain 1.82 gm (>95%) of 1,3,2',6'-tetra-N-benzyloxycarbonyl-3'',4''-N,O-carbonylgentamicin C$_{1a}$. Melting point = 215° C (dec.) $[\alpha]_D^{26}$ + 63.4 Infrared (IR)-(KCl) = 3300, 3500, 1680, 1545, PMR (CDCl$_3$) $\delta$1.28 (C-Me), 2.58 (N-Me), 7.25 (aromatic H).

B. In a similar manner, subject to the process described in Example IIA equivalent quantities of the products of Example IB and isolate each of the resultant products to obtain respectively, 1. 1,3,2',6'-tetra-N-benzyloxycarbonyl-3'',4''-N,O-carbonylgentamicin C$_1$,
2. 1,3,2',6'-tetra-N-benzyloxycarbonyl-3'',4''-N,O-carbonylgentamicin C$_2$,
3. 1,3,2',6'-tetra-N-benzyloxycarbonyl-3'',4''-N,O-carbonylgentamicin C$_{2a}$,
4. 1,3,2',6'-tetra-N-benzyloxycarbonyl-3'',4''-N,O-carbonylgentamicin C$_{2b}$,
5. 1,3,2',6'-tetra-N-benzyloxycarbonyl-3'',4''-N,O-carbonyl-Antibiotic G-52,
6. 1,3,2',6'-tetra-N-benzyloxycarbonyl-3'',4''-N,O-carbonylverdamicin, and,
7. 1,3,2',6'-tetra-N-benzyloxycarbonyl-3'',4''-N,O-carbonyl-Antibiotic 66-40D.

C. 1,3,2',6'-Tetra-N-Benzyloxycarbonyl-3'',4''-N,O-Carbonylsisomicin

To a stirred solution of 5 gms. of the product of Example IC in 50 ml. of dimethylformamide add 250mg. of sodium hydride. Stir the reaction mixture under argon for 2 hours at room temperature. Filter and add 2 ml. glacial acetic acid to the filtrate. Concentrate the filtrate in vacuo and extract the residue with 200 ml. of chloroform (purified by passage through basic alumina). Wash the chloroform extracts with water and dry over sodium sulfate and evaporate to obtain 3.5 gms. of 1,3,2',6'-tetra-N-benzyloxycarbonyl-3'',4''-N,O-carbonylsisomicin; melting point = 210°–213° C; $[\alpha]_D^{26}$ + 68.8 (c 0.22) Infrared (IR) $\nu$max (nujol) 3550, 1760, 1580 cm$^{-1}$ PMR $\delta$(CDCl$_3$) 1.34 (3H, singlet-4''-CH$_3$), 2.68 (3H, singlet-3''-N-CH$_3$), 5.04 (8H, broad singlet-CH$_2$C$_6$H$_5$).

D. In a manner similar to that described in Example IIA, treat each of the following benzyloxycarbonylaminoglycosides of Example ID with sodium hydride in dimethylformamide.

1. 1,3,6',3''-tetra-N-benzyloxycarbonylgentamicin B,
2. 1,3,6',3''-tetra-N-benzyloxycarbonylgentamicin B$_1$,
3. 1,3,2',3''-tetra-N-benzyloxycarbonylgentamicin X$_2$,
4. 1,3,2',3''-tetra-N-benzyloxycarbonyl-Antibiotic G-418,
5. 1,3,2',6',3''-penta-N-benzyloxycarbonyl-Antibiotic JI-20A,
6. 1,3,2',6',3''-penta-N-benzyloxycarbonyl-Antibiotic JI-20B.

Isolate and purify each of the resultant products in a manner similar to that described in Example IIA to obtain, respectively, 1. 1,3-di-N-benzyloxycarbonyl-6',4';3'',4''-di-N,O-carbonylgentamicin B,
2. 1,3-di-N-benzyloxycarbonyl-6',4';3'',4''-di-N,O-carbonylgentamicin B$_1$,
3. 1,3,2'-tri-N-benzyloxycarbonyl-3'',4''-N,O-carbonylgentamicin X$_2$,
4. 1,3,2'-tri-N-benzyloxycarbonyl-3'',4''-N,O-carbonyl-Antibiotic G-418,
5. 1,3,2',6'-tetra-N-benzyloxycarbonyl-3'',4''-N,O-carbonyl-Antibiotic JI-20A,
6. 1,3,2',6'-tetra-N-benzyloxycarbonyl-3'',4''-N,O-carbonyl-Antibiotic JI-20B.

EXAMPLE III

PER-N-BENZYLOXYCARBONYL-2''-O-HYDROCARBONCARBONYL-3'',4''-N,O-CARBONYLAMINOGLYCOSIDES

A. 1,3,2',6'-tetra-N-benzyloxycarbonyl-2''-O-Benzoyl-3'',4''-N,O-carbonylgentamicin C$_{1a}$ To a stirred solution of 10 gm of 1,3,2',6'-tetra-N-benzyloxycarbonyl-3'',4''-N,O-carbonylgentamicin C$_{1a}$ in 50 ml of dry pyridine add dropwise over a period 10–15 minutes under an atmosphere of nitrogen, 2 ml benzoyl chloride. Stir the reaction mixture for ½ hour and then remove the pyridine via a rotary evaporator keeping the bath temperature at less than 30° C. Dissolve the residual pale yellow oil in 100 ml of chloroform. Wash this organic phase with 3 + 50 ml water and then dry over 25 gm sodium sulfate. Evaporate the chloroform under vacuum. Triturate the residual yellow foam with a small volume of ether to obtain 11.0 gms. (>95%) 1,3,2',6'-tetra-N-benzyloxycarbonyl-2''-O-benzoyl-3'', 4''-N,O-carbonylgentamicin $C_{1a}$. Melting point = 120°–123° C $[\alpha]_D^{26}$ + 73.8.

B. In a similar manner, subject to the process described in Example IIIA, equivalent quantities of the products of Example IIB and isolate the resultant products to obtain respectively:
1. 1,3,2',6'-tetra-N-benzyloxycarbonyl-2''-O-Benzoyl-3'',4''-N,O-carbonylgentamicin $C_1$,
2. 1,3,2',6'-tetra-N-benzyloxycarbonyl-2''-O-Benzoyl-3'',4''-N,O-carbonylgentamicin $C_2$,
3. 1,3,2',6'-tetra-N-benzyloxycarbonyl-2''-O-Benzoyl-3'', 4''-N,O-carbonylgentamicin $C_{2a}$,
4. 1,3,2',6'-tetra-N-benzyloxycarbonyl-2''-O-Benzoyl-3'',4''-N,O-carbonylgentamicin $C_{2b}$,
5. 1,3,2',6'-tetra-N-benzyloxycarbonyl-2''-O-Benzoyl-3'',4''-N,O-carbonyl-Antibiotic G-52,
6. 1,3,2',6'-tetra-N-benzyloxycarbonyl-2''-O-Benzoyl-3'',4''-N,O-carbonylverdamicin, and
7. 1,3,2',6'-tetra-N-benzyloxycarbonyl-2''-O-Benzoyl-3'',4''-N,O-carbonyl-Antibiotic 66-40D.

C. 1,3,2',6'-Tetra-N-Benzyloxycarbonyl-2''-O-Benzoyl-3'',4''-N,O-Carbonylsisomicin To a stirred solution of 3 gms. of the product of Example IIC in 20 ml. of dry pyridine at 25° C under an atmosphere of argon add 1.7 ml. of benzoylchloride over a 10 minute period. Stir at room temperature until all the starting material reacts (monitor by thin layer chromatography). Evaporate the mixture at room temperature under high vacuum; extract the solid residue with 100 ml. chloroform (previously passed through basic alumina). Wash the chloroform extracts with 5% aqueous sodium bicarbonate, water and then dry over sodium sulfate. Evaporate the solvent to obtain 2.8 gms. 1,3,2',6'-tetra-N-benzyloxycarbonyl-2''-O-benzoyl-3'',4''-N,O-carbonylsisomicin; melting point 157°–160° C, $[\alpha]_D^{26}$ + 86, (c 0.2) Infrared (IR) $\nu$max (nujol) 3325, 1780, 1680, 1560 cm$^{-1}$ PMR $\delta$ (CDCl$_3$) 1.35 (4''-C-CH$_3$), 2.74 (3''-N-CH$_3$), 5.03 (CH$_2$-C$_6$H$_5$).

EXAMPLE IV

PER-N-BENZYLOXYCARBONYL-2''-O-HYDROCARBONCARBONYL-5-O-HYDROCARBONSULFONYL-3'',4''-N,O-CARBONYLAMINO-GLYCOSIDES

A. 1,3,2',6'-tetra-N-benzyloxycarbonyl-5-O-Methanesulfonyl-2''-O-benzoyl-3'',4''-N,O-carbonylgentamicin $C_{1a}$ Cool a solution of 1 gm. of 1,3,2',6'-tetra-N-benzyloxycarbonyl-2''-O-benzoyl-3'',4''-N,O-carbonylgentamicin $C_{1a}$ in 5 ml. of triethylamine and 15 ml. tetrahydrofuran to below 0° C. Stir the solution and to it add, over a period of 15 minutes, a solution of 1 ml. of methanesulfonyl chloride in 5 ml. of tetrahydrofuran. Stir the reaction mixture for 2 hours at 0° C. Pour the reaction mixture into 25 ml of water and 25 ml of chloroform. Wash the organic phase with 2 × 15 ml of water and then dry the organic phase over sodium sulfate. Evaporate the chloroform and triturate the resulting yellow foam with small amounts of ether to obtain 1.2 gm (>95%) of the 1,3,2',6'-tetra-N-benzyloxycarbonyl-5-O-methanesulfonyl-2''-O-benzoyl-3'',4''-N,O-carbonylgentamicin $C_{1a}$. Melting point = 130° C $[\alpha]_D^{26}$ + 53.4 (CHCl$_3$) PMR (CDCl$_3$) $\delta$1.35 (C-Me), 2.74 (N-Me), 2.99 (OSO$_2$CH$_3$), 7.28 (4×Cbz and benzoyl).

B. In a similar manner, subject to the process described in Example IVA equivalent quantities of the products of Example IIIB and isolate the resultant products to obtain respectively:
1. 1,3,2',6'-tetra-N-benzyloxycarbonyl-5-O-methanesulfonyl-2''-O-benzoyl-3'',4''-N,O-carbonylgentamicin $C_1$,
2. 1,3,2',6'-tetra-N-benzyloxycarbonyl-5-O-methanesulfonyl-2''-O-benzoyl-3'',4''-N,O-carbonylgentamicin $C_2$,
3. 1,3,2',6'-tetra-N-benzyloxycarbonyl-5-O-methanesulfonyl-2''-O-benzoyl-3'',4''-N,O-carbonylgentamicin $C_{2a}$,
4. 1,3,2',6'-tetra-N-benzyloxycarbonyl-5-O-methanesulfonyl-2''-O-benzoyl-3'',4''-N,O-carbonylgentamicin $C_{2b}$,
5. 1,3,2',6'-tetra-N-benzyloxycarbonyl-5-O-methanesulfonyl-2''-O-benzoyl-3'',4''-N,O-carbonyl-Antibiotic G-52,
6. 1,3,2',6'-tetra-N-benzyloxycarbonyl-5-O-methanesulfonyl-2''-O-benzoyl-3'',4''-N,O-carbonylverdamicin, and
7. 1,3,2',6'-tetra-N-benzyloxycarbonyl-5-O-methanesulfonyl-2''-O-benzoyl-3'',4''-N,O-carbonyl-Antibiotic 66-40D.

C. 1,3,2',6'-Tetra-N-Benzyloxycarbonyl-5-O-Methanesulfonyl-2''-O-Benzoyl-3'',4''-N,O-Carbonylsisomicin Dissolve 2.5 gms. of the product of Example IIIC in 15 ml. of dry pyridine. Cool the solution to 10° C and add 4 ml. of methanesulfonyl chloride over a period of 10 minutes, allow the reaction mixture to stand overnight, then concentrate the reaction mixture under vacuum at 25° C. Extract the residue with 150 ml. of acid-free chloroform. Wash the chloroform extracts with water and dry over sodium sulfate. Evaporate the chloroform to give 2.4 gm. of 1,3,2',6'-tetra-N-benzyloxycarbonyl-5-O-methanesulfonyl-2''-O-benzoyl-3'', 4''-N,O-carbonylsisomicin; melting point - 84°–88° C, $[\alpha]_D^{26}$ + 21.3 (c 0.29) Infrared (IR) $\nu$max (nujol) 3325, 1750, 1540 cm$^{-1}$; PMR $\delta$(CDCl$_3$) 1.32 (4''-C-CH$_3$), 2.68 (3''-N-CH$_3$), 3.04

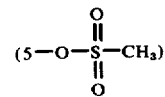

5.00 (-CH$_2$C$_6$H$_5$).

EXAMPLE V

PER-N-BENZYLOXYCARBONYL-O-YLIDENE-AMINOGLYCOSIDES

A. 1,3,2',6',3''-Penta-N-Benzyloxycarbonyl-4'',6''-O-Benzylidene-Tobramycin

To a solution of 5 gms. of 1,3,2',6',3''-penta-N-benzyloxycarbonyltobramycin in 25 ml. of anhydrous dimethylformamide add 1 ml. of benzaldehyde and 300 mg. of dry para-toluenesulfonic acid. Heat in a sealed flask at 110° C. for four hours, cool the solution, then treat the cooled solution with 6 ml. of Amberlite IR- 401S resin in the hydroxide form. Filter off the resin and evaporate the filtrate in vacuo to a residue comprising 1,3,2',6',3''-penta-N-benzyloxycarbonyl-4'',6''-O-benzylidenetobramycin.

B. In a manner similar to that described in above Example VA, treat each of the following per-N-benzyloxycarbonylaminoglycosides with benzaldehyde in dimethylformamide in the presence of para-toluenesulfonic acid.
1. 1,3,2',6',3''-penta-N-benzyloxycarbonyl-3',4'dideoxykanamycin B.
2. 1,3,2',6'-tetra-N-benzyloxycarbonyl-3'',4''-N,O-carbonyl-Antibiotic JI-20A,
3. 1,3,2',6'-tetra-N-benzyloxycarbonyl-3'',4''-N,O-carbonyl-Antibiotic JI-20B,
4. 1,3,2',3''-tetra-N-benzyloxycarbonylgentamicin A,
5. 1,3,6',3''-tetra-N-benzyloxycarbonylkanamycin A,
6. 1,3,2',6',3''-penta-N-benzyloxycarbonylkanamycin B.

Isolate and purify each of the resultant products in a manner similar to that described in Example VA to obtain, respectively.
1. 1,3,2',6',3''-penta-N-benzyloxycarbonyl-4'',6''-O-benzylidene-3',4'dideoxykanamycin B,
2. 1,3,2',6'-tetra-N-benzyloxycarbonyl-3',4'-O-benzylidene-3'',4''-N,O-carbonyl-Antibiotic JI-20A,
3. 1,3,2',6'-tetra-N-benzyloxycarbonyl-3',4'-O-benzylidene-3'',4''-N,O-carbonyl-Antibiotic JI-20B,
4. 1,3,2',3''-tetra-N-benzyloxycarbonyl-4',6'-O-benzylidenegentamicin A,
5. 1,3,6',3''-tetra-N-benzyloxycarbonyl-2',3';4'',6''-di-O-benzylidenekanamycin A in admixture with 1,3,6',3''-tetra-N-benzyloxycarbonyl-3',4';4'',6''-di-O-benzylidenekanamycin A,
6. 1,3,2',6',3''-penta-N-benzyloxycarbonyl-3',4';4'',6''-di-O-benzylidenekanamycin B.

C. 1,3-di-N-benzyloxycarbonyl-2',3'-O-cyclohexylidene-6',4';3'',4''-di-N,O-carbonylgentamicin B To a solution of 5 gms. of 1,3-di-N-benzyloxycarbonyl-6',4';3'',4''-di-N,O-carbonylgentamicin B in 25 ml. of anhydrous dimethylformamide add 5 ml. of 1,1-dimethoxycyclohexane and 300 mg. of dry para-toluenesulfonic acid. Heat in a sealed flask at 110° C for four hours. Cool the solution and then treat the cooled solution with 6 ml. of Amberlite IR-401S resin in the hydroxide form. Filter off the resin and evaporate the filtrate in vacuo to a residue comprising 1,3-di-N-benzyloxycarbonyl-2',3'-O-cyclohexylidene-6',4';3'',4''-di-N,O-carbonylgentamicin B.

D. In a manner similar to that described in Example VC treat each of the following per-N-benzyloxycarbonylaminoglycosides with 1,1-dimethoxycyclohexane and para-toluenesulfonic acid in dimethylformamide.
1. 1,3-di-N-benzyloxycarbonyl-6',4';3'',4''-di-N,O-carbonylgentamicin $B_1$,
2. 1,3,2'-tri-N-benzyloxycarbonyl-3'',4''-N,O-carbonylgentamicin $X_2$,
3. 1,3,2'-tri-N-benzyloxycarbonyl-3'',4''-N,O-carbonyl-Antibiotic G-418, Isolate and purify each of the resultant products in a manner similar to that described in Example VC to obtain, respectively,
1. 1,3-di-N-benzyloxycarbonyl-2',3'-O-cyclohexylidene-6',4';3'',4''-di-N,O-carbonylgentamicin $B_1$,
2. 1,3,2'-tri-N-benzyloxycarbonyl-4',6'-O-cyclohexylidene-3'',4''-N,O-carbonylgentamicin $X_2$,
3. 1,3,2',tri-N-benzyloxycarbonyl-4',6'-O-cyclohexylidene-3'',4''-N,O-carbonyl-Antibiotic G-418.

EXAMPLE VI

2''-O-BENZOYL-PER-N-BENZYLOXYCARBONYL-O-YLIDENE-AMINOGLYCOSIDES

A. In a manner similar to that described in Example IIIA, treat each of the following aminoglycosides with one equivalent of benzoylchloride in pyridine.
1. 1,3,2',6',3''-penta-N-benzyloxycarbonyl-4'',6''-O-benzylidene-3',4'-dideoxykanamycin B,
2. 1,3-di-N-benzyloxycarbonyl-2',3'-O-cyclohexylidene-6',4';3'',4''-di-N,O-carbonylgentamicin B,
3. 1,3-di-N-benzyloxycarbonyl-2',3'-O-cyclohexylidene-6',4';3'',4''-di-N,O-carbonylgentamicin $B_1$,
4. 1,3,2',6'-tetra-N-benzyloxycarbonyl-3',4'-O-benzylidene-3'',4''-N,O-carbonyl-Antibiotic JI-20A,
5. 1,3,2',6'-tetra-N-benzyloxycarbonyl-3',4'-O-benzylidene-3'',4''-N,O-carbonyl-Antibiotic JI-20B,
6. 1,3,2',6',3''-penta-N-benzyloxycarbonyl-3',4';4'',6''-di-O-benzylidenekanamycin B.

Isolate and purify each of the resultant products in a manner similar to that described in Example IIIA to obtain, respectively,
1. 1,3,2',6',3''-penta-N-benzyloxycarbonyl-2''-O-benzoyl-4'',6''-O-benzylidene-3',4'-dideoxykanamycin B,
2. 1,3-di-N-benzyloxycarbonyl-2',3'-O-cyclohexylidene-6',4';3'',4''-di-N,O-carbonyl-2''-O-benzoylgentamicin B,
3. 1,3-di-N-benzyloxycarbonyl-2',3'-O-cyclohexylidene-6',4';3'',4''-di-N,O-carbonyl-2''-O-benzoylgentamicin $B_1$,
4. 1,3,2',6'-tetra-N-benzyloxycarbonyl-3',4'-O-benzylidene-2''-O-benzoyl-3'',4''-N,O-carbonyl-Antibiotic JI-20A,
5. 1,3,2',6'-tetra-N-benzyloxycarbonyl-3',4'-O-benzylidene-2''-O-benzoyl-3'',4''-N,O-carbonyl-Antibiotic JI-20B,
6. 1,3,2',6',3''-penta-N-benzyloxycarbonyl-3',4';4'',6''-di-O-benzylidene-2''-O-benzoylkanamycin B.

B. In a manner similar to that described in Example IIIA, treat each of the following aminoglycosides with two equivalents of benzoylchloride in pyridine.
1. 1,3,2',6',3''-penta-N-benzyloxycarbonyl-4'',6''-O-benzylidenetobramycin,
2. 1,3,2',6',3''-penta-N-benzyloxycarbonyl-Antibiotic 66-40B,
3. 1,3,2'-tri-N-benzyloxycarbonyl-4',6'-O-cyclohexylidene-3'',4''-N,O-carbonylgentamicin $X_2$,
4. 1,3,2'-tri-N-benzyloxycarbonyl-4',6'-O-cyclohexylidene-3'',4''-N,O-carbonyl-Antibiotic G-418,
5. 1,3,6',3''-tetra-N-benzyloxycarbonyl-2',3';4'',6''-di-O-benzylidenekanamycin A in admixture with 1,3,6',3''-tetra-N-benzoyloxycarbonyl-3',4';4'',6''-di-O-benzylidenekanamycin A.

Isolate and purify each of the resultant products in a manner similar to that described in Example IIIA to obtain
1. 1,3,2',6',3''-penta-N-benzyloxycarbonyl-4',2''-di-O-benzoyl-4'',6''-O-benzylidenetobramycin,
2. 1,3,2',6',3''-penta-N-benzyloxycarbonyl-2'',4''-di-O-benzoyl-Antibiotic 66-40B,
3. 1,3,2'-tri-N-benzyloxycarbonyl-3',2''-di-O-benzoyl-4',6'-O-cyclohexylidene-3'',4''-N,O-carbonylgentamicin $X_2$,
4. 1,3,2'-tri-N-benzyloxycarbonyl-3',2''-di-O-benzoyl-4',6'-O-cyclohexylidene-3'',4''-N,O-carbonyl-Antibiotic G-418, 5. 1,3,6',3'''-tetra-N-benzyloxycarbonyl-2',3';4'',6''-di-O-benzylidene-4',2''-di-O-benzoylkanamycin A in admixture with 1,3,6',3'''-tetra-N-benzyloxycarbonyl-2',2''-di-O-benzoyl-3',4';4'',6''-di-O-benzylidenekanamycin A.

C. In a manner similar to that described in Example IIIA, treat 1,3,2',3''-tetra-N-benzyloxycarbonyl-4',6'-O-benzylidenegentamicin A with three equivalents of benzoyl chloride in pyridine. Isolate and purify the resultant product in a manner similar to that described to obtain 1,3,2',3''-tetra-N-benzyloxycarbonyl-3',2''',4'''-tri-O-benzoyl-4',6'-O-benzylidenegentamicin A.

EXAMPLE VII

5-O-METHANESULFONYL-2''-O-BENZOYL-O-YLIDENE-N-BENZYLOXYCARBONYLAMINO-GLYCOSIDES

In a manner similar to that described in Example IVA, treat each of the compounds prepared in Example VIA, B and C with methanesulfonylchloride in triethylamine and tetrahydrofuran. Isolate and purify each of the resultant products in a manner similar to that described in Example IVA to obtain 1. 1,3,2',6',3''-penta-N-benzyloxycarbonyl-5-O-methanesulfonyl-2''-O-benzoyl-4''',6''-O-benzylidene-3',4'-dideoxykanamycin B,
2. 1,3-di-N-benzyloxycarbonyl-5-O-methanesulfonyl-2',3'-O-cycohexylidene-6',4';3''',4'''-di-N,O-carbonyl-2''-O-benzoylgentamicin B,
3. 1,3-di-N-benzyloxycarbonyl-5-O-methanesulfonyl-2',3'-O-cyclohexylidene-6',4';3''',4'''-di-N,O-carbonyl-2''-O-benzoylgentamicin $B_1$,
4. 1,3,2',6'-tetra-N-benzyloxycarbonyl-5-O-methanesulfonyl-3',4'-O-benzylidene-2''-O-benzoyl-3''',4'''-N,O-carbonyl-Antibiotic JI-20A,
5. 1,3,2',6'-tetra-N-benzyloxycarbonyl-5-O-methanesulfonyl-3',4'-O-benzylidene-2''-O-benzoyl-3''',4'''-N,O-carbonyl-Antibiotic JI-20B,
6. 1,3,2',6',3''-penta-N-benzyloxycarbonyl-5-O-methanesulfonyl-3',4';4'',6''-di-O-benzylidene-2''-O-benzoylkanamycin B,
7. 1,3,2',6',3''-penta-N-benzyloxycarbonyl-5-O-methanesulfonyl-4',2''-di-O-benzoyl-4''',6''-O-benzylidenetobramycin,
8. 1,3,2',6',3''-penta-N-benzyloxycarbonyl-5-O-methanesulfonyl-2''',4'''-di-O-benzoyl-Antibiotic 66-40B,
9. 1,3,2'-tri-N-benzyloxycarbonyl-5-O-methanesulfonyl-3',2''-di-O-benzoyl-4',6'-O-cyclohexylidene-3''',4'''-N,O-carbonylgentamicin $X_2$,
10. 1,3,2'-tri-N-benzyloxycarbonyl-5-O-methanesulfonyl-3',2''-di-O-benzoyl-4',6'-O-cyclohexylidene-3''',4'''-N,O-carbonyl-Antibiotic G-418,
11. 1,3,6',3'''-tetra-N-benzyloxycarbonyl-5-O-methanesulfonyl-2',3';4'',6''-di-O-benzylidene-4',2''-di-O-benzoylkanamycin A in admixture with 1,3,6',3'''-tetra-N-benzyloxycarbonyl-5-O-methanesulfonyl-2',2''-di-O-benzoyl-3',4';4'',6''-di-O-benzylidenekanamycin A.
12. 1,3,2',3''-tetra-N-benzyloxycarbonyl-5-O-methanesulfonyl-3',2''',4'''-tri-O-benzoyl-4',6'-O-benzylidenegentamicin A.

1-N-ALKYL INTERMEDIATES

In the procedures described in Examples I–VII, by utilizing as starting compounds the 1-N-alkyl derivatives of the starting antibacterial aminoglycosides named therein, there is obtained the corresponding 1-N-alkyl-per-N-protected-per-O-protected-5-O-hydrocarbonsylfonyl aminoglycoside intermediates. Of particular interest are 1-N-alkyl derivatives having up to 4 atoms, including alkyl substituents such as ethyl, n-propyl, n-butyl-, δ-aminobutyl-, γ-aminopropyl-, β-hydroxyethyl, S-δ-amino-β-hydroxybutyl and the like. In general, this invention includes 5-epi-X-4,6-di-O-(aminoglycosyl)-2,5-dideoxystreptamines and intermediates useful in their preparation which have 1-N-alkyl substituents having up to 8 carbon atoms also including alkyl derivatives such as β-methylpropyl, n-octyl, β-propenyl, β-ethyl-β-hexenyl, benzylphenylethyl, cyclohexylmethyl, β-hydroxy-δ-pentenyl-, ω-hydroxyoctyl, β-methyl-β-hydroxy-γ-aminopropyl, S-γ-amino-β-hydroxypropyl, and the like.

EXAMPLE VIII

5-EPI-AZIDO-5-DEOXY-2''-O-BENZOYL-PER-N-BENZYLOXYCARBONYLAMINOGLYCOSIDES

A. 1,3,2',6'-tetra-N-benzyloxycarbonyl-5epi-azido-5-deoxy-2''-O-benzoyl-3''',4'''-N,O-carbonylgentamicin $C_{1a}$ Heat 12 gm. 1,3,2',6'-tetra-N-benzyloxycarbonyl-5-O-methanesulfonyl-2''-O-benzoyl-3''',4'''-N,O-carbonylgentamicin $C_{1a}$ and 2 gm. sodium azide in 30 ml. of dimethylformamide together at 120° C for 24 hours. Cool the reaction mixture and remove the solvent in vacuo at 60° C. Dissolve the residue in 50 ml. water and 100 ml. chloroform. Wash the organic phase with 2 × 50 ml. water and dry over 25 gm. of sodium sulfate. Evaporate the solvent to give a white solid. Dissolve the solid in a small volume of chloroform and chromatograph over 200 gm. of silica gel. Elute the column with $CHCl_3$/3% MeOH to give 6 gm. of the resultant 1,3,2',6'-tetra-N-benzyloxycarbonyl-5-epi-azido-5-deoxy-2''-O-benzoyl-3''',4'''-N,O-carbonylgentamicin $C_{1a}$. Melting point = 195°–200° C $[\alpha]_D^{26}$ + 88.9 ($CHCL_3$).

B. In a similar manner, subject to the process described in Example VIIIA equivalent quantities of products 1–5 and 7 of Example IVB and isolate the resultant products to obtain respectively, 1. 1,3,2',6'-tetra-N-benzyloxycarbonyl-5-epi-azido-5-deoxy-2''-O-benzoyl-3''',4'''-N,O-carbonylgentamicin $C_1$,
2. 1,3,2',6'-tetra-N-benzyloxycarbonyl-5-epi-azido-5-deoxy-2''-O-benzoyl-3''',4'''-N,O-carbonylgentamicin $C_2$,
3. 1,3,2',6'-tetra-N-benzyloxycarbonyl-5-epi-azido-5-deoxy-2''-O-benzoyl-3''',4'''-N,O-carbonylgentamicin $C_{2a}$,
4. 1,3,2',6'-tetra-N-benzyloxycarbonyl-5-epi-azido-5-deoxy-2''-O-benzoyl-3''',4'''-N,O-carbonylgentamicin $C_{2b}$,
5. 1,3,2',6'-tetra-N-benzyloxycarbonyl-5-epi-azido-5-deoxy-2''-O-benzoyl-3''',4'''-N,O-carbonyl-Antibiotic G-52,
6. 1,3,2',6'-tetra-N-benzyloxycarbonyl-5-epi-azido-5-deoxy-2''-O-benzoyl-3''',4'''-N,O-carbonyl-Antibiotic 66-40D.

C. 1,3,2',6'-Tetra-N-Benzyloxycarbonyl-5-Epi-Azido-5-Deoxy-2''-O-Benzoyl-3''',4'''-N,O-Carbonylsisomicin 1. Dissolve 2 gm. of the product of Example IVC in 15 ml. of dry dimethylformamide. Stir the mixture and add 1.5 gm. of sodium azide. Keep the reaction mixture under argon at 120° C overnight. Concentrate the solution under high vacuum. Extract the residue with 200 ml. of acid-free chloroform. Wash the chloroform extracts with water and dry over sodium sulfate. Evaporate the solvent to give 1,3,2',6'-tetra-N-benzyloxycarbonyl-5-epi-azido-5-deoxy-2''-O-benzoyl-3'',4''-N,O-carbonylsisomicin. Infrared (nujol) $\nu$max 2100 cm$^{-1}$.

2. In a similar manner subject to the foregoing process an equivalent quantity of the product No. 6 of Example IVB to obtain, 1,3,2',6'-tetra-N-benzyloxycarbonyl-5-epi-azido-5-deoxy-2''-O-benzoyl-3'',4''-N,O-carbonylverdamicin.

D. In a manner similar to that described in Example VIIIA, treat each of the 5-O-methanesulfonylaminoglycosides prepared in Example VII with sodium azide in dimethylformamide. Isolate and purify each of the resultant products in a manner similar to that described in Example VIIIA to obtain, respectively, 1. 1,3,2',6',3''-penta-N-benzyloxycarbonyl-5-epi-azido-2''-O-benzoyl-4'',6''-O-benzylidene-5,3',4'-trideoxykanamycin B,
2. 1,3-di-N-benzoyloxycarbonyl-5-epi-azido-5-deoxy-2',3'-O-cyclohexylidene-6',4';3'',4''-di-N,O-carbonyl-2''-O-benzoylgentamicin B,
3. 1,3-di-N-benzyloxycarbonyl-5-epi-azido-5-deoxy-2',3'-O-cyclohexylidene-6',4';3'',4''-di-N,O-carbonyl-2''-O-benzoylgentamicin B$_1$,
4. 1,3,2',6'-tetra-N-benzyloxycarbonyl-5-epi-azido-5-deoxy-3',4'-O-benzylidene-2''-O-benzoyl-3'',4''-N,O-carbonyl-Antibiotic JI-20A,
5. 1,3,2',6'-tetra-N-benzyloxycarbonyl-5-epi-azido-5-deoxy-3',4'-O-benzylidene-2''-O-benzoyl-3'',4''-N,O-carbonyl-Antibiotic JI-20B,
6. 1,3,2',6',3''-penta-N-benzyloxycarbonyl-5-epi-azido-5-deoxy-3',4';4'',6''-di-O-benzylidene-2''-O-benzoylkanamycin B,
7. 1,3,2',6',3''-penta-N-benzyloxycarbonyl-5-epi-azido-5-deoxy-4',2''-di-O-benzoyl-4'',6''-O-benzylidenetobramycin,
8. 1,3,2',6',3''-penta-N-benzyloxycarbonyl-5-epi-azido-5-deoxy-2'', 4''-di-O-benzoyl-Antibiotic 66-40B,
9. 1,3,2'-tri-N-benzyloxycarbonyl-5-epi-azido-5-deoxy-3',2''-di-O-benzoyl-4',6'-O-cyclohexylidene-3'',4''-N,O-carbonylgentamicin X$_2$,
10. 1,3,2'-tri-N-benzyloxycarbonyl-5-epi-azido-5-deoxy-3',2''-di-O-benzoyl-4',6'-O-cyclohexylidene-3'',4''-N,O-carbonyl-Antibiotic G-418,
11. 1,3,6',3''-tetra-N-benzyloxycarbonyl-5-epi-azido-5-deoxy-2',3';4'',6''-di-O-benzylidene-4',2''-di-O-benzoylkanamycin A in admixture with 1,3,6',3''-tetra-N-benzyloxycarbonyl-5-epi-azido-5-deoxy-2',2''-di-O-benzoyl-3',4';4'',6''-di-O-benzylidenekanamycin A,
12. 1,3,2',3'-tetra-N-benzyloxycarbonyl-5-epi-azido-5-deoxy-3',2'',4''-tri-O-benzoyl-4',6'-O-benzylidenegentamicin A.

EXAMPLE IX

5-EPI-AMINO-5-DEOXYAMINOGLYCOSIDES

A. 5-epi-amino-5-deoxygentamicin C$_{1a}$

Hydrogenate over 1 gm. 30% palladium/carbon at 60 psi at room temperature a solution of 6 gm. of 1,3,2',6'-tetra-N-benzyloxycarbonyl-5-epi-azido-5-deoxy-2''-O-benzoyl-3'',4''-N,O-carbonylgentamicin C$_{1a}$ in 50 ml. of acetic acid. Remove the solvent and catalyst (to obtain a gummy residue) then heat the resultant residue in 25 ml. 2N sodium hydroxide at 100° C for 4 hours. Cool the mixture and neutralize with acetic acid. Filter off the resulting precipitate and concentrate the filtrate to 10 ml. Pass the concentrated filtrate through a column of IRC-50 (H$^+$ form) resin. Wash the column with 200 ml. of water and then elute the column with 100 ml. of 1N ammonium hydroxide. Concentrate the eluate to dryness and lyophilize the residue to obtain 1 gm. 5-epi-amino-5-deoxygentamicin C$_{1a}$. Melting point 112°–116° C [$\alpha$]$_D^{26}$ + 167.0 (H$_2$O), PMR (100 MHz, D$_2$O)

| $\delta$ | | |
|---|---|---|
| 1.21 | (3H,S,C-CH$_3$) | |
| 2.00 | (1H, dt, H-2eq) | |
| 2.50 | (3H, S, N-CH$_3$) | |
| 2.61 | (1H, d, J = 10 Hz, H-3'') | |
| 3.39 | (1H, d, J = 12 Hz, H-5''ax) | |
| 3.81 | (1H, q, H-2'') | |
| 3.82 | (1H, d, J = 12 Hz, H-5''eq) | |
| 4.94 | (1H, d, J = 3Hz, H-1') | |
| 5.06 | (1H, d, J = 3.5 Hz, H-1'') | |

In a similar manner, subject to the process described in Example IXA equivalent quantities of the products 1-4 of Example VIIIB and isolate the resultant products to obtain respectively, 5-epi-amino-5-deoxygentamicin C$_1$, m.p. 95°–98° C, [$\alpha$]$_D^{26}$ +150.7° (c 0.64, H$_2$O),
5-epi-amino-5-deoxygentamicin C$_2$,
5-epi-amino-5-deoxygentamicin C$_{2a}$,
5-epi-amino-5-deoxygentamicin C$_{2b}$, C. 5-Epi-Amino-5-Deoxysisomicin 1. Dissolve the product of Example VIIIC-1 in a mixture of 10 ml. of tetrahydrofuran and 50 ml. of liquid ammonia. Slowly add 2 gm. of sodium to the stirred mixture and continue to stir at -40° C for 2 hours. Allow the ammonia to evaporate at room temperature overnight. Dissolve the resultant residue in 25 ml. of water and heat to 100° C overnight. Cool the solution and adsorb on Amberlite IRC-50 (H$^+$) resin and elute the product with 500 ml. of 1N ammonium hydroxide. Concentrate the ammonium hydroxide eluate under high vacuum to give an oily product. Chromatograph this material on 50 gm. of silica gel using chloroform/methanol/15% ammonium hydroxide (2:1:1) to give 102 mg. of 5-epi-amino-5-deoxysisomicin; melting point = 110°–116° C, [$\alpha$]$_D^{26}$ + 185.2 (c 0.32).

2. In a similar manner subject to the foregoing process equivalent quantities of the products 5 and 6 of Example VIIIB; product of Example VIIIC-2; product 8 of Example VIIID to obtain respectively,
a. 5-epi-amino-5-deoxy-Antibiotic G-52,
b. 5-epi-amino-5-deoxy-Antibiotic 66-40D,
c. 5-epi-amino-5-deoxyverdamicin
d. 5-epi-amino-5-deoxy-Antibiotic 66-40B.

D. In a manner similar to that described in Example IX A, hydrogenate each of the 5-epi-azido-5-deoxy-per-N-protected-per-O-protected aminoglycosides numbers 1-7 and 9-12 prepared in Example VIIID. Further, treat the compounds with 2N sodium hydroxide as described, additionally, treat these compounds with 80% acetic acid/water for 1 hour on the steam bath to remove any acetal or ketal protecting groups.

Isolate and purify each of the resultant products in a manner similar to that described in Example IXA to obtain, respectively,
1. 5-epi-amino-5,3',4'-trideoxykanamycin B,
2. 5-epi-amino-5-deoxygentamicin B,
3. 5-epi-amino-5-deoxygentamicin B$_1$,
4. 5-epi-amino-5-deoxy-Antibiotic JI-20A,
5. 5-epi-amino-5-deoxy-Antibiotic JI-20B, 6. 5-epi-amino-5-deoxykanamycin B,
7. 5-epi-amino-5-deoxytobramycin,
8. 5-epi-amino-5-deoxygentamicin $X_2$,
9. 5-epi-amino-5-deoxy-Antibiotic G-418,
10. 5-epi-amino-5-deoxykanamycin A, and
11. 5-epi-amino-5-deoxygentamicin A.

EXAMPLE X

5-EPI-AZIDO-5-DEOXYAMINOGLYCOSIDES

A. 5-Epi-Azido-5-Deoxygentamicin $C_{1a}$

Reflux a solution of 1 gm. 1,3,2',6'-tetra-N-benzyloxycarbonyl-5-epi-azido-5-deoxy-2''-O-benzoyl-3'',4''-N,O-carbonylgentamicin $C_{1a}$ in 25 ml. 1:1 dioxane/water and 25 ml. 10% sodium hydroxide for 24 hours. Evaporate the solution to dryness, dissolve the residue in 10 ml. water and neutralize with acetic acid. Evaporate the solution, take up the residue in 5 ml. water and pass through 20 gm. of an Amberlite IRC-50 ($H^+$ form) resin column, wash the column with 200 ml. water and then with 100 ml. 1N ammonium hydroxide. Collect the ammonium hydroxide eluate and evaporate to a residue. Freeze dry the residue, (to produce a pale brown solid) then chromatograph on a 25 gm. silica gel column, eluting with chloroform:methanol:7% ammonium hydroxide (2:1:1) to obtain 186.4 mg. of 5-epi-azido-5-deoxygentamicin $C_{1a}$. Melting point = 115°–121° C $[\alpha]_D^{26}+$ 133.9.

B. In a similar manner, subject to the process described in Example XA equivalent quantities of the products of Example VIIIB and isolate the resultant products to obtain respectively,
1. 5-epi-azido-5-deoxygentamicin $C_1$, m.p. 95°–98° C, $[\alpha]_D^{26}+$ 129.5° (c 0.46, $H_2O$),
2. 5-epi-azido-5-deoxygentamicin $C_2$,
3. 5-epi-azido-5-deoxygentamicin $C_{2a}$,
4. 5-epi-azido-5-deoxygentamicin $C_{2b}$,
5. 5-epi-azido-5-deoxy-Antibiotic G-52, and
6. 5-epi-azido-5-deoxy-Antibiotic 66-40D.

C. 5-Epi-Azido-5-Deoxysisomicin

In a similar manner subject to the process described in Example XA an equivalent quantity of each of the products of Example VIIIC and isolate each of the resultant products to obtain 5-epi-azido-5-deoxysisomicin and 5-epi-azido-5-deoxyverdamicin.

D. In a manner similar to that described in Example XA, treat with 10% sodium hydroxide for 24 hours each of the per-N-protected-per-O-protected aminoglycosides prepared in Example VIIID. Further, treat each of the intermediates resulting from the sodium hydroxide treatment of compounds VIIID 1-7 and 9-12 with 80% acetic acid/water for 1 hour on the steam bath to remove any acetal or ketal protecting groups.

Isolate and purify each of the resultant products to obtain respectively,
1. 5-epi-azido-5,3',4'-trideoxykanamycin B,
2. 5-epi-azido-5-deoxygentamicin B,
3. 5-epi-azido-5-deoxygentamicin $B_1$,
4. 5-epi-azido-5-deoxy-Antibiotic JI-20A,
5. 5-epi-azido-5-deoxy-Antibiotic JI-20B,
6. 5-epi-azido-5-deoxykanamycin B,
7. 5-epi-azido-5-deoxytobramycin,
8. 5-epi-azido-5-deoxy-Antibiotic 66-40B,
9. 5-epi-azido-5-deoxygentamicin $X_2$,
10. 5-epi-azido-5-deoxy-Antibiotic G-418,
11. 5-epi-azido-5-deoxykanamycin A,
12. 5-epi-azido-5-deoxygentamicin A.

EXAMPLE XI

5-EPI-AMINO-5-DEOXYAMINOGLYCOSIDES VIA REDUCTION OF UNPROTECTED 5-EPI-AZIDO-5-DEOXYAMINOGLYCOSIDES

A. Subject the 5-epi-azido-5-deoxyaminoglycosides of Examples X-A, X-B(1-4) and X-D (1-7 and 9-12) to the hydrogenation process of Example IX-A to obtain the 5-epi-amino-5-deoxyaminoglycosides, respectively.

B. Subject the 5-epi-azido-5-deoxyaminoglycosides of Examples X-B (5 and 6), X-C and the X-D (8) to the reduction process of Example IX-C to obtain the 5-epi-amino-5-deoxyaminoglycosides, respectively.

EXAMPLE XII

1-N-ALKYL-5-EPI-AZIDO-5-DEOXY-PER-N-BENZYLOXYCARBONYL-O-HYDROCARBONCARBONYL-3'',4''-N,O-CARBONYL AMINOGLYCOSIDES

A. 1-N-Ethyl-5-Epi-Azido-5-Deoxy-O-Protected-N-Protected-Aminoglycosides

In the procedures of Example VIII(A-D) substitute for the starting compounds listed therein an equivalent quantity of the corresponding 1-N-ethyl derivative to obtain, respectively,
1. 1-N-ethyl-1,3,2',6'-tetra-N-benzyloxycarbonyl-5-epi-azido-5-deoxy-2''-O-benzoyl-3'',4''-N,O-carbonylgentamicin $C_{1a}$,
2. 1-N-ethyl-1,3,,2',6'-tetra-N-benzyloxycarbonyl-5-epi-azido-5-deoxy-2''-O-benzoyl-3'',4''-N,O-carbonylgentamicin $C_1$,
3. 1-N-ethyl-1,3,2',6'-tetra-N-benzyloxycarbonyl-5-epi-azido-5-deoxy-2''-O-benzoyl-3'',4''-N-O-carbonylgentamicin $C_2$,
4. 1-N-ethyl-1,3,2',6'-tetra-N-benzyloxycarbonyl-5-epi-azido-5-deoxy-2''-O-benzoyl-3'',4''-N,O-carbonylgentamicin $C_{2a}$,
5. 1-N-ethyl-1,3,2',6'-tetra-N-benzyloxycarbonyl-5-epi-azido-5-deoxy-2''-O-benzoyl-3'',4''-N,O-carbonylgentamicin $C_{2b}$,
6. 1-N-ethyl-1,3,2',6'-tetra-N-benzyloxycarbonyl-5-epi-azido-5-deoxy-2''-O-benzoyl-3'',4''-N,O-carbonyl-Antibiotic G-52,
7. 1-N-ethyl-1,3,2',6'-tetra-N-benzyloxycarbonyl-5-epi-azido-5-deoxy-2''-O-benzoyl-3'',4''-N,O-carbonyl-Antibiotic 66-40D,
8. 1-N-ethyl-1,3,2',6'-tetra-N-benzyloxycarbonyl-5-epi-azido-5-deoxy-2''-O-benzoyl-3'',4''-N,O-carbonylsisomicin,
9. 1-N-ethyl-1,3,2',6'-tetra-N-benzyloxycarbonyl-5-epi-azido-5-deoxy-2''-O-benzoyl-3'',4''-N,O-carbonylverdamicin,
10. -N-ethyl-1,3,2',6',3''-penta-N-benzoyloxycarbonyl-5-epi-azido-2''-O-benzoyl-4'',6''-O-benzylidene-5,3',4'-trideoxykanamycin B,
11. 1-N-ethyl-1,3-di-N-benzyloxycarbonyl-5-epi-azido-5-deoxy-2',3'-O-cyclohexylidene-6',4';3'',4''-di-N,O-carbonyl-2''-O-benzoylgentamicin B,
12. 1-N-ethyl-1,3-di-N-benzyloxycarbonyl-5-epi-azido-5-deoxy-2',3'-O-cyclohexylidene-6',4';3'',4''-di-N,O-carbonyl-2''-O-benzoylgentamicin $B_1$,
13. 1-N-ethyl-1,3,2',6'-tetra-N-benzyloxycarbonyl-5-epi-azido-5-deoxy-3',4'-O-benzylidene-2''-O-benzoyl-3'',4''-N,O-carbonyl-Antibiotic JI-20A,
14. 1-N-ethyl-1,3,2',6'-tetra-N-benzyloxycarbonyl-5-epi-azido-5-deoxy-3',4'-O-benzylidene-2''-O-benzoyl-3'',4''-N,O-carbonyl-Antibiotic JI-20B, 15. 1-N-ethyl-1,3,2',6',3'''-penta-N-benzyloxycarbonyl-5-epi-azido-5-deoxy-3',4';4'',6''-di-O-benzylidene-2''-O-benzoylkanamycin B,
16. 1-N-ethyl-1,3,2',6',3'''-penta-N-benzyloxycarbonyl-5-epi-azido-5-deoxy-4',2''-di-O-benzoyl-4'',6''-O-benzylidenetobramycin,
17. 1-N-ethyl-1,3,2',6',3'''-penta-N-benzyloxycarbonyl-5-epi-azido-5-deoxy-2'',4'''-di-O-benzoyl-Antibiotic 66-40B,
18. 1-N-ethyl-1,3,2'-tri-N-benzyloxycarbonyl-5-epi-azido-5-deoxy-3',2''-di-O-benzoyl-4',6'-O-cyclohexylidene-3'',4''-N,O-carbonylgentamicin $X_2$,
19. 1-N-ethyl-1,3,2'-tri-N-benzyloxycarbonyl-5-epi-azido-5-deoxy-3',2''-di-O-benzoyl-4',6'-O-cyclohexylidene-3'',4''-N,O-carbonyl-Antibiotic G-418,
20. 1-N-ethyl-1,3,6',3'''-tetra-N-benzyloxycarbonyl-5-epi-azido-5-deoxy-2',3';4'',6''-di-O-benzylidene-4',-2''-di-O-benzoylkanamycin A in admixture with 1-N-ethyl-1,3,6',3'''-tetra-N-benzyloxycarbonyl-5-epi-azido-5-deoxy-2',2''-di-O-benzoyl-3',4';4'',6''-di-O-benzylidenekanamycin A,
21. 1-N-ethyl-1,3,2',3'-tetra-N-benzyloxycarbonyl-5-epi-azido-5-deoxy-3',2'',4''-tri-O-benzoyl-4',6'-O-benzylidenegentamicin A.

B. Other 1-N-Alkyl-5-Epi-Azido-5-Deoxysisomicin Derivatives

1. In a manner similar to that described in Example XII-A treat an equivalent quantity of each of the following 1-N-alkylsisomicin derivatives (prepared from the corresponding 1-N-alkylsisomicin via the procedures of Examples I – IV) with sodium azide in dimethylformamide.
   1. 1-N-propyl-1,3,2',6'-tetra-N-benzyloxycarbonyl-5-O-methanesulfonyl-2''-O-benzoyl-3'',4''-N,O-carbonylsisomicin,
   2. 1-N-(n-butyl)-1,3,2',6'-tetra-N-benzyloxycarbonyl-5-O-methanesulfonyl-2''-O-benzoyl-3'',4''-N,O-carbonylsisomicin,
   3. 1-N-(δ-benzyloxycarbonylaminobutyl)-1,3,2',6'-tetra-N-benzyloxycarbonyl-5-O-methanesulfonyl-2''-O-benzoyl-3'',4''-N,O-carbonylsisomicin,
   4. 1-N-(γ-benzyloxycarbonylaminopropyl)-1,3,2',6'-tetra-N-benzyloxycarbonyl-5-O-methanesulfonyl-2''-O-benzoyl-3'',4''-N,O-carbonylsisomicin,
   5. 1-N-(β-methylpropyl)-1,3,2',6'-tetra-N-benzyloxycarbonyl-5-O-methanesulfonyl-2''-O-benzoyl-3'',-4''-N,O-carbonylsisomicin,
   6. 1-N-(n-pentyl)-1,3,2',6'-tetra-N-benzyloxycarbonyl-5-O-methanesulfonyl-2''O-benzoyl-3'',4''-N,O-carbonylsisomicin,
   7. 1-N-(γ-methylbutyl)-1,3,2',6'-tetra-N-benzyloxycarbonyl-5-O-methanesulfonyl-2''-O-benzoyl-3'',-4''-N,O-carbonylsisomicin,
   8. 1-N-(β-methylbutyl)-1,3,2',6'-tetra-N-benzyloxycarbonyl-5-O-methanesulfonyl-2''-O-benzoyl-3'',-4''-N,O-carbonylsisomicin,
   9. 1-N-(β,β-dimethylpropyl)-1,3,2',6'-tetra-N-benzyloxycarbonyl-5-O-methanesulfonyl-2''-O-benzoyl-3'',4''-N,O-carbonylsisomicin,
   1-N-(β-ethylbutyl)-1,3,2',6'-tetra-N-benzyloxycarbonyl-5-O-methanesulfonyl-2''-O-benzoyl-3'',4''-N,O-carbonylsisomicin,
   11. 1-N-(n-octyl)-1,3,2',6'-tetra-N-benzyloxycarbonyl-5O-methanesulfonyl-2''-O-benzoyl-3'',4''-N,O-carbonylsisomicin,
   12. 1-N-(β-propenyl)-1,3,2',6'-tetra-N-benzyloxycarbonyl-5-O-methanesulfonyl-2''-O-benzoyl-3'',4''-N,O-carbonylsisomicin,
   13. 1-N-(β-ethyl-β-hexenyl)-1,3,2',6'-tetra-N-benzyloxycarbonyl-5-O-methanesulfonyl-2''-O-benzoyl-3'',4''-N,O-carbonylsisomicin,
   14. 1-N-benzyl-1,3,2',6'-tetra-N-benzyloxycarbonyl-5-O-methanesulfonyl-2''-O-benzoyl-3'',4''-N,O-carbonylsisomicin,
   15. 1-N-phenethyl-1,3,2',6'-tetra-N-benzyloxycarbonyl-5-O-methanesulfonyl-2''-O-benzoyl-3'',4''-N,O-carbonylsisomicin,
   16. 1-N-cyclohexylmethyl-1,3,2',6'-benzyloxycarbonyl-5-O-methanesulfonyl-2''-O-benzoyl-3'',4''-N,O-carbonylsisomicin,
   17. 1-N-(δ-benzoyloxybutyl)-1,3,2',6'-tetra-N-benzyloxycarbonyl-5-O-methanesulfonyl-2''-O-benzoyl-3'',4''-N,O-carbonylsisomicin,
   18. 1-N-(ω-benzoyloxyoctyl)-1,3,2',6'-tetra-N-benzyloxycarbonyl-5-O-methanesulfonyl-2''-O-benzoyl-3'',4''-N,O-carbonylsisomicin,
   19. 1-N-(β-benzyloxycarbonylaminoethyl)-1,3,2',6'-tetra-N-benzyloxycarbonyl-5-O-methanesulfonyl-2''-O-benzoyl-3'',4''-N,O-carbonylsisomicin, 2. Isolate and purify each of the resultant products in a manner similar to that described in Example XII-A to obtain, respectively,
   1. 1-N-propyl-1,3,2',6'-tetra-N-benzoyloxycarbonyl-5-epi-azido-5-deoxy-2''-O-benzoyl-3'',4''-N,O-carbonylsisomicin,
   2. 1-N-(n-butyl)-1,3,2',6'-tetra-N-benzyloxycarbonyl-5-epi-azido-5-deoxy-2''-O-benzoyl-3'',4''-N,O-carbonylsisomicin,
   3. 1-N-(δ-benzyloxycarbonylaminobutyl)-1,3,2',6'-tetra-N-benzyloxycarbonyl-5-epi-azido-5-deoxy-2''-O-benzoyl-3'',4''-N,O-carbonylsisomicin,
   1-N-(γ-benzyloxycarbonylaminopropyl)-1,3,2',6'-tetra-N-benzyloxycarbonyl-5-epi-azido-5-deoxy-2''-O-benzoyl-3'',4''-N,O-carbonylsisomicin,
   5. 1-N-(β-methylpropyl)-1,3,2',6'-tetra-N-benzyloxycarbonyl-5-epi-azido-5-deoxy-2''-O-benzoyl-3'',4'λ'-N,O-carbonylsisomicin,
   6. 1-N-(n-pentyl)-1,3,2',6'-tetra-N-benzyloxycarbonyl-5-epi-azido-5-deoxy-2''-O-benzoyl-3'',4''-N,O-carbonylsisomicin,
   7. 1-N-(γ-methylbutyl)-1,3,2',6'-tetra-N-benzyloxycarbonyl-5-epi-azido-5-deoxy-2''-O-benzoyl-3'',4'λ'-N,O-carbonylsisomicin,
   8. 1-N-(β-methylbutyl)-1,3,2',6'-tetra-N-benzyloxycarbonyl-5-epi-azido-5-deoxy-2''-O-benzoyl-3'',4'λ'-N,O-carbonylsisomicin,
   9. 1-N-(β,β-dimethylpropyl)-1,3,2',6'-tetra-N-benzyloxycarbonyl-5-epi-azido-5-deoxy-2''-O-benzoyl-3'',4''-N,O-carbonylsisomicin,
   10. 1-N-(β-ethylbutyl)-1,3,2',6'-tetra-N-benzyloxycarbonyl-5-epi-azido-5-deoxy-2''-O-benzoyl-3'',4''-N,O-carbonylsisomicin,
   11. 1-N-(n-octyl)-1,3,2'6'-tetra-N-benzyloxycarbonyl-5-epi-azido-5-deoxy-2''-O-benzoyl-3'',4''-N,O-carbonylsisomicin,
   12. 1-N-(β-propyl)-1,3,2',6'-tetra-N-benzyloxycarbonyl-5-epi-azido-5-deoxy-2''-O-benzoyl-3'',4''-N,O-carbonylsisomicin,
   13. 1-N-(β-ethyl-βhexenyl)-1,3,2',6'-tetra-N-benzyloxycarbonyl-5-epi-azido-5-deoxy-2''-O-benzoyl-3'',4''-N,O-carbonylsisomicin,
   14. 1-N-benzyl-1,3,2',6'-tetra-N-benzyloxycarbonyl-5-epi-azido-5-deoxy-2''-O-benzoyl-3'',4''-N,O-carbonylsisomicin, 15. 1-N-phenethyl-1,3,2',6'-tetra-N-benzyloxycarbonyl-5-epi-azido-5-deoxy-2''-O-benzoyl-3'',4''-N,O-carbonylsisomicin,
16. 1-N-cyclohexylmethyl-1,3,2',6'-tetra-N-benzyloxycarbonyl-5-epi-azido-5-deoxy-2''-O-benzoyl-3'',4''-N,O-carbonylsisomicin,
17. 1-N-(δ-benzoyloxybutyl)-1,3,2',6'-tetra-N-benzyloxycarbonyl-5-epi-azido-5-deoxy-2''-O-benzoyl-3'',4''-N,O-carbonylsisomicin,
18. 1-N-(ω-benzoyloxyoctyl)-1,3,2',6'-tetra-N-benzyloxycarbonyl-5-epi-azido-5-deoxy-2''-O-benzoyl-3'',4''-N,O-carbonylsisomicin,
1-N-(β-benzyloxycarbonylaminoethyl)-1,3,2',6'-tetra-N-benzyloxycarbonyl-5-epi-azido-5-deoxy-2''-O-benzoyl-3'',4''-N,O-carbonylsisomicin, -N-ethyl- C. Other 1-N-Alkyl-5-Epi-Azido-5-Deoxy-O- and N-Protected Aminoglycosides In the procedure of Example XII-A substitute for the 1-N-ethyl-O-protected-N-protected starting compounds listed therein other 1-N-alkyl derivatives corresponding to the 1-N-substituted sisomicin starting compounds of Example XII-B to obtain the corresponding O-protected-N-protected-1-N-alkyl-5-epi-azido-4,6-di-O-(aminoglycosyl)-2,5-dideoxystreptamine.

B. 1-N-Alkyl-5-Epi-Azido-5-Deoxy Aminoglycosides

1. In a manner similar to that described in Example X-A treat each of the O-protected-N-protected-1-N-ethyl-5-epi-azido-5-deoxy aminoglycosides 1–9 prepared in Example XII-A with sodium hydroxide, and isolate and purify each of the resulting products in a manner similar to that described to obtain, respectively,
1. 1-N-ethyl-5-epi-azido-5-deoxygentamicin $C_{1a}$,
2. 1-N-ethyl-5-epi-azido-5-deoxygentamicin $C_1$,
3. 1-N-ethyl-5-epi-azido-5-deoxygentamicin $C_2$,
4. 1-N-ethyl-5-epi-azido-5-deoxygentamicin $C_{2a}$,
5. 1-N-ethyl-5-epi-azido-5-deoxygentamicin $C_{2b}$,
6. 1-N-ethyl-5-epi-azido-5-deoxy-Antibiotic G-52,
7. 1-N-ethyl-5-epi-azido-5-deoxy-Antibiotic 66-40D,
8. 1-N-ethyl-5-epi-azido-5-deoxysisomicin,
9. 1-N-ethyl-5-epi-azido-5-deoxyverdamacin.

2. In a manner similar to that described in Example X-D treat each of the O-protected-N-protected-1-N-ethyl-5-epi-azido-5-deoxy aminoglycoside products 10–21 prepared in Example XII-A with 10% sodium hydroxide followed by treatment with 80% acetic acid in water. Isolate and purify each of the resulting products in a manner similar to that to obtain, respectively,
10. 1-N-ethyl-5-epi-azido-5,3',4'-trideoxykanamycin B,
11. 1-N-ethyl-5-epi-azido-5-deoxygentamacin B,
12. 1-N-ethyl-5-epi-azido-5-deoxygentamacin $B_1$,
13. 1-N-ethyl-5-epi-azido-5-deoxy-Antibiotic-JI-20A,
14. 1-N-ethyl-5-epi-azido-5-deoxy-Antibiotic JI-20B,
15. 1-N-ethyl-5-epi-azido- 5-deoxykanamycin B,
16. 1-N-ethyl-5-azido-5-deoxytobramycin,
17. 1-N-ethyl-5epi-azido-5-deoxy-Antibiotic 66–40B,
18. 1-N-ethyl-5-epi-azido-5-deoxygentamicin $X_2$,
19. 1-N-ethyl-5-epi-azido-5-deoxy-Antibiotic G-418,
20. 1-N-ethyl-5-epi-azido-5-deoxykanamycin A,
21. 1-ethyl-5-epi-azido-5-deoxygentamicin A.

3. In a similar manner, subject to the process described in Example X-A an equivalent quantity of each of the products of Example XII-B and isolate each of the resultant products to obtain, respectively,
1. 1-N-propyl-5-epi-azido-5-deoxysisomicin,
2. 1-N-(n-butyl)-5-epi-azido-5-deoxysisomicin,
3. 1-N-(δ-aminobutyl)-5-epi-azido-5-deoxysisomicin,
4. 1-N-(γ-aminopropyl)-5-epi-azido-5-deoxysisomicin,
5. 1-N-(β-methylpropyl)-5-epi-azido-5-deoxysisomicin,
6. 1-N-(n-pentyl)-5-epi-azido-5-deoxysisomicin,
7. 1-N-(γ-methylbutyl)-5-epi-azido-5-deoxysisomicin,
8. 1-N-(β-methylbutyl)-5-epi-azido-5-deoxysisomicin,
9. 1-N-(β,β-dimethylpropyl)-5-epi-azido-5-deoxysisomicin,
10. 1-N-(β-ethylbutyl)-5-epi-azido-5-deoxysisomicin,
11. 1-N-(n-octyl)-5-epi-azido-5-deoxysisomicin,
12. 1-N-(β-propenyl)-5-epi-azido-5-deoxysisomicin,
13. 1-N-(β-ethyl-β-hexenyl)-5-epi-azido-5-deoxysisomicin,
14. 1-N-benzyl-5-epi-azido-5-deoxysisomicin,
15. 1-N-phenethyl-5-epi-azido-5-deoxysisomicin, -deoxysisomicin,
16. 1-N-cyclohexylmethyl-5-epi-azido-5-deoxysisomicin,
17. 1-N-(δ-hydroxybutyl)-5-epi-azido-5-deoxysisomicin,
18. 1-N-(ω-hydroxyoctyl)-5-epi-azido-5-deoxysisomicin,
19. 1-N-(β-aminoethyl)-5-epi-azido-5-deoxysisomicin.

4. In a similar manner by treating the products obtained according to the procedure of Example XII-C with aqueous sodium hydroxide followed by treatment with 80% aqueous acetic acid in the case of compounds having O-ylidene protecting groups to obtain the corresponding 1-N-alkyl-5-epi-azido-5-deoxy aminoglycoside free of O- and N-protecting groups.

EXAMPLE XIII

1-N-ALKYL-5-EPI-AMINO-5-DEOXY-AMINO-GLYCOSIDES

A. 1-N-Ethyl-5-Epi-Amino-5-Deoxy Aminoglycosides (1. Treat each of the O-protected-N-protected-1-N-ethyl-5-epi-azido-5-deoxy aminoglycosides prepared in Example XII-A and listed as products 1–5 therein with hydrogen in the presence of 30% palladium on charcoal in acetic acid in the manner of Example IX-A. Isolate each of the resulting products in a manner similar to that described followed by treatment with 2 N sodium hydroxide at 100° C and thence isolation and purification of the 5-epi-amino-5-deoxy compound to obtain, respectively,
1. 1-N-ethyl-5-epi-amino-5-deoxygentamicin $C_{1a}$,
2. 1-N-ethyl-5-epi-amino-5-deoxygentamicin $C_1$,
3 1-N-ethyl-5-epi-amino-5-deoxygentamicin $C_2$,
4. 1-N-ethyl-5-epi-amino-5-deoxygentamicin $C_{2a}$,
5. 1-N-ethyl-5-epi-amino-5-deoxygentamicin $C_{2b}$.

2. In the manner of Example IX-C treat equivalent quantities of each of the 5-epi-azido-5-deoxy products 6–9 and 17 of Example XII-A with sodium in liquid ammonia and isolate and purify each of the resultant products in the described manner to obtain, respectively,
1. 1-N-ethyl-5-epi-amino-5-deoxy Antibiotic G-52,
2. 1-N-ethyl-5-epi-amino-5-deoxy-Antibiotic 66-40D,
3. 1-N-ethyl-5-epi-amino-5-deoxysisomicin,
4. 1-N-ethyl-5-epi-amino-5-deoxyverdamicin,
5. 1-N-ethyl-5-epi-amino-5-deoxy-Antibiotic 66-40B.

3. Treat each of the 1-N-ethyl-5-epi-azido-5-deoxy-0-protected-N-protected aminoglycosides prepared in 10-16 and 18-21 of Example XII-A in acetic acid with hydrogen in the presence of palladium on charcoal in the manner of Example IX-A. Treat the resulting products first with 2 N sodium hydroxide followed by treatment with 80% acetic acid in water in the manner described in Example IX-D. Isolate and purify each of the resultant products in a manner similar to that to obtain, respectively, 1. 1-N-ethyl-5-epi-amino-5,3',4'-trideoxykanamycin B,
2. 1-N-ethyl-5-epi-amino-5-deoxygentamicin B,
3. 1-N-ethyl-5-epi-amino-5-deoxygentamicin $B_1$,
4. 1-N-ethyl-5-epi-amino-5-deoxy-Antibiotic JI-20A,
5. 1-N-ethyl-5-epi-amino-5-deoxy-Antibiotic JI-20B,
6. 1-N-ethyl-5-epi-amino-5-deoxykanamycin B,
7. 1-N-ethyl-5-epi-amino-5-deoxytobramycin,
8. 1-N-ethyl-5-epi-amino-5-deoxygentamicin $X_2$,
9. 1-N-ethyl-5-epi-amino-5-deoxy-Antibiotic G-418,
10. 1-N-ethyl-6-epi-amino-5-deoxykanamycin A,
11. 1-N-ethyl-5-epi-amino-5-deoxygentamicin A.

B. Other 1-N-Alkyl-5-Epi-Amino-5-Deoxysisomicins

Treat an equivalent quantity of each of the 0-substituted-N-substituted-1-N- -alkyl-5-epi-azido-5-deoxysisomicin derivatives prepared in Example XII-B with sodium in liquid ammonia in a manner similar to that described in Example IX-C. Isolate and purify each of the resultant products in a manner similar to that to obtain, respectively, 1. 1-N-propyl-5-epi-amino-5-deoxysisomicin,
2. 1-N-(n-butyl)-5-epi-amino-5-deoxysisomicin,
3. 1-N-(δ-aminobutyl)-5-epi-amino-5-deoxysisomicin,
4. 1-N-(γ-aminopropyl)-5-epi-amino-5-deoxysisomicin,
5. 1-N-(β-methylpropyl)-5-epi-amino-5-deoxysisomicin,
6. 1-N-(n-pentyl)-5-epi-amino-5-deoxysisomicin,
7. 1-N-(γ-methylbutyl)-5-epi-amino-5-deoxysisomicin,
8. 1-N-(β-methylbutyl)-5-epi-amino-5-deoxysisomicin,
9. 1-N-(β,β-dimethylpropyl)-5-epi-amino-5-deoxysisomicin,
10. 1-N-(β-ethylbutyl)-5-epi-amino-5-deoxysisomicin,
11. 1-N-(n-octyl)-5-epi-amino-5-deoxysisomicin,
12. 1-N-(β-propenyl)-5-epi-amino-5-deoxysisomicin,
13. 1-N-(β-ethyl-β-hexenyl)-5-epi-amino-5-deoxysisomicin,
14. 1-N-benzyl-5-epi-amino-5-deoxysisomicin,
15) 1-N-phenethyl-5epi-amino-5-deoxysisomicin.
16. 1-N-cyclohexylmethyl-5-epi-amino-5-deoxysisomicin,
17. 1-N-(δ-hydroxybutyl)-5-epi-amino-5-deoxysisomicin,
18. 1-N-(ω-hydroxyoctyl)-5-epi-amino-5-deoxysisomicin,
19. 1-N-(β-aminoethyl)-5-epi-amino-5-deoxysisomicin.

C. Other 1-N-Alkyl-5-Epi-Amino-5-Deoxy Aminoglycosides

1. In the procedure of Example XII-A (1 and 2) substitute for the 1-N-ethyl-0-protected-N-protected-5-epi-azido-5-deoxy aminoglycoside intermediates therein, other 1-N-alkyl derivatives of the aminoglycosides listed therein corresponding to the 1-N-substituted sisomicin starting compounds of Example XII-B to obtain the corresponding 1-N-alkyl-5-epi-amino-4,6-di-0-(aminoglycosyl)-2,5-dideoxystreptamine.

PREPARATION OF 1-N-ALKYL DERIVATIVES OF 5-EPI-AZIDO- AND 5-EPI-AMINO-4,6-DI-0-(AMINOGLYCOSYL)-2,5-DIDEOXYSTREPTAMINES VIA REDUCTION OF THE CORRESPONDING 1-N-ACYL DERIVATIVES

EXAMPLE XIV

1-N-ACYL-5-EPI-AZIDO- AND 1-N-ACYL-5-EPI-AMINO-4,6-DI-0-(AMINOGLYCOSYL)-2,5-DIDEOXYSTREPTAMINES

A. 1-N-Acetyl-5-Epi-Azido-5-Deoxysisomicin

Dissolve 1.25 gm. of 5-epi-azido-5-deoxysisomicin sulfate in 200 ml. of water/methanol (2:3 v/v) and chill the solution. Add 1.5 ml. of acetic anhydride and after approximately 10 minutes, add 0.125 ml. of triethylamine in 10 ml. of methanol over a 15 minute interval. Allow the reaction mixture to warm to room temperature over a 2 hour interval, then evaporate the solvent in vacuo. Dissolve the residue in water, and convert the product to the free base by passage of an aqueous solution thereof through Amberlite IRA-401S resin in the hydroxide ion cycle. Lyophilize the column eluate and chromatograph the residue on 50 gm. of silica gel using the lower phase of (2:1:1) chloroform:methanol: 7% ammonium hydroxide solvent system as eluant. Monitor the fractions via thin layer chromatography and combine like fractions and evaporate to a residue comprising 1-N-acetyl-5-epi-azido-5-deoxysisomicin.

B. Other 1-N-Acetyl-5-Epi-Azido and 1-N-Acetyl-5-Epi-Amino-4,6-Di-0-(Aminoglycosyl)-2,5-Dideoxystreptamines In similar manner treat an equivalent quantity of the sulfate salt of the following 5-epi-azido- and 5-epi-amino-4,6-di-0-(aminoglycosyl)-2,5-dideoxystreptamines to the process of Example XIV-A.

1. 5-epi-amino-5-deoxysisomicin,
2. 5-epi-azido-5-deoxygentamicin $C_{1a}$,
3. 5-epi-amino-5-deoxygentamicin $C_{1a}$,
4. 5-epi-azido-5-deoxygentamicin $C_1$,
5. 5-epi-amino-5-deoxygentamicin $C_1$,
6. 5-epi-azido-5-deoxygentamicin $C_2$,
7. 5-epi-amino-5-deoxygentamicin $C_2$,
8. 5-epi-azido-5-deoxygentamicin $C_{2a}$,
9. 5-epi-amino-5-deoxygentamicin $C_{2a}$,
10. 5-epi-azido-5-deoxygentamicin $C_{2b}$,
11. 5-epi-amino-5-deoxygentamicin $C_{2b}$,
12. 5-epi-azido-5-deoxy-Antibiotic G-52,
13. 5-epi-amino-5-deoxy-Antibiotic G-52,
14. 5-epi-azido-5-deoxy-Antibiotic 66-40D,
15. 5-epi-amino-5-deoxy-Antibiotic 66-40D,
16. 5-epi-azido-5-deoxyverdamicin,
17. 5-epi-amino-5-deoxyverdamicin,
18. 5-epi-azido-5,3',4'-trideoxykanamycin B,
19. 5-epi-amino-5,3',4'-trideoxykanamycin B,
20. 5-epi-azido-5-deoxygentamicin B,
21. 5-epi-amino-5-deoxygentamicin B,
22. 5-epi-azido-5-deoxygentamicin $B_1$,
23. 5-epi-amino-5-deoxygentamicin $B_1$,
24. 5-epi-azido-5-deoxy-Antibiotic JI-20A,
25. 5-epi-amino-5-deoxy-Antibiotic JI-20A,
26. 5-epi-azido-5-deoxy-Antibiotic JI-20B,
27. 5-epi-amino-5-deoxy-Antibiotic JI-20B,
28. 5-epi-azido-5-deoxykanamycin B,
29. 5-epi-amino-5-deoxykanamycin B,
30. 5-epi-azido-5-deoxytobramycin,
31. 5-epi-amino-5-deoxytobramycin,
32. 5-epi-azido-5-deoxy-Antibiotic 66-40B, 33. 5-epi-amino-5-deoxy-Antibiotic 66-40B,
34. 5-epi-azido-5-deoxygentamicin $X_2$,
35. 5-epi-amino-5-deoxygentamicin $X_2$,
36. 5-epi-azido-5-deoxy-Antibiotic G-418,
37. 5-epi-amino-5-deoxy-Antibiotic G-418,
38. 5-epi-azido-5-deoxykanamycin A,
39. 5-epi-amino-5-deoxykanamycin A,
40. 5-epi-azido-5-deoxygentamicin A,
41. 5-epi-amino-5-deoxygentamicin A.

Isolate and purify each of the resulting products in the manner described in Example XIV-A to obtain the corresponding 1-N-acetyl derivatives of each of the foregoing starting compounds. C. In the procedures of Examples XIV-A and B by substituting other acid anhydrides, e.g. propionic acid anhydride, N-octanoic acid anhydride, phenyl acetic acid anhydride and trans-$\beta$-phenylacrylic acid anhydride there is obtained the corresponding 1-N-acyl derivatives, e.g. 1-N-propionyl, 1-N-(n-octanoyl), 1-N-phenylacetyl and 1-N-(trans$\beta$-phenylpropenoyl) of the 5-epi-azido- and 5-epi-amino-4,6-di-O-(aminoglycosyl)-2,5-dideoxystreptamine starting compounds listed therein, respectively.

D. 1-N-(5-Aminopentanoyl)-5-Epi-Azido- (and 5-Epi-Amino)-4,6-Di-O-(Aminoglycosyl)-2,5-Dideoxystreptamines 1. 1-N-(5-Aminopentanoyl)-5-Epi-Azido-5-Deoxysisomicin
    a. 1-N-(5-Phthalimidopentanoyl)-5-Epi-Azido-5-Deoxysisomicin Dissolve 2.5 g. of 5-epi-azido-5-deoxysisomicin sulfate in 250 ml. of water and add 100 ml. of methanol. Add 0.35 g. of triethylamine and stir for 10 minutes. Add a solution of 1.2 g. N-(5-phthalimidopentanoyloxy)succinimide in 20 ml. of dry dimethylformamide dropwise with stirring to the solution of the antibiotic. Stir the mixture at ambient temperature for 16 hours. Concentrate the reaction mixture to a residue in vacuo and triturate the residue with methanol to yield 3.4 g. of white solids. Chromatograph the residue on 200 g. of silica gel in the lower phase of a chloroform:methanol:7% ammonium hydroxide (2:1:1) system to give 1-N-(5-phthalimidopentanoyl)-5-epi-azido-5-deoxysisomicin.

b. 1-N-(5-Aminopentanoyl)-5-Epi-Azido-5-Deoxysisomicin

Heat 0.4 gm. of 1-N-(5-phthalimidopentanoyl)-5-epi-azido-5-deoxysisomicin in 5 ml. of 5% ethanolic hydrazine hydrate under reflux for 4 hours. Concentrate the solution and add tetrahydrofuran to precipitate 1-N-(5-aminopentanoyl)-5-epi-azido-5-deoxysisomicin, which is collected by filtration.

2. In similar manner treat an equivalent quantity of the acid addition salt of each 5-epi-azido-5-deoxy aminoglycoside and 5-epi-amino-5-deoxy aminoglycoside starting compounds listed in Example XIV-B to the process of Example XIV-D(1). Isolate and purify each of the resultant products in a manner similar to that described to obtain the corresponding 1-N-(5-aminopentanoyl)-5-epi-azido-5-deoxy aminoglycoside and 1-N-(5-aminopentanoyl)-5-epi-amino-5-deoxy aminoglycoside derivative of each of the listed 5-epi-azido- and 5-epi-amino-5-deoxy starting compounds.

E. 1-N-(5-Hydroxypentanoyl)-5-Epi-Azido- (and 5-Epi-Amino)-4,6-Di-O-(Aminoglycosyl)-2,5-Dideoxystreptamines 1. 1-N-(5-Hydroxypentanoyl)-5-Epi-Azido-5-Deoxysisomicin Dissolve 2.5 g. of 5-epi-azido-5-deoxysisomicin in 250 ml. of water and add 100 ml. of methanol. Add 0.35 g. of triethylamine and stir for fifteen minutes. Add a solution of 1.0 g. of N-(5-acetoxypentanoyloxy)succinimide with stirring to the solution of the antibiotic, and stir at ambient temperature for 16 hours. Evaporate the solution in vacuo to leave a solid residue. Dissolve the residue in 5 ml. of 5% ethanolic hydrazine hydrate and heat under reflux for fifteen minutes. Concentrate the solution in vacuo to leave an oily residue and chromatograph it on 200 g. silica gel in the lower phase of a solvent system consisting of chloroform:methanol:7% ammonium hydroxide (2:1:1) to give 1-N-(5-hydroxypentanoyl)-5-epi-azido-5-deoxysisomicin.

2. In similar manner treat an equivalent quantity of the acid addition salt of those 5-epi-azido (and 5-epi-amino-)-5-deoxy aminoglycoside starting compounds set forth in Example XIV-B to the procedure of Example XIV-E(1). Isolate and purify the resultant products in a manner similar to that described to obtain 1. 1-N-(5-hydroxypentanoyl)-5-epi-amino-5-deoxysisomicin,
2. 1-N-(5-hydroxypentanoyl)-5-epi-azido-5-deoxygentamicin $C_{1a}$,
3. 1-N-(5-hydroxypentanoyl)-5-epi-amino-5-deoxygentamicin $C_{1a}$,
4. 1-N-(5-hydroxypentanoyl)-5-epi-azido-5-deoxygentamicin $C_1$,
5. 1-N-(5-hydroxypentanoyl)-5-epi-amino-5-deoxygentamicin $C_1$,
6. 1-N-(5-hydroxypentanoyl)-5-epi-azido-5-deoxygentamicin $C_2$,
7. 1-N-(5-hydroxypentanoyl)-5-epi-amino-5-deoxygentamicin $C_2$,
8. 1-N-(5-hydroxypentanoyl)-5-epi-azido-5-deoxygentamicin $C_{2a}$,
9. 1-N-(5-hydroxypentanoyl)-5-epi-amino-5-deoxygentamicin $C_{2a}$,
10. 1-N-(5-hydroxypentanoyl)-5-epi-azido-5-deoxygentamicin $C_{2b}$,
11. 1-N-(5-hydroxypentanoyl)-5-epi-amino-5-deoxygentamicin $C_{2b}$,
12. 1-N-(5-hydroxypentanoyl)-6-epi-azido-5-deoxy-Antibiotic G-52,
13. 1-N-(5-hydroxypentanoyl)-5-epi-amino-5-deoxy-Antibiotic G-52,
14. 1-N-(5-hydroxypentanoyl)-5-epi-azido-5-deoxy-Antibiotic 66-40D,
15. 1-N-(5-hydroxypentanoyl)-5-epi-amino-5-deoxy-Antibiotic 66-40D,
16. 1-N-(5-hydroxypentanoyl)-5-epi-azido-5-deoxyverdamicin,
17. 1-N-(5-hydroxypentanoyl)-5-epi-amino-5-deoxyverdamicin,
18. 1-N-(5-hydroxypentanoyl)-5-epi-azido-5,3',4'-trideoxykanamycin B,
19. 1-N-(5-hydroxypentanoyl)-5-epi-amino-5,3',4'-trideoxykanamycin B,
20. 1-N-(5-hydroxypentanoyl)-5-epi-azido-5-deoxygentamicin B,
21. 1-N-(5-hydroxypentanoyl)-5-epi-amino-5-deoxygentamicin B,
22. 1-N-(5-hydroxypentanoyl)-5-epi-azido-5-deoxygentamicin $B_1$,
23. 1-N-(5-hydroxypentanoyl)-5-epi-amino-5-deoxygentamicin $B_1$,
24. 1-N-(5-hydroxypentanoyl)-5-epi-azido-5-deoxy-Antibiotic JI-20A, 25. 1-N-(5-hydroxypentanoyl)-5-epi-amino-5-deoxy-Antibiotic JI-20A,
26. 1-N-(5-hydroxypentanoyl)-5-epi-azido-5-deoxy-Antibiotic JI-20B,
27. 1-N-(5-hydroxypentanoyl)-5-epi-amino-5-deoxy-Antibiotic JI-20B,
28. 1-N-(5-hydroxypentanoyl)-5-epi-azido-5-deoxykanamycin B,
29. 1-N-(5-hydroxypentanoyl)-5-epi-amino-5-deoxykanamycin B,
30. 1-N-(5-hydroxypentanoyl)-5-epi-azido-5-deoxytobramycin, 1
31. 1-N-(5-hydroxypentanoyl)-5-epi-amino-5-deoxytobramycin,
32. 1-N-(5-hydroxypentanoyl)-5-epi-azido-5-deoxy-Antibiotic 66-40B,
33. 1-N-(5-hydroxypentanoyl)-5-epi-amino-5-deoxy-Antibiotic 66-40B,
34. . 1-N-(5-hydroxypentanoyl)-5-epi-azido-5-deoxygentamicin $X_2$,
35. 1-N-(5-hydroxypentanoyl)-5-epi-amino-5-deoxygentamicin $X_2$,
36. 1-N-(5-hydroxypentanoyl)-5-epi-azido-5-deoxy-Antibiotic G-418,
37. 1-N-(5-hydroxypentanoyl)-5-epi-amino-5-deoxy-Antibiotic G-418,
38. 1-N-(5hydroxypentanoyl)-5-epi-azido-5-deoxykanamycin A,
39. 1-N-(5-hydroxypentanoyl)-5-epi-amino-5-deoxykanamycin A,
40. 1-N-(5-hydroxypentanoyl)-5-epi-azido-5-deoxygentamicin A,
41. 1-N-(5-hydroxypentanoyl)-5-epi-amino-5-deoxygentamicin A.

F. 1-N-Formyl-5-Epi-Azido- -epi-amino-5-Epi-Amino-4,6-Di-O-(Aminoglycosyl)-2,5-Dideoxystreptamines 1. 1-N-Formyl-5-Epi-Azido-5-Deoxysisomicin Dissolve 2.5 gm. of 5-epi-azido-5-deoxysisomicin sulfate in 250 ml. of water and add 100 ml. of methanol. Add 0.35 g. of triethylamine and stir for 10 minutes. Add a solution of 2.0 gm. of N-formyloxysuccinimide in 20 ml. of dry dimethylformamide dropwise with stirring. Stir the reaction mixture at room temperature for 16 hours. Concentrate the reaction mixture in vacuo to a residue. Triturate the residue with methanol, filter and dry the resultant solid to obtain 1-N-formyl-5-epi-azido-5-deoxysisomicin.

2. In similar manner treat an equivalent quantity of the acid addition salt of the 5-epi-azido- and 5-epi-amino-5-deoxy aminoglycoside starting compounds of Example XIV-B to the process described in Example XIV-F(1). Isolate and purify the resultant products in a manner similar to that described to obtain the corresponding 1-N-formyl derivatives.

G. 1-N-(Aminohydroxyacyl)-5-Epi-Azido- (and 5-Epi-Amino)-4,6-Di-O-(Aminoglycosyl)-2,5-Dideoxystreptamines 1. 1-N-(S-4-Amino-2-Hydroxybutyryl)-5-Epi-Amino-5-Deoxygentamicin $C_{1a}$ a. 1-N-(S-4-Benzyloxycarbonylamino-2-Hydroxybutyryl)-5-Epi-Azido-5-Deoxygentamicin $C_{1a}$ Dissolve 2.8 g. (4 mmoles) of 5-epi-azido-5-deoxygentamicin $C_{1a}$ sulfate in 30 ml. of water and add 15 ml. of methanol. Add 0.56 ml. (4 mmoles) of triethylamine and stir for 10 minutes. Add a solution containing 4 mmoles of N-(S-4-benzyloxycarbonylamino-2-hydroxybutyryloxy)succinimide in 20 ml. of dry dimethylformamide dropwise with stirring to the antibiotic solution. Stir the mixture overnight (16 hours) at ambient temperature. Thin layer chromatography of the reaction mixture on silica gel using the lower phase of a solvent system consisting of chloroform:methanol:ammonium hydroxide (1:1:1), shows the presence of a plurality of minor components and one major component. Concentrate the reaction mixture to a residue in vacuo nd triturate the residue with methanol to yield 3.2 g. of white solids containing 1-N-(S-4-benzyloxycarbonylamino-2-hydroxybutyryl)-5-epi-azido-5-deoxygentamicin $C_{1a}$.

b. 1-N-(S-4-Amino-2-Hydroxybutyryl)-5-Epi-Amino-5-Deoxygentamicin $C_{1a}$

Dissolve the product of Example XIV-G(1a) in a mixture consisting of 12 ml. of methanol and 3 ml. of water, add 20 mg. of 10% palladium on carbon and hydrogenate at 4 atmospheres at room temperature. After 3 hours the reaction is essentially complete. Remove the catalyst by filtration and lyophilize the filtrate and obtain 1-N-(S-4-amino-2-hydroxybutyryl)-5-epi-amino-5-deoxygentamicin $C_{1a}$.

2. 1-N-(S-4-Amino-2-Hydroxybutyryl)-5-Epi-Amino-5-Deoxygentamicin B a. 1-N-(S-4-Benzyloxycarbonylamino-2-Hydroxybutyryl)-5-Epi-Amino-5-Deoxygentamicin B Dissolve 3.39 g. of 5-epi-amino-5-deoxygentamicin B sulfate in 48.4 ml. of water and dilute with 23.7 ml. of methanol. Add 0.7 ml. of triethylamine dropwise with stirring. Dissolve 1.67 g. of N-(S-4-benzyloxycarbonylamino-2-hydroxybutyryloxy)succinimide in dimethylformamide and add the solution dropwise with stirring to the antibiotic solution. Stir the resulting solution at room temperature for 18 hours, then concentrate to a residue in vacuo. Dissolve the residue in water and treat with dilute barium hydroxide solution with stirring until the pH reaches about 8.0. Remove the precipitated barium sulfate by filtration using a filter aid. Wash the precipitate with water, combine the filtrate and washings and concentrate to dryness in vacuo. Chromatograph the residue on a column containing 600 g. of silica gel using the lower phase of a solvent system consisting of chloroform:methanol:ammonium hydroxide (1:1:1) as the eluant. Combine the like fractions containing the 1-N-(S-4-benzyloxycarbonylamino-2-hydroxybutyryl)-5-epi-amino-5-deoxygentamicin B as determined by thin layer chromatography and concentrate the combined fractions to a residue comprising 1-N-(S-4-benzyloxycarbonylamino-2-hydroxybutyryl)-5-epi-amino-5-deoxygentamicin B.

b. 1-N-(S-4-Amino-2-Hydroxybutyryl)-5-Epi-Amino-5-Deoxygentamicin B

Dissolve the product of above Example XIV-G(2a) in a mixture consisting of 20 ml. of water and 8 ml. of methanol. Hydrogenate the product in the presence of 60 mg. of 5% palladium-on-carbon at 3.5 atmospheres and room temperature for 3 hours. Remove the catalyst by filtration through a filter aid. Wash the filter pad with water and combine the filtrate and washings. Concentrate the combined filtrate and washings to dryness in vacuo. Chromatograph the residue on a silica gel column containing 100 g. of silica gel using a solution consisting of chloroform:methanol:ammonium hydroxide (1:2:1) as the eluant. Fractions containing the most polar component are polled, concentrated and lyophilized to give 1-N-(S-4-amino-2-hydroxybutyryl)-5-epi-amino-5-deoxygentamicin B.

3. 1-N-(S-4-Amino-2-Hydroxybutyryl)-5-Epi-Azido-5-Deoxyverdamicin a. 1-N-(S-4-Phthalimido-2-Hydroxybutyryl)-5-Epi-Azido-5-Deoxyverdamicin Dissolve 5.00 g. of 5-epi-azido-5-deoxyverdamicin sulfate in 50 ml. of water and add 25 ml. of methanol. Add 0.50 ml. of triethylamine and stir for 10 minutes. Add a solution containing 2.5 g of N-(S-4-phthalimido-2-hydroxybutyryloxy)succinimide in 10 ml. of dimethylformamide dropwise with stirring. Stir the mixture overnight at ambient temperature then concentrate to a residue in vacuo. Chromatograph the residue over 160 g. of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain thereby 1-N-(S-4-phthalimido-2-hydroxybutyryl)-5-epi-azido-5-deoxyverdamicin.

b. 1-N-(S-4-Amino-2-Amino-2-Hydroxybutyryl)-5-Epi-Azido-5-Deoxyverdamicin

Dissolve the product of Example XIV-G(3a) in 40 ml. of ethanol and add 0.2 g. of hydrazine hydrate. Reflux the solution for 3 hours, then evaporate to dryness in vacuo. Chromatograph the residue over 160 g. of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain thereby 1-N-(S-4-amino-2-hydroxybutyryl)-5-epi-azido-5-deoxyverdamicin.

4. In the procedures of Examples XIV-G(1-3) equivalent quantities of the sulfate salts of other 5-epi-azido- (or 5-epi-amino)4,6-di-O-(aminoglycosyl)-2,5-dideoxystreptamines may be substituted for 5-epi-azido-5-deoxygentamicin $C_{1a}$, 5-epi-amino-5-deoxygentamicin B, and 5-epi-azido-5-deoxyverdamicin, and other N-(benzyloxycarbonylaminohydroxyacyloxy)succinimides may be substituted for N-(S-4-benzyloxycarbonylamino-2-hydroxybutyryloxy)succinimide or N-(S-4-phthalimido-2-hydroxybutyryloxy)succinimide and there will be obtained the corresponding 1-N-(aminohydroxyacyl)-5-epi-azido- (or 5-epi-amino)4,6-di-O-(aminoglycosyl)-2,5-dideoxystreptamine.

EXAMPLE XV

1-N-ALKYL-5-EPI-AMINO-4,6-DI-O-(AMINO-GLYCOSYL)-2,5-DIDEOXYSTREPTAMINES PREPARED BY HYDRIDE REDUCTION OF THE CORRESPONDING 1-N-ACYL DERIVATIVES

A. 1-N-(S-Aminohydroxyalkyl)-5-Epi-Amino-5-Deoxy Aminoglycosides 1. 1-N-(S-δ-Amino-β-Hydroxybutyl)-5-Epi-Amino-5-Deoxygentamicin $C_1$ Suspend 98 mg. of 1-N-(S-amino-2-hydroxybutyryl)-5-epi-amino-5-deoxygentamicin $C_1$ in 8 ml. of tetrahydrofuran. Add 14 ml. of 1 M diborane in tetrahydrofuran and heat at reflux temperature for 6 hours under an atmosphere of nitrogen. Carefully add 2 ml. of water to decompose any excess diborane and evaporate. Dissolve the resultant residue in hydrazine hydrate and heat at reflux temperature under an atmosphere of nitrogen for 16 hours. Evaporate the solution and extract the residue with hot aqueous ethanol. Evaporate the combined ethanol extracts and chromatograph the resultant residue over 10 ml. of silica gel eluting with the lower phase of a chloroform:methanol:concentrated ammonium hydroxide (2:1:1) solvent system. Combine and evaporate the like fractions as determined by thin layer chromatography to obtain 1-N-(S-δ-amino-β-hydroxybutyl)-5-epi-amino-5-deoxygentamicin $C_1$.

2. In the above procedure substitute 1-N-(S-3-amino-2-hydroxypropionyl)-5-epi-amino-5-deoxygentamicin $C_1$ for 1-N-(S-4-amino-2-hydroxybutyryl)-5-epi-amino-5-deoxygentamicin $C_1$ to obtain 1-N-(S-γ-amino-β-hydroxypropyl)-5-epi-amino-5-deoxygentamicin $C_1$.

3. Treat each of the following 1-N-(S-4-amino-2-hydroxybutyryl)-5-epi-amino-4,6-di-O-(aminoglycosyl)-2,5-dideoxystreptamines with diborane in tetrahydrofuran in the manner described in Example XV-A(1).

1. 1-N-(S-4-amino-2-hydroxybutyryl)-5-epi-amino-5-deoxygentamicin A,
2. 1-N-(-4-amino-2-hydroxybutyryl)-5-epi-amino-5-deoxygentamicin B,
3. 1-N-(S-4-amino-2-hydroxybutyryl)-5-epi-amino-5-deoxygentamicin $B_1$,
4. 1-N-(S-4-amino-2-hydroxybutyryl)-5-epi-amino-5-deoxygentamicin $C_{1a}$,
5. 1-N-(S-4-amino-2-hydroxybutyryl)-5-epi-amino-5-deoxygentamicin $C_2$,
6. 1-N-(S-4-amino-2-hydroxybutyryl)-5-epi-amino-5-deoxygentamicin $C_{2a}$,
7. 1-N-(S-4-amino-2-hydroxybutyryl)-5-epi-amino-5-deoxygentamicin $C_{2b}$,
8. 1-N-(S-4-amino-2-hydroxybutyryl)-5-epi-amino-5-deoxygentamicin $X_2$,
9. 1-N-(S-4-amino-2-hydroxybutyryl)-5-epi-amino-5-deoxytobramycin,
10. 1-N-(S-4-amino-2-hydroxybutyryl)-5-epi-amino-5-deoxy-Antibiotic G-418,
11. 1-N-(S-4-amino-2-hydroxybutyryl)-5-epi-amino-5-deoxy-Antibiotic JI-20A,
12. 1-N-(S-4-amino-2-hydroxybutyral)-5-epi-amino-5-deoxy-Antibiotic JI-20B,
13. 1-N-(S-4-amino-2-hydroxybutyryl)-5-epi-amino-5,3',4'-trideoxykanamycin B,
14. 1-N-(S-4-amino-2-hydroxybutyryl)-5-epi-amino-5-deoxykanamycin B,
15. 1-N-(S-4-amino-2-hydroxybutyryl)-5-epi-amino-5-deoxykanamycin A, Isolate and purify each of the resultant products in a manner similar to that described in Example XV-A(1) to obtain, respectively, 1. 1-N-(S-δ-amino-β-hydroxybutyl)-5-epi-amino-5-deoxygentamicin A,
2. 1-N-(S-δ-amino-β-hydroxybutyl)-5-epi-amino-5-deoxygentamicin B,
3. 1-N-(S-δ-amino-β-hydroxybutyl)-5-epi-amino-5-deoxygentamicin $B_1$,
4. 1-N-(S-δ-amino-β-hydroxybutyl)-5-epi-amino-5-deoxygentamicin $C_{1a}$,
5. 1-N-(S-δ-amino-β-hydroxybutyl)-5-epi-amino-5-deoxygentamicin $C_2$,
6. 1-N-(S-δ-amino-β-hydroxybutyl)-5-epi-amino-5-deoxygentamicin $C_{2a}$,
7. 1-N-(S-δ-amino-β-hydroxybutyl)-5-epi-amino-5-deoxygentamicin $C_{2b}$,
8. 1N-(S-δ-amino-β-hydroxybutyl)-5-epi-amino-5-deoxygentamicin $X_2$,
9. 1-N-(S-δ-amino-β-hydroxybutyl)-5-eip-amino-5-deoxytobramycin,
10. 1-N-(S-δ-amino-β-hydroxybutyl)-5-epi-amino-5-deoxy-Antibiotic G-418, 11. 1-N-(S-δ-amino-β-hydroxybutyl)-5-epi-amino-5-deoxy-Antibiotic JI-20A,
12. 1-N-(S-δ-amino-β-hydroxybutyl)-5-epi-amino-5-deoxy-Antibiotic Ji-20B,
13. 1-N-(S-δ-amino-β-hydroxybutyl)-5-epi-amino-5,3',4'-trideoxykanamycin B,
14. 1-N-(S-δ-amino-β-hydroxybutyl)-5-epi-amino-5-deoxykanamycin B,
15. 1-N-(S-δ-amino-β-hydroxybutyl)-5-epi-amino-5-deoxykanamycin A.

4. In the procedure of Example XV-A(2) hereinabove utilize as starting compounds the corresponding 1-N-(S-3-amino-2-hydroxypropionyl) derivatives to obtain the corresponding 1N-(S-γ-amino-β-hydroxypropyl) derivatives, i.e.

1. 1-N-(S-γ-amino-β-hydroxypropyl)-5-epi-amino-5-deoxygentamicin A,
2. 1-N-(S-γ-amino-β-hydroxypropyl)-5-epi-amino-5-deoxygentamicin B,
3. 1-N-(S-γ-amino-β-hydroxypropyl)-5-epi-amino-5-deoxygentamicin $B_1$,
4. 1-N-(S-γ-amino-β-hydroxypropyl)-5-epi-amino-5-deoxygentamicin $C_{1a}$,
5. 1-N-(S-γ-amino-β-hydroxypropyl)-5-epi-amino-5-deoxygentamicin $C_2$,
6. 1-N-(S-γ-amino-βhydroxypropyl)-5-epi-amino-5-deoxygentamicin $C_{2a}$,
7. 1-N-(S-γ-amino-β-hydroxypropyl)-5-epi-amino-5-deoxygentamicin $C_{2b}$,
8. 1-N-(S-γ-amino-β-hydroxypropyl)-5-epi-amino-5-deoxygentamicin $X_2$,
9. 1-N-(S-γ-amino-β-hydroxypropyl)-5-epi-amino-5-deoxytobramycin,
10. 1-N-(S-γ-amino-β-hydroxypropyl)-5-epi-amino-5-deoxy-Antibiotic G-418,
11. 1-N-(S-γ-amino-β-hydroxypropyl)-5-epi-amino-5-deoxy-Antibiotic JI-20A,
12. 1-N-(S-γ-amino-β-hydroxypropyl)-5-epi-amino-5-deoxy-Antibiotic JI-20B,
13. 1-N-(S-γ-amino-β-hydroxypropyl)-5-epi-amino-5,3',4'-trideoxykanamycin B,
14. 1-N-(S-γ-amino-β-hydroxypropyl)-5-epi-amino-5-deoxykanamycin B,
15. 1-N-(S-γ-amino-β-hydroxypropyl)-5-epi-amino-5-deoxykanamycin A.

B. 1-N-Alkyl-5-Epi-amino-5-Deoxy Aminoglycosides
1. 1-N-Ethyl-5-Epi-Amino-5-Deoxygentamicin $C_1$ In a manner similar to that described in Example XV-A(1) treat 1-N-acetyl-5-epi-amino-5-deoxygentamicin $C_1$ with diborane in tetrahydrofuran. Isolate and purify the resultant products in a manner similar to that described in Example XV-A(1) to obtain 1-N-ethyl-5-epi-amino-5-deoxygentamicin $C_1$.

2. Treat the following 1-N-acetyl-5-epi-amino-4,6-di-O-(aminoglycosyl)-2,5-dideoxystreptamines in the manner of above Example XV-B(1).

1. 1-N-acetyl-5-epi-amino-5-deoxygentamicin A,
2. 1-N-acetyl-5-epi-amino-5-deoxygentamicin B,
3. 1-N-acetyl-5-epi-amino-5-deoxygentamicin $B_1$,
4. 1-N-acetyl-5-epi-amino-5-deoxygentamicin $C_{1a}$,
5. 1-N-acetyl-5-epi-amino-5-deoxygentamicin $C_2$,
6. 1-N-acetyl-5-epi-amino-5-deoxygentamicin $C_{2a}$,
7. 1-N-acetyl-5-epi-amino-5-deoxygentamicin $C_{2b}$,
8. 1-N-acetyl-5-epi-amino-5-deoxygentamicin $X_2$,
9. 1-N-acetyl-5-epi-amino-5-deoxytobramycin,
10. 1-N-acetyl-5-epi-amino-5-deoxy-Antibiotic G-418,
11. 1-N-acetyl-5-epi-amino-5-deoxy-Antibiotic JI-20A,
12. 1-N-acetyl-5-epi-amino-5-deoxy-Antibiotic JI-20B,
13. 1-N-acetyl-5-epi-amino-5,3',4'-trideoxykanamycin B,
14. 1-N-acetyl-5-epi-amino-5-deoxykanamycin B,
15. 1-N-acetyl-5-epi-amino-5-deoxykanamycin A.

Isolate and purify each of the resultant products in the manner similar to that described to obtain, respectively, 1. 1-N-ethyl-5-epi-amino-5-deoxygentamicin A,
2. 1-N-ethyl-5-epi-amino-5-deoxygentamicin B,
3. 1-N-ethyl-5-epi-amino-5-deoxygentamicin $B_1$,
4. 1-N-ethyl-5-epi-amino-5-deoxygentamicin $C_{1a}$,
5. 1-N-ethyl-5-epi-amino-5-deoxygentamicin $C_2$,
6. 1-N-ethyl-5-epi-amino-5-deoxygentamicin $C_{2a}$,
7. 1-N-ethyl-5-epi-amino-5-deoxygentamicin $C_{2b}$,
8. 1-N-ethyl-5-epi-amino-5-deoxygentamicin $X_2$,
9. 1-N-ethyl-5-epi-amino-5-deoxytobramycin,
10. 1-N-ethyl-5-epi-amino-5-deoxy-Antibiotic G-418,
11. 1-N-ethyl-5-epi-amino-5-deoxy-Antibiotic JI-20A,
12. 1-N-ethyl-5-epi-amino-5-deoxy-Antibiotic JI-20B,
13. 1-N-ethyl-5-epi-amino-5,3',4'-trideoxy-kanamycin B,
14. 1N-ethyl-5-epi-amino-5-deoxykanamycin B,
15. 1-N-ethyl-5-epi-amino-5-deoxykanamycin A.

3. 1-N-Ethyl-5-Epi-Amino-5-Deoxysisomicin

Suspend 1 gm. of 1-N-acetyl-5-epi-amino-5-deoxysisomicin in 100 ml. of tetrahydrofuran. Add 1 gm. of lithium aluminum hydride, then stir the resultant suspension at reflux temperature for 24 hours under an atmosphere of nitrogen. Cool and decompose the excess hydride by careful addition of ethyl acetate. Evaporate the reaction mixture to a small volume and dilute with water. Separate the insoluble solids by filtration and wash well with acetic acid. Evaporate the combined filtrate and washings and dissolve the resultant residue in water. Adjust the pH of the aqueous solution to about 7 by addition of ammonium hydroxide. Pass the solution through a column of IRC-50 resin in the ammonium cycle and wash the column well with water. Elute with 0.5 N ammonium hydroxide, evaporate the eluate, and chromatograph the resultant residue over 20 gm. of silica gel eluting with the lower phase of a 2:1:1 chloroform:methanol:concentrated ammonium hydroxide solvent system. Combine and evaporate the like fractions as determined by thin layer chromatography to obtain 1-N-ethyl-5-epi-amino-5-deoxysisomicin.

4. Treat the following 5-epi-amino-4,6-di-O-(aminoglycosyl)-2,5-dideoxystreptamines in the manner described in the procedure of Example XV-B(3).

1. 1-N-acetyl-5-epi-amino-5-deoxyverdamicin,
2. 1-N-acetyl-5-epi-amino-5-deoxy-Antibiotic 66-40B,
3. 1-N-acetyl-5-epi-amino-5-deoxy-Antibiotic 66-40D,
4. 1-N-acetyl-5-epi-amino-5-deoxy-Antibiotic G-52.

Isolate and purify each of the resultant products to obtain, respectively, 1. 1-N-ethyl-5-epi-amino-5-deoxyverdamicin,
2. 1-N-ethyl-5-epi-amino-5-deoxy-Antibiotic 66-40B,
3. 1-N-ethyl-5-epi-amino-5-deoxy-Antibiotic 66-40D,
4. 1-N-ethyl-5-epi-amino-5-deoxy-Antibiotic G-52.

EXAMPLE XVI

PREPARATION OF 1-N-ALKYL-4,6-DI-O-(AMINOGLYCOSYL)-2-DEOXYSTREPTAMINES VIA REACTION OF THE SULFATE SALT OF THE CORRESPONDING 1-N-UNSUBSTITUTED COMPOUND WITH AN ALDEHYDE FOLLOWED BY SODIUM CYANOBOROHYDRIDE

A. 1-N-Ethylsisomicin

To a solution of 5 gm. of sisomicin in 250 ml. of water add 1 N sulfuric acid until the pH of the solution is adjusted to about 5. To the solution of sisomicin sulfuric acid addition salt thereby formed, add 2 ml. of acetaldehyde, stir for 10 minutes, then add 0.85 gm. of sodium cyanoborohydride. Continue stirring at room temperature for 15 minutes, then concentrate the solution in vacuo to a volume of about 100 ml., treat the solution with a basic ion exchange resin (e.g. Amberlite IRA 401S (OH$^-$)), then lyophilize to a residue comprising 1-N-ethylsisomicin.

Purify by chromatographing on 200 gm. of silica gel, eluting with lower phase of a chloroform-methanol-7% aqueous ammonium hydroxide (2:1:1) system. Combine the like eluates as determined by thin layer chromatography and concentrate the combined eluates of the major component in vacuo to a residue comprising 1-N-ethylsisomicin (yield 1.25 gm.). Further purify by again chromatographing on 100 gm. of silica gel eluting with a chloroform-methanol-3.5% ammonium hydroxide (1:2:1) system. Pass the combined, like eluates (as determined by thin layer chromatography) through a column of basic ion exchange resin and lyophilize the eluate to obtain 1-N-ethylsisomicin (yield 0.54 gm.); $[\alpha]_D^{26} + 164°$ (0.3%, $H_2O$); pmr (ppm) ($D_2O$): δ 1.05 (3H, t, J=7Hz, —$CH_2CH_3$); 1.19 (3H, s, —C—$CH_3$); 2.5 (3H, s, N—$CH_3$); 4.85 (1H, m, =H—); 4.95 (1H, d, J=4Hz, $H_1''$); 5.33 (1H, d, J=2.5 Hz, $H_1'$).

Mass Spectrum: (M+1)$^+$ m/e 476
also m/e 127, 154, 160, 173, 191, 201, 219, 256, 299, 317, 332, 345, 350, 360, 378, 390, 400.

B. In the procedure of Examples XVI-A, substitute equivalent quantities of each of the 5-epi-azido (and 5-epi-amino)-5-deoxy aminoglycosides prepared as described in Example IX(A–D) and X(A–D) to obtain, respectively, 1. 1-N-ethyl-5-epi-amino-5-deoxygentamicin $C_{1a}$,
2. 1-N-ethyl-5-epi-amino-5-deoxygentamicin $C_1$,
3. 1-N-ethyl-5-epi-amino-5-deoxygentamicin $C_2$,
4. 1-N-ethyl-5-epi-amino-5-deoxygentamicin $C_{2a}$,
5. 1-N-ethyl-5-epi-amino-5-deoxygentamicin $C_{2b}$,
6. 1-N-ethyl-5-epi-amino-5-deoxysisomicin,
7. 1-N-ethyl-5-epi-amino-5-deoxy-Antibiotic G-252,
8. 1-N-ethyl-5-epi-amino-5-deoxy-Antibiotic 66-40D,
9. 1-N-ethyl-5-epi-amino-5-deoxyverdamicin,
10. 1-N-ethyl-5-epi-amino-5-deoxy-Antibiotic 66-40B,
11. 1-N-ethyl-5-epi-amino-5,3',4'-trideoxykanamycin B,
12. 1-N-ethyl-5-epi-amino-5-deoxygentamicin B,
13. 1-N-ethyl-5-epi-amino-5-deoxygentamicin $B_1$,
14. 1-N-ethyl-5-epi-amino-5-deoxy-Antibiotic JI-20A,
15. 1-N-ethyl-5-epi-amino-5-deoxy-Antibiotic JI-20B,
16. 1-N-ethyl-5-epi-amino-5-deoxykanamycin B,
17. 1-N-ethyl-5-epi-amino-5-deoxytobramycin,
18. 1-N-ethyl-5-epi-amino-5-deoxygentamicin $X_2$,
19. 1-N-ethyl-5-epi-amino-5-deoxy-Antibiotic G-418,
20. 1-N-ethyl-5-epi-amino-5-deoxykanamycin A,
21. 1-N-ethyl-5-epi-amino-5-deoxygentamicin A,
22. 1-N-ethyl-5-epi-azido-5-deoxygentamicin $C_{1a}$,
23. 1-N-ethyl-5-epi-azido-5-deoxygentamicin $C_1$,
24. 1-N-ethyl-5-epi-azido-5-deoxygentamicin $C_2$,
25. 1-N-ethyl-5-epi-azido-5-deoxygentamicin $C_{2a}$,
26. 1-N-ethyl-5-epi-azido-5-deoxygentamicin $C_{2b}$,
27. 1-N-ethyl-5-epi-azido-5-deoxysisomicin,
28. 1-N-ethyl-5-epi-azido-5-deoxy-Antibiotic G-52,
29. 1-N-ethyl-5-epi-azido-5-deoxy-Antibiotic 66-40D,
30. 1-N-ethyl-5-epi-azido-5-deoxyverdamicin,
31. 1-N-ethyl-5-epi-azido-5-deoxy-Antibiotic 66-40B,
32. 1-N-ethyl-5-epi-azido-5,3',4'-trideoxykanamycin B,
33. 1-N-ethyl-5-epi-azido-5-deoxygentamicin B,
34. 1-N-ethyl-5-epi-azido-5-deoxygentamicin $B_1$,
35. 1-N-ethyl-5-epi-azido-5-deoxy-Antibiotic JI-20A,
36. 1-N-ethyl-5-epi-azido-5-deoxy-Antibiotic JI-20B,
37. 1-N-ethyl-5-epi-azido-5-deoxykanamycin B,
38. 1-N-ethyl-5-epi-azido-5-deoxytobramycin,
39. 1-N-ethyl-5-epi-azido-5-deoxygentamicin $X_2$,
40. 1-N-ethyl-5-epi-azido-5-deoxy-Antibiotic G-418,
41. 1-N-ethyl-5-epi-azido-5-deoxykanamycin A,
42. 1-N-ethyl-5-epi-azido-5-deoxygentamicin A.

C. In the procedures of Examples XVI-A and B by substituting for acetaldehyde equivalent quantities of other aldehydes, e.g. propenal, butanal and δ-adetamidobutanal, there are obtained the corresponding 1-N-propyl, 1-N-butyl and 1-N-δ-acetamidobutyl derivatives of the 5-epi-amino-5-deoxy- and 5-epi-azido-5-deoxy aminoglycosides listed therein. Treatment of the 1-N-(δ-acetamidobutyl) derivatives with base yields the corresponding 1-N-(δ aminobutyl) derivatives.

EXAMPLE XVII

ACID ADDITION SALTS

A. Sulfate Salts (Sulfuric Acid Addition Salts)

Dissolve 5.0 gm. of 5-epi-amino-5-deoxygentamicin $C_1$ in 25 ml. of water and adjust the pH of the solution to 4.5 with 1N sulfuric acid. Pour into about 300 ml. of methanol with vigorous agitation, continue the agitation for about 10–20 minutes and filter. Wash the precipitate with methanol and dry at about 60° C in vacuo to obtain 5-epi-amino-5-deoxygentamicin $C_1$ sulfate.

In like manner, the sulfate salt of the compounds of Examples IX - XVI are also prepared.

B. Hydrochloride Salts

Dissolve 5.0 gm. of 5-epi-amino-5-deoxygentamicin $C_{1a}$ in 25 ml. of water. Acidify with 2N hydrochloric acid to pH 5. Lyophilize to obtain 5-epi-amino-5-deoxygentamicin $C_{1a}$ hydrochloride.

In like manner, the hydrochloride salt of the compounds of Examples IX–XVI may also be prepared.

The present invention includes within its scope pharmaceutical compositions comprising my novel 5-epi-X-4,6-di-O-(aminoglycosyl)-2,5-dideoxystreptamines (X being amino or azido) and the 1-N-alkyl derivatives thereof with a compatible, pharmaceutically acceptable carrier or coating. Also included within my invention is the method of eliciting an antibacterial response in a warm-blooded animal having a susceptible bacterial infection which comprises administering to said animal a non-toxic, antibacterially effective amount of a member selected from the group consisting of a 5-epi-X-5-deoxygentamicin A, 5-epi-X-5-deoxygentamicin B, 5-epi-X-5-deoxygentamicin $B_1$, 5-epi-X-5-deoxygentamicin $C_1$, 5-epi-X-5-deoxygentamicin $C_{1a}$, 5-epi-X-5- deoxygentamicin $C_2$, 5-epi-X-5-deoxygentamicin $C_{2a}$, 5-epi-X-5-deoxygentamicin $C_{2b}$, 5-epi-X-5-deoxygentamicin $X_2$, 5-epi-X-5-deoxysisomicin, 5-epi-X-5-deoxyverdamicin, 5-epi-X-5-deoxytobramycin, 5-epi-X-5-deoxy-Antibiotic G-418, 5-epi-X-5-deoxy-Antibiotic 66-40B, 5-epi-X-5-deoxy-Antibiotic 66-40D, 5-epi-X-5-deoxy-Antibiotic JI-20A, 5-epi-X-5-deoxy-Antibiotic JI-20B, 5-epi-X-5-deoxy-Antibiotic G-52, 5-epi-X-5-deoxykanamycin A, 5-epi-X-5-deoxykanamycin B, 5-epi-X-5,3',4'-trideoxykanamycin B, wherein X is a member selected from the group consisting of azido and amino;

the 1-N-K derivatives of the foregoing, wherein K is as hereinabove defined; and the non-toxic pharmaceutically acceptable acid addition salts thereof.

As discussed hereinabove, the 5-epi-X-4,6-di-O-(aminoglycosyl)-2,5-dideoxystreptamines of this invention such as defined by formulae I, II, III, IV, their 1-N-K derivatives, and the non-toxic, pharmaceutically acceptable acid addition salts thereof, are broad spectrum antibacterial agents which, advantageously, exhibit activity against organisms which are resistant to their 5-hydroxy precursors. Thus, the 5-epi-azido-5-deoxy- and the 5-epi-amino-5-deoxy compounds of this invention can be used alone or in combination with other antibiotic agents to prevent the growth or reduce the number of bacteria in various environments. They may be used, for example, to disinfect laboratory glassware, dental and medical equipment contaminated with *Staphylococcus aureus* or other bacteria inhibited by the 5-epi-amino-5-deoxy- and 5-epi-azido-5-deoxy-derivatives of this invention. The activity of the 5-epi-X-4,6-di-O-(aminoglycosyl)-2,5-dideoxystreptamines (X being azido or amino) against gram negative bacteria renders them useful for combating infections caused by gram negative organisms, e.g. species of Proteus and Pseudomonas. My 5-epi-X-4,6-di-O-(aminoglycosyl)-2,5-dideoxystreptamines, e.g. 5-epi-X-5-deoxysisomicin and 5-epi-X-5-deoxyverdamicin (X being azido or amino) have veterinary applications, particularly in the treatment of mastitis in cattle and Salmonella induced diarrhea in domestic animals such as the dog and the cat.

I, II, III and IV, particularly those defined by formula I, e.g. 5-epi-amino-5-deoxygentamicin $C_{1a}$ are also advantageously cidal against certain gram negative organisms which are resistant to the 5-hydroxy precursors.

The 5-epi-X-4,6-di-O-(aminoglycosyl)-2,5-dideoxystreptamines of formulae I, II, III and IV, their 1-N-alkyl derivatives, and the pharmaceutically acceptable acid addition salts thereof, may be administered orally. They may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example such substances as water, oils, greases, polyesters, polyols and the like.

For oral administration the 5-epi-amino- and 5-epi-azido-4,6-di-O-(aminoglycosyl)-2,5-dideoxystreptamine antibacterials of this invention may be compounded in the form of tablets, capsules, elixirs or the like or may even be admixed with animal feed. It is in these dosage forms that the antibacterials are most effective for treating bacterial infections of the gastrointestinal tract which infections cause diarrhea.

In general, the topical preparations will contain from about 0.1 to about 3.0 gms. of 5-epi-amino and 5-epi-azido-4,6-di-O-(aminoglycosyl)-2,5-dideoxystreptamine of formulae I, II, III and IV or a 1-N-alkyl derivative thereof, per 100 gms. of ointment, creams or lotion. The topical preparations are usually applied gently to lesions from about 2 to about 5 times a day.

The antibacterials of this invention may be utilized in liquid form such as solutions, suspension and the like for otic and optic use and may also be administered parenterally via intramuscular injection. The injectable solution or suspension will usually be administered at from about 1 mg. to about 10 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

| Tablet | Formulation 1 | | |
|---|---|---|---|
| | 10 mg. Tab. | 25 mg. Tab. | 100 mg. Tab. |
| 5-epi-amino-5-deoxy-gentamicin $C_{1a}$ | 10.5* mg. | 26.25* mg. | 105.0 mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

In general, the dosage administered of the 5-epi-X-4,6-di-O-(aminoglycosyl)-2,5-dideoxystreptamines will be dependent upon the age and weight of the animal species being treated, the mode of administration, and the type and severity of bacterial infection being prevented or reduced. In general, the dosage of 5-epi-X-4,6-di-O-(aminoglycosyl)-2,5-dideoxystreptamines employed to combat a given bacterial infection will be similar to the dosage requirements of the corresponding 5-hydroxy-4,6-di-O-(aminoglycosyl)-2,5-dideoxystreptamines. Additionally, the 5-epi-amino-4,6-di-O-(aminoglycosyl)-2,5-dideoxystreptamines of formulae Procedure Prepare a slurry consisting of the 5-epi-amino-5-deoxygentamicin $C_{1a}$ lactose and polyvinylpyrrolidone. Spray dry the slurry. Add the corn starch and magnesium stearate. Mix and compress into tablets.

| Formulation 2 | |
|---|---|
| Ointment | |
| 5-epi-azido-5-deoxygentamicin $C_{1a}$ | 1.9 gm. |
| Methyl paraben U.S.P. | 0.5 gm. |
| Propyl paraben U.S.P. | 0.1 gm. |

-continued

Formulation 2

Ointment

| | | |
|---|---|---|
| Petrolatum | to | 1000 gm. |

Procedure
1. Melt the petrolatum.
2. Mix the 5-epi-azido-5-deoxygentamicin $C_{1a}$, methylparaben and propylparaben with about 10% of the molten petrolatum.
3. Pass the mixture through a colloid mill.
4. Add the remainder of the petrolatum with agitation and cool the mixture until it becomes semi-solid. At this stage the product may be put into suitable containers.

Ointments of 5-epi-X-4,6-di-O-(aminoglycosyl)-2,5-dideoxystreptamines of formulae I, II, III and IV (X being amino or azido) and their 1-N-alkyl derivatives, and of the acid addition salts thereof are prepared by substituting an equivalent quantity of 5-epi-X-4,6-di-O-(aminoglycosyl)-2,5-dideoxystreptamine (X being amino or azido) or acid addition salt for 5-epi-azido-5-deoxygentamicin $C_{1a}$ in the foregoing example and by following substantially the procedure of the example.

Formulation 3

| Injectable Solution | Per 2.0 ml. vial | Per 50 Liters |
|---|---|---|
| 5-epi-amino-5-deoxy-gentamicin $C_{1a}$ | 84* mgs. | 2100* gms. |
| Methyl paraben, U.S.P. | 3.6 mgs. | 90.0 gms. |
| Propyl paraben, U.S.P. | 0.4 mgs. | 10.0 gms. |
| Sodium bisulfite, U.S.P. | 6.4 mgs. | 160.0 gms. |
| Disodium Ethylenediamine tetraacetate dihydrate, R.G. | 0.2 mgs. | 5.0 gms. |
| Water, U.S.P. q.s. | 2.0 ml. | 50.0 liters |

*Includes a 5% manufacturing overcharge.

Procedure: For a 50.0 liter batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°–30° C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 5-epi-amino-5-deoxygentamicin $C_{1a}$ sulfate. Bring the batch volume up to 50.0 liters with water for injection and agitate until homogeneous.

Under sterile conditions, filter the solution through a suitable bacteria retentive filter collecting the filtrate in a filling tank.

Fill the filtrate aseptically into sterile pyrogen-free multiple dose vials, stopper and seal.

In like manner, injectable solutions of other 5-epi-amino-5-deoxy and 5-epi-azido-5-deoxy-4,6-di-O-(aminoglycosyl)-2,5-dideoxystreptamines and especially acid addition salts of such antibacterial agents, may be prepared by substituting an equivalent quantity of such compounds for 5-epi-amino-5-deoxygentamicin $C_{1a}$ sulfate and by following the procedure set forth above.

I claim:

1. A compound selected from the group consisting of a 5-epi-X-4,6-di-O-(aminoglycosyl)-2,5-dideoxystreptamine selected from the group consisting of 5-epi-X-5-deoxygentamicin A, 5-epi-X-5-deoxygentamicin B, 5-epi-X-5-deoxygentamicin $B_1$, 5-epi-X-5-deoxygentamicin $C_1$, 5-epi-X-5-deoxygentamicin $C_{1a}$, 5-epi-X-5-deoxygentamicin $C_2$, 5-epi-X-5-deoxygentamicin $C_{2a}$, 5-epi-X-5-deoxygentamicin $C_{2b}$, 5-epi-X-5-deoxygentamicin $X_2$, 5-epi-X-5-deoxytobramycin, 5-epi-X-5-deoxyverdamicin, 5-epi-X-5-deoxykanamycin A, 5-epi-X-5-deoxykanamycin B, 5-epi-X-5,3',4'-trideoxykanamycin B, 5-epi-X-5-deoxy-Antibiotic G-52, 5-epi-X-5-deoxy-Antibiotic 66-40B, 5-epi-X-5-deoxy-Antibiotic 66-40D, 5-epi-X-5-deoxy-Antibiotic G-418, 5-epi-X-5-deoxy-Antibiotic JI-20A, 5-epi-X-5-deoxy-Antibiotic JI-20B, and 5-epi-X-5-deoxysisomicin; wherein X is a member selected from the group consisting of amino and azido;

and the 1-N-K derivatives of the foregoing,
wherein K is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; and the pharmaceutically acceptable acid addition salts thereof.

2. A compound of claim 1 wherein X is amino.
3. A compound of claim 1 wherein X is azido.
4. A compound of claim 1 wherein said 5-epi-X-4,6-di-O-(aminoglycosyl)-2,5-dideoxystreptamine is a 5-epi-amino-4-O-aminoglycosyl-6-O-garosaminyl-2,5-dideoxystreptamine.
5. A compound of claim 1 wherein said 5-epi-X-4,6-di-O-(aminoglycosyl)-2,5-dideoxystreptamine is a 5-epi-azido-4-O-aminoglycosyl-6-O-garosaminyl-2,5-dideoxystreptamine.
6. A compound of claim 4 which is 5-epi-amino-5-deoxygentamicin $C_1$.
7. A compound of claim 4 which is 5-epi-amino-5-deoxygentamicin $C_{1a}$.
8. A compound of claim 4 which is 5-epi-amino-5-deoxygentamicin $C_2$.
9. A compound of claim 4 which is 5-epi-amino-5-deoxygentamicin $C_{2a}$.
10. A compond of claim 4 which is 5-epi-amino-5-deoxygentamicin $C_{2b}$.
11. A compound of claim 4 which is 5-epi-amino-5-deoxysisomicin.
12. A compound of claim 4 which is 5-epi-amino-5-deoxyverdamicin.
13. A compound of claim 4 which is 5-epi-amino-5-deoxyAntibiotic G-52.
14. A compound of claim 2 which is 5-epi-amino-5-deoxyAntibiotic 66-40D.
15. A compound of claim 5 which is 5-epi-azido-5-deoxygentamicin $C_1$.
16. A compound of claim 5 which is 5-epi-azido-5-deoxygentamicin $C_{1a}$.
17. A compound of claim 5 which is 5-epi-azido-5-deoxygentamicin $C_2$.
18. A compound of claim 5 which is 5-epi-azido-5-deoxygentamicin $C_{2a}$.

19. A compound of 2b5 which is 5-epi-azido-5-deoxygentamicin $C_{2b}$.

20. A compound of claim 5 which is 5-epi-azido-5-deoxysisomicin.

21. A compound of claim 5 which is 5-epi-azido-5-deoxyverdamicin.

22. A compound of claim 5 which is 5-epi-azido-5-deoxy-Antibiotic G-52.

23. A compound of claim 3 which is 5-epi-azido-5-deoxy-Antibiotic 66-40D.

24. A 1-N-K derivative of claim 1 wherein K is an alkyl substituent having up to 4 carbon atoms.

25. A 1-N-K derivative of claim 1 wherein K is ethyl.

26. A compound selected from the group consisting of a 1N-acyl derivative of a 5-epi-X-4,6-di-O-(aminoglycosyl)-2,5-dideoxystreptamine selected from the group consisting of 5-epi-X-5-deoxygentamicin A, 5-epi-X-5-deoxygentamicin B, 5-epi-X-5-deoxygentamicin $B_1$, 5-epi-X-5-deoxygentamicin $C_1$, 5-epi-X-5-deoxygentamicin $C_{1a}$, 5-epi-X-5-deoxygentamicin $C_2$, 5-epi-X-5-deoxygentamicin $C_{2a}$, 5-epi-X-5-deoxygentamicin $C_{2b}$, 5-epi-X-5-deoxygentamicin $X_2$, 5-epi-X-5-deoxytobramycin, 5-epi-X-5-deoxyverdamicin, 5-epi-X-5-deoxykanamycin A, 5-epi-X-5-deoxykanamycin B, 5-epi-X-5,3',4'-trideoxykanamycin B, 5-epi-X-5-deoxy-Antibiotic G-52, 5epi-X-5-deoxy-Antibiotic 66-40B, 5-epi-X-5-deoxy-Antibiotic 66-40D, 5-epi-X-5-deoxy-Antibiotic G-418, 5-epi-X-5-deoxy-Antibiotic JI-20A, 5-epi-X-5-deoxy-Antibiotic JI-20B and 5-epi-X-5-deoxysisomicin;

wherein said acyl is

with K' being hydrogen or an alkyl substituent selected from the group consisting of alkyl, cycloalkyl, alkenyl, aralkyl, hydroxyalkyl, aminoalkyl, alkylaminoalkyl, aminohydroxyalkyl, and alkylaminohydroxyalkyl, said alkyl substituent having up to 7 carbon atoms, and when said alkyl substituent is substituted by both hydroxyl and amino functions, only one of said functions can be attached at any one carbon atom;

and the acid addition salts thereof.

27. A compound of claim 26 wherein said 1-N-acyl is 1-N-acetyl.

28. A compound of claim 26 wherein said 1-N-acyl is 1-N-(S-4-amino-2-hydroxybutyryl).

29. A compound of claim 26 wherein said 1-N-acyl is 1-N-(S-3-amino-2-hydroxypropionyl).

30. A compound selected from the group consisting of 1,3,2',6'-tetra-N-Y-5-epi-azido-5-deoxy-2''-O-Z-3'',4''-N,O-carbonyl-4,6-di-O-(aminoglycosyl)-2-deoxystreptamine wherein Y is a member selected from the group consisting of benzyloxycarbonyl, alkoxybenzyloxycarbonyl and alkoxycarbonyl; Z is hydrocarboncarbonyl, said hydrocarbon having up to 8 carbon atoms; and said 4,6-di-O-(aminoglycosyl)-2-deoxystreptamine is a member selected from the group consisting of gentamicin $C_1$, gentamicin $C_{1a}$, gentamicin $C_2$, gentamicin $C_{2a}$, gentamicin $C_{2b}$, Antibiotic G-52, verdamicin, sisomicin and Antibiotic 66-40D;

and the 1-N-K'' derivatives of the foregoing wherein K'' is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; any amino function being substituted by said group Y, and any hydroxyl being converted to an ester OZ, or, when said hydroxyl group is alpha or beta to an amino protecting group Y, the hydroxyl group together with said protecting group Y is converted to an oxazolidinone or a tetrahydro-1,3-oxazin-2-one, respectively, Y and Z being as hereinabove defined.

31. A compound of claim 30 wherein Y is benzyloxycarbonyl and Z is benzoyl.

32. A compound selected from the group consisting of 1,3,2',6',3''-penta-N-Y-5-epi-azido-5-deoxy-4',2''-di-O-Z-4'',6''-O-W-tobramycin, 1,3,2',6',3''-penta-N-Y-5-epi-azido-2''-O-Z-4'',6''-O-W-5,3',4'-trideoxykanamycin B, 1,3,2',3''-tetra-N-Y-5-epi-azido-5-deoxy-3',2'',4''-tri-O-Z-4',6'-O-W-gentamicin A, and 1,3,2',6',3''-penta-N-Y-5-epi-azido-5-deoxy-3',4';-4'',6''-di-O-W-2''-O-Z-kanamycin B;

wherein M is a member selected from the group consisting of alkylidene, cycloalkylidene and arylalkylidene; Y is a member selected from the group consisting of lower alkanoyl, benzyloxycarbonyl, alkoxybenzyloxycarbonyl and alkoxycarbonyl; Z is hydrocarboncarbonyl, said hydrocarbon having up to 8 carbon atoms;

and the 1-N-K'' derivatives of the foregoing, K'' being an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; any amino function being substituted by said group Y, and any hydroxyl being converted to an ester OZ, or, when said hydroxyl group is alpha or beta to an amino protecting group Y, the hydroxyl group together with said protecting group Y is converted to an oxazolidinone or a tetrahydro-1,3-oxazin-2-one, respectively, Y and Z being as hereinabove defined.

33. A compound of claim 32 wherein W is benzylidene, Y is benzyloxycarbonyl and Z is benzoyl.

34. A compound selected from the group consisting of 1,3-di-N-Y-5-epi-azido-5-deoxy-2',3'-O-W-6',4';3'λ',4''-di-N,O-carbonyl-2''-O-Z-gentamicin B, 1,3-di-N-Y-5-epi-azido-5-deoxy-2',3'-O-W-6',4';3'λ',4''-di-N,O-carbonyl-2''-O-Z-gentamicin $B_1$, 1,3,2'-tri-N-Y-5-epi-azido-5-deoxy-3',2''-di-O-Z-4',6'-O-W-3'',4''-N,O-carbonyl-gentamicin $X_2$, 1,3,2'-tri-N-Y-5-epi-azido-5-deoxy-3',2''-di-O-Z-4',6'-O-W-3'',4''-N,O-carbonyl-Antibiotic G-418, 1,3,2',6'-tetra-N-Y-5-epi-azido-5-deoxy-3',4'-O-W-2''-O-Z-3'',4''-N,O-carbonyl-Antibiotic JI-20A, and 1,3,2',6'-tetra-N-Y-5-epi-azido-5-deoxy-3',4'-O-W-2''-O-Z-3'',4''-N,O-carbonyl-Antibiotic JI-20B, wherein W is a member selected from the group consisting of alkylidene, cycloalkylidene and aralkylidene; Y is a member selected from the group consisting of benzyloxycarbonyl, alkoxybenzyloxycarbonyl and alkoxycarbonyl; Z is hydrocarboncarbonyl, said hydrocarbon having up to 8 carbon atoms;

and the 1-N-K'' derivatives thereof wherein K'' is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; any amino function being substituted by said group Y, and any hydroxyl being converted to an ester OZ, or, when said hydroxyl group is alpha or beta to an amino protectinng group Y, the hydroxyl group together with said protecting group Y is converted to an oxazolidinone or a tetrahydro-1,3-oxazin-2-one, respectively, Y and Z being as hereinabove defined.

35. A compound of claim 34 wherein W is benzylidene, Y is benzyloxycarbonyl and Z is benzoyl.

36. 1,3,2',6',3''-Penta-N-Y-5-epi-azido-5-deoxy-2'',4''-di-O-Z-Antibiotic 66-40-B, wherein Y is a member selected from the group consisting of lower alkanoyl, benzyloxycarbonyl, alkoxybenzyloxycarbonyl and alkoxycarbonyl; and Z is hydrocarboncarbonyl, said hydrocarbon having up to 8 carbon atoms;

and the 1-N-K''-derivatives thereof wherein K'' is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; any amino function being substituted by said group Y, and any hydroxyl being converted to an ester OZ, or, when said hydroxyl group is alpha or beta to an amino protectinng group Y, the hydroxyl group together with said protecting group Y is converted to an oxazolidinone or a tetrahydro-1,3-oxazin-2-one, respectively, Y and Z being as hereinabove defined.

37. A compound of claim 36 wherein Y is benzyloxycarbonyl and Z is benzoyl.

38. The process for preparing a 5-epi-amino-4,6-di-O-(aminoglycosyl)-2,5-dideoxystreptamine selected from the group consisting of:

5-epi-amino-5-deoxygentamicin A, 5-epi-amino-5-deoxygentamicin B, 5-epi-amino-5-deoxygentamicin $B_1$, 5-epi-amino-5-deoxygentamicin $C_1$, 5-epi-amino-5-deoxygentamicin $C_{1a}$, 5-epi-amino-5-deoxygentamicin $C_2$, 5-epi-amino-5-deoxygentamicin $C_{2a}$, 5-epi-amino-5-deoxygentamicin $C_{2b}$, 5-epi-amino-5-deoxygentamicin $X_2$, 5-epi-amino-5,3',4'-trideoxykanamycin B, 5-epi-amino-5-deoxytobramycin, 5-epi-amino-5-deoxykanamycin A, 5-epi-amino-5-deoxykanamycin B, 5-epi-amino-5-deoxyverdamicin, 5-epi-amino-5-deoxy-Antibiotic G-52, 5-epi-amino-5-deoxy-Antibiotic G-418, 5-epi-amino-5-deoxy-Antibiotic 66-40B, 5-epi-amino-5-deoxy-Antibiotic 66-40D, 5-epi-amino-5-deoxy-Antibiotic JI-20A, 5-epi-amino-5-deoxy-Antibiotic JI-20B and 5-epi-amino-5-deoxysisomicin;

and the 1-N-K derivatives thereof, wherein K is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;

which comprises the reaction of the corresponding 5-epi-azido-2''-O-Z-4,6-di-O-(aminoglycosyl)-2,5-dideoxystreptamine wherein Z is hydrocarboncarbonyl, said hydrocarbon having up to 8 carbon atoms; and wherein all other hydroxyl functions and all amino functions are protected by groups susceptible to reductive cleavage or to basic or mild acid hydrolysis; with hydrogen in the presence of a catalyst or with an alkali metal in liquid ammonia;

and the reaction of the thereby formed 5-epi-amino-4,6-di-O-(aminoglycosyl)-2,5-dideoxystreptamine derivative having hydroxyl and amino protecting groups susceptible to basic or mild acid hydrolytic cleavage with aqueous base followed by treatment with aqueous mild acid when any of said protecting groups are acetals or ketals.

39. The process of claim 38 wherein Z is benzoyl.

40. The process of claim 38 wherein said 5-epi-azido-2''-O-Z-4,6-di-O-(aminoglycosyl)-2,5-dideoxystreptamine wherein Z is hydrocarboncarbonyl, said hydrocarbon having up to 8 carbon atoms; and wherein all other hydroxyl functions and all amino functions are protected by groups susceptible to reductive cleavage or to basic or mild acid hydrolysis, is prepared by the reaction of the corresponding 5-O-R-2''-O-Z-4,6-di-O-(aminoglycosyl)-2-deoxystreptamine wherein R is a member selected from the group consisting of nitrobenzenesulfonyl, hydrocarbonsulfonyl and halogenohydrocarbonsulfonyl, said hydrocarbon having up to 8 carbon atoms; with an alkali metal azide in an organic solvent at elevated temperatures in the range from about 100° C to about 230° C.

41. The process of claim 40 wherein R is methanesulfonyl, Z is benzoyl, and said elevated temperature is about 120° C.

42. The process for preparing a 5-epi-azido-4,6-di-O-(aminoglycosyl)-2,5-dideoxystreptamine selected from the group consisting of: 5-epi-azido-5-deoxygentamicin A, 5-epi-azido-5-deoxygentamicin B, 5-epi-azido-5-deoxygentamicin $B_1$, 5-epi-azido-5-deoxygentamicin $C_1$, 5-epi-azido-5-deoxygentamicin $C_{1a}$, 5-epi-azido-5-deoxygentamicin $C_2$, 5-epi-azido-5-deoxygentamicin $C_{2a}$, 5-epi-azido-5-deoxygentamicin $C_{2b}$, 5-epi-azido-5-deoxygentamicin $X_2$, 5-epi-azido-5,3',4'-trideoxykanamycin B, 5-epi-azido-5-deoxykanamycin A, 5-epi-azido-5-deoxykanamycin B, 5-epi-azido-5-deoxytobramycin, 5-epi-azido-5-deoxyverdamicin, 5-epi-azido-5- deoxy-Antibiotic G-52, 5-epi-azido-5-deoxy-Antibiotic G-418, 5-epi-azido-5-deoxy-Antibiotic 66-40B, 5-epi-azido-5-deoxy-Antibiotic 66-40D, 5-epi-azido-5-deoxy-Antibiotic JI-20A, 5-epi-azido-5-deoxy-Antibiotic JI-20B, and 5-epi-azido-5-deoxysisomicin;

and the 1-N-K derivatives thereof wherein K is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;

which comprises the reaction of the corresponding 5-epi-azido-2''-O-Z-4,6-di-O-(aminoglycosyl)-2,5-dideoxystreptamine having hydroxyl and amino protecting groups susceptible to basic or mild acid hydrolytic cleavage, with aqueous base at temperatures in the range from about 90° C to about 100° C, and when any of said protecting groups are acetals or ketals, with aqueous mild acid.

43. The method of eliciting an antibacterial response in a warm-blooded animal having a susceptible bacterial infection, which comprises administering to said animal a non-toxic, anti-bacterially effective amount of a member selected from the group consisting of 5-epi-X-4,6-di-O-(aminoglycosyl)-2,5-dideoxystreptamine selected from the group consisting of 5-epi-X-5-deoxygentamicin A, 5-epi-X-5-deoxygentamicin B, 5-epi-X-5-deoxygentamicin $B_1$, 5-epi-X-5-deoxygentamicin $C_1$, 5-epi-X-5-deoxygentamicin $C_{1a}$, 5-epi-X-5-deoxygentamicin $C_2$, 5-epi-X-5-deoxygentamicin $C_{2a}$, 5-epi-X-5-deoxygentamicin $C_{2b}$, 5-epi-X-5-deoxygentamicin $X_2$, 5-epi-X-5-deoxytobramycin, 5-epi-X-5-deoxyverdamicin, 5-epi-X-5,3',4'-trideoxykanamycin B, 5-epi-X-5-deoxykanamycin A, 5-epi-X-5-deoxykanamycin B, 5-epi-X-5-deoxy-Antibiotic G-52, 5-epi-X-5-deoxy-Antibiotic 66-40B, 5-epi-X-5-deoxy-Antibiotic 66-40D, 5-epi-X-5-deoxy-Antibiotic G-418, 5-epi-X-5-deoxy-Antibiotic JI-20A, 5-epi-X-5-deoxy-Antibiotic JI-20B, and 5-epi-X-5-deoxysisomicin;

wherein X is a member selected from the group consisting of amino and azido; and the 1-N-K derivatives thereof wherein K is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;

and the pharmaceutically acceptable acid addition salts thereof.

44. A pharmaceutical composition comprising an inert carrier and, an antibacterially effective amount of a compound selected from the group consisting of 5-epi-X-4,6-di-O-(aminoglycosyl)-2,5-dideoxystreptamine selected from the group consisting of 5-epi-X-5-deoxygentamicin A, 5-epi-X-5-deoxygentamicin B, 5-epi-X-5-deoxygentamicin $B_1$, 5-epi-X-5-deoxygentamicin $C_1$, 5-epi-X-5-deoxygentamicin $C_{1a}$, 5-epi-X-5-deoxygentamicin $C_2$, 5-epi-X-5-deoxygentamicin $C_{2a}$, 5-epi-X-5-deoxygentamicin $C_{2b}$, 5-epi-X-5-deoxygentamicin $X_2$, 5-epi-X-5-deoxytobramycin, 5-epi-X-5-deoxyverdamicin, 5-epi-X-5,3',4'-trideoxykanamycin B, 5-epi-X-5-deoxykanamycin A, 5-epi-X-5-deoxykanamycin B, 5-epi-X-5-deoxy-Antibiotic G-52, 5-epi-X-5-deoxy-Antibiotic 66-40B, 5-epi-X-5-deoxy-Antibiotic 66-40D, 5-epi-X-5-deoxy-Antibiotic G-418, 5-epi-X-5-deoxy-Antibiotic JI-20A, 5-epi-X-5-deoxy-Antibiotic JI-20B, and 5-epi-X-5-deoxysisomicin;

wherein X is a member selected from the group consisting of amino and azido; and the 1-N-K derivatives thereof wherein K is an alkyl substituent selected from the group consisting of alkyl, alkylcycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;

and the pharmaceutically acceptable acid addition salts thereof.

* * * * *

UNITED STATES PATENT OFFICE
CERTIFICATE OF CORRECTION

Patent No. 4,000,262         Dated December 28, 1976

Inventor(s) Peter J. L. Daniels

It is certified that error appears in the above-identified patent and that said Letters Patent are hereby corrected as shown below:

Column 10, line 10, "1,3,2',6"-" should read ---1,3,2',6'---.
Column 11, line 45, "-di-$\underline{O}$-Z-Kanamycin B" should read ---di-$\underline{O}$-W-2"-$\underline{O}$-Z-Kanamycin B---. Column 13, lines 19 and 20, "-6',4'; 3' $\lambda$',4"-" should read ---6',4';3",4"---. Column 15, lines 1-15,

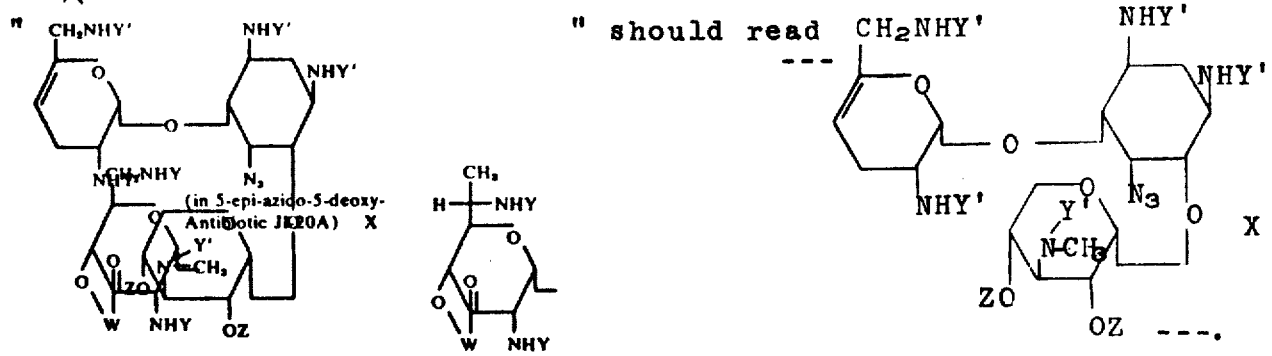

Column 16, lines 5-18, "(in 5-epi-azido-5-deoxy-Antibiotic JI-20B)" should read ---

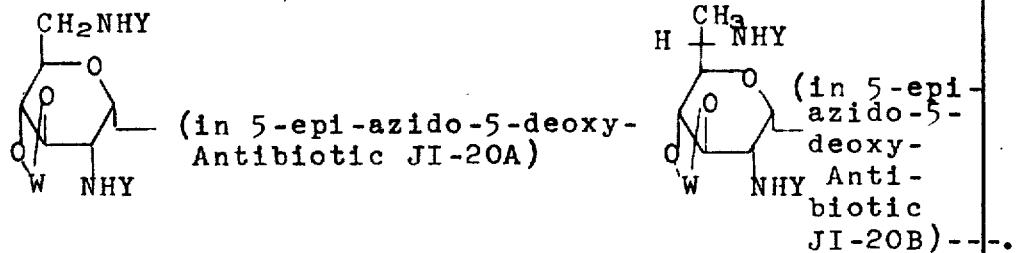

Column 22, line 18, "3',4"" should read ---3",4"---. Column 28, line 51, "6$\alpha$" should read ---6'---. Column 35, line 4, "3 + 50" should read ---3 x 50---. Column 46, lines 39 and 40, "-3",4'$\lambda$'-" should read ---3",4"---; lines 45 and 46, "-3",4'$\lambda$'-" should read ---3",4"---; lines 48 and 49, "-3",4'$\lambda$'-" should read ---3",4"---; line 60, "-propyl)-" should read ---propenyl)---.
Column 47, lines 5 and 6, "-3",4'$\lambda$'-" should read ---3",4"---.
Column 47, line 25, "B. 1-$\underline{N}$-" should read ---D. 1-$\underline{N}$---.

UNITED STATES PATENT OFFICE
CERTIFICATE OF CORRECTION

Patent No. 4,000,262      Dated December 28, 1976

Inventor(s) Peter J. L. Daniels

It is certified that error appears in the above-identified patent and that said Letters Patent are hereby corrected as shown below:

Column 52, line 43, "-pentanoyl)-6-" should read ---pentanoyl)-5---. Column 53, line 35, "-5-epi-Azido-epi-amino-5-epi-Amino-" should read ---5-epi-azido and 5-epi-amino---. Column 55, line 18, "1-N-(S-4-amino-2-Amino-2-Hydroxybutyryl)-" should read ---1-N-(S-4-Amino-2-Hydroxybutyryl)---. Column 59, line 38, "(1H, m, =H-);" should read ---(1H, m, =CH-);---. Column 65, line 1, Claim 19, "of 2b5" should read ---of claim 5---. Column 66, lines 58 and 59, Claim 34, "3'$\lambda$',4"-" should read ---3",4"---. Column 66, lines 60 and 61, Claim 34, "3'$\lambda$',4"-" should read ---3",4"---.

Signed and Sealed this

Twenty-sixth Day of April 1977

[SEAL]

Attest:

RUTH C. MASON
*Attesting Officer*

C. MARSHALL DANN
*Commissioner of Patents and Trademarks*